(12) United States Patent
Robinson et al.

(10) Patent No.: US 9,616,057 B2
(45) Date of Patent: Apr. 11, 2017

(54) DESETHYLHYDROXYCHLOROQUINE FOR THE TREATMENT OF DISEASES ASSOCIATED WITH INFLAMMATION

(71) Applicants: The Board of Trustees of the Leland Stanford Junior University, Palo Alto, CA (US); The United States Government As Represented By The Department of Veterans Affairs, Washington, DC (US)

(72) Inventors: William H. Robinson, Palo Alto, CA (US); Jeremy Sokolove, Mountain View, CA (US); Qian Wang, Palo Alto, CA (US)

(73) Assignees: The Board of Trustees of the Leland Stanford Junior University, Stanford, CA (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/214,307

(22) Filed: Mar. 14, 2014

(65) Prior Publication Data
US 2014/0275164 A1   Sep. 18, 2014

Related U.S. Application Data

(60) Provisional application No. 61/791,320, filed on Mar. 15, 2013.

(51) Int. Cl.
| | |
|---|---|
| A61K 31/40 | (2006.01) |
| A61K 31/4706 | (2006.01) |
| A61K 45/06 | (2006.01) |
| G01N 33/68 | (2006.01) |

(52) U.S. Cl.
CPC .......... *A61K 31/4706* (2013.01); *A61K 31/40* (2013.01); *A61K 45/06* (2013.01); *G01N 33/6893* (2013.01)

(58) Field of Classification Search
CPC ............... A61K 31/4706; A61K 31/40
USPC ........................................................ 514/313
See application file for complete search history.

(56) References Cited

U.S. PATENT DOCUMENTS

| | | | | |
|---|---|---|---|---|
| 3,019,169 | A | * 1/1962 | Klumpp et al. | ............... 424/471 |
| 2004/0229908 | A1 | 11/2004 | Nelson | |
| 2007/0003636 | A1 | 1/2007 | Mach | |
| 2008/0044390 | A1 | 2/2008 | Jin | |
| 2008/0319010 | A1 | 12/2008 | Kastan | |
| 2012/0202849 | A1 | 8/2012 | Pareek | |

FOREIGN PATENT DOCUMENTS

| | | |
|---|---|---|
| CA | 784722 A | 5/1968 |
| WO | 2010127313 A1 | 11/2010 |
| WO | 2012071042 A1 | 5/2012 |
| WO | 2014031769 A2 | 2/2014 |

OTHER PUBLICATIONS

Cardoso; et al. "Enantioselective metabolism of hydroxychloroquine employing rats and mice hepatic microsomes" Brazilian Journal of Pharmaceutical Sciences (Oct. 2009), 45(4):659-667.
Flach. "Improving the Risk-Benefit Relationship and Informed Consent for Patients Treated with Hydroxychloroquine" Transactions of the American Opthalmological Society (2007), 105:191-194.
Furst; et al. "Dose-loading with Hydroxychloroquine improves the Rate of Response in Early, Active Rheumatoid Arthritis" Arthritis & Rheumatism (Feb. 1999), 42(2):357-365.
Kalia; et al. "New concepts in antimalarial use and mode of action in dermatology" Dermatologic Therapy (Jul. 2007), 20(4):160-174.
Levy; et al. "Incidence of hydroxychloroquine retinopathy in 1,207 patients in a large multicenter outpatient practice" Arthritis Rheumatism (Aug. 1997), 40(8):1482-1486.
Marmor; et al. "Revised recommendations on screening for chloroquine and hydroxychloroquine retinopathy" Ophthalmology (Feb. 2011), 118(2):415-22.
Mavrikakis; et al. "The incidence of irreversible retinal toxicity in patients treated with hydroxychloroquine: a reappraisal" Opthalmology (Jul. 2003), 110(7):1321-1326.
Mecklenburg; et al. "An overview on the toxic morphological changes in the retinal pigment epithelium after systemic compound administration" Toxicol Pathology (Feb. 2007), 35(2):252-67.
Munster; et al. "Hydroxychloroquine Concentration-Response Relationships in Patients With Rheumatoid Arthritis" Arthritis & Rheumatism (Jun. 2002), 46(6):1460-1469.
O'Dell. "Therapeutic Strategies for Rheumatoid Arthritis" The New England Journal of Medicine (Jun. 2004), 350 (25):2591-602.
"The PDR Pocket Guide to Prescription Drugs" Pocket Books (2000), Fourth Edition, ISBN: 0-671-78643-1, pp. 5.
Wolfe; et al. "Rates and Predictors of Hydroxychloroquine Retinal Toxicity in Patients With Rheumatoid Arthritis and Systemic Lupus Erythematosus" Arthritis Care and Research (Jun. 2010), 62(6):775-784.
Yoon; et al. "Induction of Lysosomal Dilatation, Arrested Autophagy, and Cell Death by Chloroquine in Cultured ARPE-19 Cells" Retinal Cell Biology (Nov. 2010), 51(11):6030-6037.
Munster et al., Relationship between hydroxychloroquine (HCQ) blood concentrations and response in patients with rheumatoid arthritis (RA), Arthritis and Rheumatism, Nov. 16, 1999, p. S349, (#1671) vol. 42. No. 9 Suppl, Database Biosis [Online], Biosciences Information Service, Philadelphia, PA.

* cited by examiner

*Primary Examiner* — Raymond Henley, III
(74) *Attorney, Agent, or Firm* — Pamela J. Sherwood; Bozicevic, Field & Francis LLP

(57) ABSTRACT

Compositions and methods are provided for inhibiting or treating the early and established stages of inflammatory diseases by administration of an effective dose of the desethylhydroxychloroquine (DHCQ). A benefit of the methods is the ability to deliver a dose of agent that is effective in treating inflammation while sparing the individual from retinal toxicity.

32 Claims, 25 Drawing Sheets

|  | Control (vehicle) | HCQ | DHCQ |
|---|---|---|---|
| Cartilage Degeneration Score (*Maximum score per joint :72) | 39.00±6.9 | 33.9±10.8 | 29.00±7.5 |
| P value (compared to control) |  | 0.31 | 0.03 |
| Osteophyte Score (*Maximum score per joint :6) | 5.14±0.69 | 2.14±0.69 | 3.14±0.38 |
| P value (compared to control) |  | <0.01 | <0.01 |
| Synovites Score (*Maximum score per joint :6) | 4.86±1.07 | 2.57±1.13 | 2.00±1.15 |
| P value (compared to control) |  | <0.01 | <0.01 |

Figure 6

| | Control (vehicle) | HCQ | Atorva | HCQ + Atorva | DHCQ | BDCQ | DCQ | DHCQ + Atorva | BDCQ + Atorva |
|---|---|---|---|---|---|---|---|---|---|
| Cartilage Degeneration Score (*Maximum score per joint :72) | 39.00+6.9 | 33.9+10.8 | 34.71+6.5 | 20.63+9 | 29.00+7.5 | 42.72+4.7 | 41.57+3.2 | 21.00+3.5 | 34.50+7 |
| P value (compared to control) | | 0.31 | 0.25 | <0.01 | 0.03 | 0.30 | 0.39 | <0.01 | 0.23 |
| Osteophyte Score (*Maximum score per joint :6) | 5.14+0.69 | 2.14+0.69 | 4.71+0.76 | 1.25+0.71 | 3.14+0.38 | 5.00+0.82 | 4.43+0.53 | 1.57+0.53 | 4.75+0.71 |
| P value (compared to control) | | <0.01 | 0.29 | <0.01 | <0.01 | 0.730 | 0.051 | <0.01 | 0.29 |
| Synovites Score (*Maximum score per joint :6) | 4.86+1.07 | 2.57+1.13 | 4.29+1.25 | 0.86+0.90 | 2.00+1.15 | 4.57+0.53 | 4.43+1.13 | 1.00+0.58 | 3.88+0.83 |
| P value (compared to control) | | 0.02 | 0.38 | <0.01 | <0.05 | 0.54 | 0.48 | <0.01 | 0.067 |

Figure 20

| P value | HCQ+Atorva vs. HCQ | HCQ+Atorva vs. Atorva | DHCQ+Atorva vs. DHCQ | DHCQ+Atorva vs. Atorva |
|---|---|---|---|---|
| Cartilage Degeneration Score | 0.02 | 0.01 | <0.03 | <0.01 |
| Osteophyte Score | 0.03 | <0.01 | <0.01 | <0.01 |
| Synovitis Score | 0.01 | <0.01 | 0.05 | <0.01 |

Figure 21

DESETHYLHYDROXYCHLOROQUINE FOR THE TREATMENT OF DISEASES ASSOCIATED WITH INFLAMMATION

GOVERNMENT RIGHTS

This invention was made with Government support under contract nos. AI069160 and HV000242 awarded by the National Institutes of Health. The Government has certain rights in the invention.

FIELD OF THE INVENTION

In various embodiments, the present invention relates to compositions comprising desethylhydroxychloroquine (DHCQ) and methods for preventing and treating inflammatory diseases or diseases associated with inflammation with such compositions. Inflammatory diseases, or diseases associated with inflammation, include autoimmune diseases, degenerative diseases, metabolic diseases, cardiovascular diseases, chronic infections, and malignancies. In other embodiments, the present invention relates to the prevention of or treatment of such inflammatory diseases or diseases associated with inflammation, including preventing the onset of disease in individuals at increased risk for developing the disease, preventing the progression of disease in individuals at early stages of the disease, and treating established disease.

BACKGROUND OF THE INVENTION

Inflammation contributes to pathogenesis of inflammatory diseases, or diseases associated with inflammation, such as autoimmune diseases including rheumatoid arthritis (RA), systemic lupus erythematosus (SLE), multiple sclerosis (MS), and autoimmune hepatitis; degenerative diseases with an inflammatory component such as osteoarthritis (OA), Alzheimer's disease (AD), and macular degeneration; chronic infections such as HIV; metabolic diseases with an inflammatory component such as type II diabetes, metabolic syndrome, and atherosclerosis; and malignant diseases including cancers. Aminoquinolines including hydroxychloroquine (HCQ) are used as anti-inflammatory agents to treat certain inflammatory diseases.

Aminoquinolines are derivatives of quinoline that are most notable for their roles as antimalarial drugs, but they also possess anti-inflammatory properties. Examples of drugs of the aminoquinoline class include, but are not limited to, 4-aminoquinolines, such as amodiaquine, hydroxychloroquine (HCQ), chloroquine; and 8-aminoquinolines, such as primaquine and pamaquine. 4-Aminoquinoline is a form of aminoquinoline with the amino group at the 4-position of the quinoline. A variety of derivatives of 4-aminoquinoline are antimalarial agents, and examples include amodiaquine, chloroquine, and HCQ.

The 4-aminoquinoline HCQ was initially developed as hydroxychloroquine sulfate (HCQ sulfate) for use as an antimalarial drug. Hydroxychloroquine sulfate is sold under the trade names Plaquenil™, Axemal™ (in India), Dolquine™, and Quensyl™, and is also widely used to reduce inflammation in the treatment of systemic lupus erythematosus, rheumatoid arthritis, Sjögren's Syndrome, and porphyria cutanea tarda. HCQ differs from chloroquine by having a hydroxyl group at the end of the side chain: The N-ethyl substituent is beta-hydroxylated. It is available for oral administration as hydroxychloroquine sulfate (Plaquenil), of which 200 mg contains 155 mg hydroxychloroquine base in chiral form. In addition to 155 mg of hydroxychloroquine base, each Plaquenil tablet contains the following inactive ingredients: sulfate ($SO_4$), anhydrous lactose, croscarmellose sodium, glyceryl triacetate, hypromellose, magnesium stearate, microcrystalline cellulose, polydextrose, polyethylene glycol, povidone, sodium lauryl sulfate and titanium dioxide. Hydroxychloroquine sulfate has similar pharmacokinetics to chloroquine phosphate, being quickly absorbed by the gastrointestinal tract and eliminated by the kidney. Cytochrome P450 enzymes (CYP 2D6, 2C8, 3A4, and 3A5) N-desethylate HCQ to N-desethylhydroxychloroquine (Kalia et al. (2007) Dermatologic Therapy 20 (4): 160-174).

The most common adverse effects of HCQ therapy are mild nausea and occasional stomach cramps with mild diarrhea. The most serious adverse effects affect the eye. One of the most serious side effects of chronic HCQ use is ocular and retinal toxicity (Flach. Transactions of the American Ophthalmological Society, 2007, 105: 191-4; discussion 195-7).

Prolonged use of HCQ, chloroquine, or other aminoquinolines is associated with the development of eye toxicity (Marmor et al. Arthritis Care Res. 2010; 62(6):775-84; Levy et al, Incidence of hydroxychloroquine retinopathy in 1,207 patients in a large multicenter outpatient practice. Arthritis Rheumatism 1997, 40(8):1482-6; Mavrikakis et al, The incidence of irreversible retinal toxicity in patients treated with hydroxychloroquine: a reappraisal. Opthalmology, 2003, 110(7):1321-6). The incidence of such toxicity increases markedly with the duration of therapy, with ophthalmoscopically visualized loss of retinal pigmented epithelium in approximately 0.5-1% of HCQ sulfate treated humans after 5 years; and approximately 2% of HCQ sulfate treated humans after 10-15 years. Considerably higher rates of toxicity are observed with chloroquine. Notably, despite the observed rates of retinal toxicity, total rates of physician discontinuation of HCQ for earlier eye problems (including asymptomatic changes noted on ophthalmologic examination) approach 7% of HCQ sulfate treated patients over 5 years (Marmor et al. Rates and predictors of hydroxychloroquine retinal toxicity in patients with rheumatoid arthritis and systemic lupus erythematosus, Arthritis Care Res. 2010; 62(6):775-84).

Toxicity due to HCQ may occur in two distinct areas of the eye: the cornea and the macula. The cornea may become affected (relatively commonly) by an innocuous vortex keratopathy that is characterized by whorl-like corneal epithelial deposits. Changes to the macula (a component of the retina) are more serious and are related to dosage and duration of HCQ use. Advanced retinopathy is characterized by reduction of visual acuity and a "bull's-eye" macular lesion, which is absent in the earlier stages. Bull's eye maculopathy and/or paracentral scotoma are clinical features of HCQ retinopathy.

Macular retinal toxicity is related to the total cumulative dose. People taking 400 mg of HCQ S04 or less per day generally have lower risk of macular retinal toxicity, and the risk increases when a person takes the medication for more than 5 years or takes a cumulative dose of more than 1000 grams, and at a dose of 400 mg/day of HCQ sulfate the cumulative dose of 1000 grams is reached at 7 years of dosing (400 mg/day HCQ sulfate×365 days/year×7 years=1022 grams of HCQ sulfate) (Wolfe and Marmor, Rates and Predictors of Hydroxychloroquine Retinal Toxicity in Patients with Rheumatoid Arthritis and Systemic Lupus Erythematosus, Arthritis Care and Research, 2010, 62(6):775-784; Marmor et al. (2011) Ophthalmology 118

(2): 415-22). The risk of retinal toxicity was found to be 5 times higher after 7 years of usage or 1000 grams of total exposure (Marmor et al. Arthritis Care Res. 2010; 62(6): 775-84). Regular eye screening, even in the absence of visual symptoms, is recommended to begin when either of these risk factors is present (Marmor et al. (2011) Ophthalmology 118 (2): 415-22). In a study of 3,995 patients with rheumatoid arthritis or systemic lupus erythematosus who were treated with HCQ sulfate, eye examinations to monitor for HCQ toxicity were obtained annually in 50.5% of patients and every 6 months in 40.4% of patients (Marmor et al. Arthritis Care Res. 2010; 62(6):775-84).

The exact mechanisms underlying HCQ-induced retinal toxicity, including retinal macular toxicity, are not clear. Studies to date have identified retinal accumulation of HCQ to levels much higher than those observed in other tissues and in the blood. In addition, HCQ binds to melanin in the retinal pigment epithelium (RPE), and such binding may contribute to or prolong HCQ's toxic effects. Some studies have demonstrated that both chloroquine and HCQ are associated with increased lipofuscin formation, a process known to be accelerated by increased lysosomal pH and intra-lysosomal oxidation during degradation of auto-/heterophagocytosed material (Sundelin et al. APMIS [Acta Pathologica, Microbiologica Immunologica Scandinavica]. 2002; 110(6):481-9). Findings suggest that chloroquine blocks attachment of autophagosomes to lysosomes, thereby resulting in the accumulation of lipofuscin and persistence chloroquine and other aminoquinolines in the retinal pigmented epithelial cells (Yoon et al, Induction of lysosomal dilatation, arrested autophagy, and cell death by chloroquine in cultured ARPE-19 cells, Invest Ophthalmol Vis Sci. 2010, 51(11):6030-7). Additionally, because melanin within the RPE has a role in neutralizing oxidative free radicals, it has been suggested that the presence of excessive levels of such free radicals may contribute to the pathogenesis of HCQ-induced retinal toxicity (Sundelin et al. APMIS. 2002; 110(6):481-9).

Retinal toxicity induced by chloroquine and HCQ is characterized by a fine mottling of the macula, arteriolar narrowing, peripheral retinal pigmentation, loss of the foveal reflex and, in advanced cases, by a depigmented macula surrounded by a pigmented ring, a finding termed "bull's-eye maculopathy" (Mecklenburg et al, Toxicol Pathol. 2007; 35(2):252-67). In the early stages of retinal toxicity, patients may notice decreased visual acuity, blurred vision, decreased color and night vision, as well as a paracentral scotoma (Mecklenburg et al, Toxicol Pathol. 2007; 35(2): 252-67). HCQ retinopathy is related to the total cumulative dose and develops slowly, but can progress to a more serious loss of central and peripheral vision for which there is no known treatment (Marmor et al., Arthritis Care Res. 2010; 62(6):775-84).

Current recommendations for screening for chloroquine and HCQ retinopathy are contained in the "2011 AAO Revised Recommendations" described in Marmor et al. (Revised recommendations on screening for chloroquine and hydroxychloroquine retinopathy, Ophthalmology. 2011, 118(2):415-22). The recommendations include performing a baseline examination within the first year of patients starting hydroxychloroquine or chloroquine therapy to serve as a reference point and to rule out pre-existing maculopathy, which frequently contraindicates use of these drugs. Annual screening for eye toxicity is recommended to begin after 5 years, or sooner if there are additional risk factors including cumulative dose >1000 grams of HCQ sulfate, use of a daily dose of HCQ sulfate >400 mg/day (or >6.5 mg/kg HCQ sulfate for lean body weight for short individuals), advanced age, kidney or liver dysfunction, or retinal disease or maculopathy (Marmor et al, Opthamology. 2011, 118(2):415-22).

As described in the "2011 AAO Revised Recommendations" (Revised recommendations on screening for chloroquine and hydroxychloroquine retinopathy, Ophthalmology. 2011, 118(2):415-22), newer objective tests, such as multifocal electroretinogram (mfERG), spectral domain optical coherence tomography (SD-OCT), and fundus autofluorescence (FAF), can be more sensitive than visual field tests. It is now recommended that along with white 10-2 automated field threshold tests, at least one of these procedures be used for routine screening when available. When field tests are performed independently, even the most subtle 10-2 field changes should be taken seriously and are an indication for evaluation by objective testing. Because mfERG testing is an objective test that evaluates function, it may be used in place of visual field tests. Amsler grid testing is no longer recommended. Fundus examinations are advised for documentation, but visible bull's-eye maculopathy is a late change, and the goal of screening is to detect toxicity at an earlier stage. Further, patients should be aware of the risk of toxicity and the rationale for screening (to detect early changes and minimize visual loss, not necessarily to prevent it). The drugs should be stopped if possible when toxicity is detected or strongly suspected (Marmor et al, Ophthalmology. 2011, 118(2):415-22).

Although HCQ and other aminoquinolines have been used to treat inflammatory diseases, as discussed herein, prolonged administration of HCQ and other aminoquinolines is associated with deposition of the aminoquinoline in the retina and the development of retinal toxicity. Accordingly, there is a need for improved pharmaceutical compositions which provide anti-inflammatory activity while exhibiting less retinal accumulation and less retinal toxicity as compared to HCQ and other aminoquinolines.

SUMMARY OF THE INVENTION

In various embodiments, compositions and methods are provided for preventing or treating inflammatory diseases or diseases associated with inflammation. In particular, the compositions and methods of the present invention are suitable for treating various patient populations, and at various stages in the disease process, including in the at-risk period, early stages and established inflammatory diseases, including autoimmune diseases, degenerative inflammatory diseases, metabolic inflammatory diseases, and other inflammatory diseases and diseases associated with inflammation by administration to an individual an effective dose of the aminoquinoline desethylhydroxychloroquine (DHCQ). Treatment of inflammatory disease at an early time point by the compositions and methods of the invention can substantially reduce or prevent disease development, clinical symptoms, or disease progression. In some embodiments treatment is initiated when individuals are at increased risk for development of a disease to prevent development of the disease, to treat early signs or symptoms of disease, or to reverse early signs or symptoms of disease. Individuals who are at increased risk for development of disease may be asymptomatic, may be asymptomatic but have early signs of disease, or may have early symptoms of disease. In other embodiments, treatment is initiated when individuals have early-stage disease to prevent progression of disease, to treat early signs or symptoms of disease, or to reverse early signs or symptoms of disease. When individuals have early-stage disease they have early symptoms or signs of disease, may have intermittent or mild symptoms, or may be asymptomatic and only exhibit signs of disease. In other embodiments, treatment is initiated when individuals have established disease to prevent progression of disease, to treat signs and symptoms of disease, or to reverse signs and symptoms of disease. Administration of the pharmaceutical composition of this invention may continue for an extended period of time, for example over a period of months or years. In some embodiments, treatment with DHCQ is continued for at least about one year. In particular embodiments, treatment with DHCQ is continued for at least about 1 year. In some embodiments, treatment with DHCQ is continued for at least about 7 years. In some embodiments, treatment with DHCQ is continued for at least about 5 years. In some embodiments, treatment with DHCQ is continued for at least about 10 years. In some embodiments, treatment with DHCQ is continued for at least about 15 years. In some embodiments, treatment with DHCQ is continued for at least about 20 years. In some embodiments, treatment with DHCQ is continued for the lifetime of the individual.

In some embodiments, a pharmaceutical composition comprising an effective dose of desethylhydroxychloroquine, e.g. DHCQ, and a pharmaceutically acceptable excipient is provided. In some embodiments, the pharmaceutical formulation comprises, consists, or consists essentially of DHCQ or an equivalent in a daily dose of at least about 50 mg per day (about 0.83 mg/kg/day), about 100 mg per day (about 1.66 mg/kg/day), about 155 mg per day (about 2.58 mg/kg/day), about 200 mg per day (about 3.33 mg/kg/day), about 250 mg per day (about 4.16 mg/kg/day), about 300 mg per day (about 5 mg/kg/day), about 310 mg per day (about 5.16 mg/kg/day), about 350 mg per day (about 5.83 mg/kg/day), about 00 mg per day (about 6.67 mg/kg/day), about 450 mg per day (about 7.5 mg/kg/day), about 465 mg per day (about 7.75 mg/kg/day), about 500 mg per day (about 8.33 mg/kg/day), about 550 mg per day (about 9.16 mg/kg/d), about 600 mg per day (about 10 mg/kg/day), about 620 mg per day (about 10.3 mg/kg/day), about 800 mg per day (about 13.3 mg/kg/day), about 930 mg/kg/day (about 15.5 mg/kg/day), about 1000 mg per day (about 16.67 mg/kg/day), about 1200 mg per day (about 20 mg/kg/day), about 1300 mg per day (about 21.67 mg/kg/day), about 1400 mg per day (about 23.3 mg/kg/day), about 1500 mg per day (about 25 mg/kg/day), or about 1600 mg per day (about 26.67 mg/kg/day).

In some embodiments, the pharmaceutical formulation comprises, consists, or consists essentially of DHCQ or an equivalent in a daily dose from about 50 mg per day (about 0.83 mg/kg/day) to about 200 mg per day (about 3.33 mg/kg/day), about 100 mg per day (about 1.67 mg/kg/day) to about 400 mg per day (about 6.67 mg/kg/day), about 200 mg/per day (about 3.33 mg/kg/day) to about 450 mg per day (about 7.5 mg/kg/day), from about 300 mg per day (about 5 mg/kg/day) to about 550 mg per day (about 9.16 mg/kg/day), from about 400 mg per day (about 6.67 mg/kg/day) to about 600 mg per day (about 10 mg/kg/day), from about 500 mg per day (about 8.33 mg/kg/day) to about 700 mg per day (about 11.67 mg/kg/day), from about 550 mg per day (about 9.16 mg/kg/day) to about 750 mg per day (about 12.5 mg/kg/day), from about 600 mg per day (about 10 mg/kg/day) to about 800 mg per day (about 13.3 mg/kg/day), from about 700 mg per day (about 11.67 mg/kg/day) to about 1000 mg per day (about 16.67 mg/kg/day), from about 800 mg per day (about 13.3 mg/kg/day) to about 1600 mg per day (about 26.67 mg/kg/day), from about 900 mg per day (about 15 mg/kg/day) to about 1200 mg per day (about 20 mg/kg/day), from about 1200 mg per day (about 15 mg/kg/day) to about 1600 mg per day (about 26.67 mg/kg/day), from about 1400 mg per day (about 23.3 mg/kg/day) to about 1600 mg per day (about 26.67 mg/kg/day).

The mg/kg/day dosage used herein and throughout this document is based on an ideal body weight of humans of 60 kg (Marmor et al, Revised Recommendations on Screening for Chloroquine and Hydroxychloroquine Retinopathy, Opthalmology 2011, 118:415-422; Pai et al, The Origin of the "Ideal" Body Weight Equations. The Annals of Pharmacotherapy, 2000, 34 (9): 1066-1069; Walpole et al, BMC Public Health (BMC Public Health 2012, 12:439) 12: 439). In other embodiments, the mg/kg/day dosage is based on an average lean body weight of humans of 60 kg (Mackenzie A H. Dose refinements in long-term therapy of rheumatoid arthritis with antimalarials. Am J Med. 1983, 75(suppl):40-45.; Hume, R. Prediction of lean body mass from height and weight. Journal of clinical pathology, 1966, 19 (4): 389-91. PMC 473290. PMID 5929341; Wolfe and Marmor, Rates and Predictors of Hydroxychloroquine Retinal Toxicity in Patients with Rheumatoid Arthritis and Systemic Lupus Erythematosus, Arthritis Care and Research, 2010, 62(6): 775-784).

Depending on the patient and condition being treated and on the administration route, the DHCQ will generally be administered in dosages of about 50-1600 mg per day (0.83-26.6 mg/kg/g/day). The range is broad since in general the efficacy of a therapeutic effect for different mammals varies widely with doses typically being 20, 30, 40 or even 50 times smaller (per unit body weight) in humans than in the mouse. Similarly the mode of administration can have a large effect on dosage. Thus for example oral dosages in the mouse may be ten times the injection dose in the mouse. As a result, the preferred range for mice is about 2.5 to 150 mg/kg/day, and in some embodiments in mice about 10 to 100 mg/kg/day, while for humans it may be about 0.83-26.6 mg/kg/day, and in some embodiments about 6.67-13.3 mg/kg/day. A typical adult human dosage may be about 400 mg per day, or about 500 mg per day, or about 550 mg per day, or about 600 mg per day, or about 700 mg per day, or about 750 mg per day, or about 800 mg per day, or the amounts described in the daily dosages elsewhere in this application. The total daily dose may be taken in divided two times per day, or three times per day doses. In one embodiment, about 200 mg twice per day (about 400 mg total per day, about 6.67 mg/kg/day), or about 250 mg twice per day (about 500 mg total per day, about 8.33 mg/kg/day), or about 275 mg twice per day (about 550 mg total per day, about 9.16 mg/kg/day), or about 300 mg twice per day (about 600 mg total per day, about 10 mg/kg/day), or about 350 mg twice per day (about 700 mg total per day, about 11.66 mg/kg/day) or about 400 mg twice per day (about 800 mg total per day, about 13.3 mg/kg/day), or in the total dosages described elsewhere in this application. Doses may be taken with the meals.

In some embodiments, treatment may comprise administering a synergistic combination of desethylhydroxychloroquine (DHCQ) with one or more active agents, wherein the synergistic combination comprises, consists, or consists essentially of DHCQ and one or more statins, e.g. atorvastatin, fluvastatin, lovastatin, mevastatin, pitavastatin, pravastatin, rosuvastatin, simvastatin, etc. The active agents of the synergistic combination can be administered separately, or can be co-formulated in a single unit dose (i.e., a "fixed dose combination"). Each or all of the active agents can be formulated in various ways, including without limitation a solid oral dosage form.

In some embodiments a package suitable for use in commerce is provided for treating inflammation according to the methods of the invention, e.g. a pharmaceutical formulation comprising, consisting of, or consisting essentially of DHCQ, optionally in combination with one or more additional agents, e.g. one or more statins as described herein; and associated with said package (e.g., a carton or container), printed instructional and informational material, which may be attached to said carton or to said container enclosed in said carton, or displayed as an integral part of said carton or container, said instructional and informational material stating in words which convey to a reader thereof that the active ingredients, when administered to an individual in the early stages of inflammatory disease, will ameliorate, diminish, actively treat, reverse or prevent any injury, damage or loss of tissue subsequent to early stages of disease. The package comprising a carton and/or container as described herein may conform to all regulatory requirements relating to the sale and use of drugs, including especially instructional and informational material.

In some embodiments the methods of the invention comprise the step of identifying individuals "at-risk" for development of, or in the "early-stages" of, an inflammatory disease. "At risk" for development of an inflammatory disease includes: (1) individuals whom are at increased risk for development of an inflammatory disease, and (2) individuals exhibiting a "pre-clinical" disease state, but do not meet the diagnostic criteria for the inflammatory disease (and thus are not formally considered to have the inflammatory disease).

Individuals "at increased risk" for development (also termed "at-risk" for development) of an inflammatory disease are individuals with a higher likelihood of developing an inflammatory disease or disease associated with inflammation compared to the general population. Such individuals can be identified based on their exhibiting or possessing one or more of the following: a family history of inflammatory disease; the presence of certain genetic variants (genes) or combinations of genetic variants which predispose the individual to such an inflammatory disease; the presence of physical findings, laboratory test results, imaging findings, marker test results (also termed "biomarker" test results) associated with development of the inflammatory disease, or marker test results associated with development of a metabolic disease; the presence of clinical signs related to the inflammatory disease; the presence of certain symptoms related to the inflammatory disease (although the individual is frequently asymptomatic); the presence of markers (also termed "biomarkers") of inflammation; and other findings that indicate an individual has an increased likelihood over the course of their lifetime to develop an inflammatory disease or disease associated with inflammation. Most individuals at increased risk for development of an inflammatory disease or disease associated with inflammation are asymptomatic, and are not experiencing any symptoms related to the disease that they are at an increased risk for developing.

Included, without limitation, in the group of individuals at increased risk of developing an inflammatory disease or a disease associated with inflammation, are individuals exhibiting "a pre-clinical disease state". The pre-disease state may be diagnosed based on developing symptoms, physical findings, laboratory test results, imaging results, and other findings that result in the individual meeting the diagnostic criteria for the inflammatory disease, and thus being formally diagnosed. Individuals with "pre-clinical disease" exhibit findings that suggest that the individual is in the process of developing the inflammatory disease, but do not exhibit findings, including the symptoms, clinical findings, laboratory findings, and/or imaging findings, etc. that are necessary to meet the diagnostic criteria for a formal diagnosis of the inflammatory disease. In some embodiments, individuals exhibiting a pre-clinical disease state possess a genetic variant or a combination of genetic variants that place them at increased risk for development of disease as compared to individuals who do not possess that genetic variant or that combination of genetic variants. In some embodiments, these individuals have laboratory results, or physical findings, or symptoms, or imaging findings that place them at increased risk for development of an inflammatory disease. In some embodiments, individuals with preclinical disease states are asymptomatic. In some embodiments, individuals with pre-clinical disease states exhibit increased or decreased levels of the expression of certain genes, certain proteins, inflammatory markers, metabolic markers, and other markers.

In some embodiments, individuals at increased risk for an inflammatory disease exhibit increased markers of inflammation (also termed "inflammatory markers" or "inflammatory biomarkers"). Examples of molecular markers of inflammation include c-reactive protein (CRP), high-sensitivity CRP (hs-CRP) (or regular CRP), erythrocyte sedimentation rate (ESR), serum amyloid A, serum amyloid P, fibrinogen, cytokines in blood or other biological fluids, a cytokine, an antibody (such as an autoantibody, or an anti-microbial antibody), a DNA sequence, a RNA sequence (for example, mRNA encoding one or more cytokines or other immune molecules), other markers of inflammation, or combinations thereof. The method can include determining the presence of inflammation prior to treatment, for example by detection and analysis of one or more markers of inflammation, where an individual in an early stage of disease showing signs of inflammation is selected for treatment with a formulation of the invention. In some embodiments the treatment ameliorates, diminishes, actively treats, reverses or prevents tissue injury. In some embodiments the inflammatory disease is an autoimmune disease, for example RA, multiple sclerosis, systemic lupus erythematosus, Sjogren's Syndrome, etc. In some embodiments, the marker of inflammation (or inflammatory marker) is a metabolic marker (also termed herein as a "metabolic disease marker"). In some embodiments the disease comprises an inflammatory component contributing to a metabolic disease, for example metabolic syndrome, type II diabetes, insulin resistance, atherosclerosis, etc. In some embodiments the disease is a degenerative disease such as OA, Alzheimer's disease, or macular degeneration.

In some embodiments the marker of inflammation is an abnormal metabolic marker (also termed herein as a "metabolic disease marker"), and the abnormal metabolic marker is selected from the group consisting of a blood pressure of about 140/90 mmHg or more, plasma triglyceride levels of about 1.7 mmol/L or more, high-density lipoprotein cholesterol (HDL-C) levels of about 0.9 mmol/L or less for males and about 1.0 mmol/L or less for females, a microalbuminuria:urinary albumin excretion ratio of about 20 µg/min or more, or an albumin:creatinine ratio of about 30 mg/g or more, a fasting blood glucose greater than about 100 mg/dL, 2 hour post-prandial blood glucose greater than about 200, or a hemoglobin A1c greater than about 6.5 mg/dL. Patients with abnormal metabolic markers are at increased risk for developing an inflammatory disease or disease associated with inflammation.

In some embodiments the methods of the invention comprise the step of identifying and treating individuals at increased risk for development of an inflammatory disease or disease associated with inflammation. These individuals at increased risk for development of an inflammatory disease can have risk factors for disease and/or be in a "pre-clinical" state as described herein, and are sometimes asymptomatic. Treatment with DHCQ alone or synergistic combinations thereof with a statin, as described herein, at this point is exceptionally valuable in preventing development of the inflammatory disease or disease associated with inflammation; however, it is important to prescribe a safe and efficacious therapy that can be tolerated over long periods of time, as is provided by the present invention.

The determination of "early-stage disease" in an individual can comprise analyzing the individual for the presence of at least one marker indicative of the presence of early disease. In some embodiments the method comprises analyzing an individual for the presence of one, two, three, four, or more markers that are predictive for an individual being at increased risk for developing or in the early-stages of an inflammatory disease or disease associated with inflammation. In some embodiments at least one of the marker(s) is an imaging marker, including without limitation: arthroscopy, radiographic imaging, ultrasound imaging, magnetic resonance imaging (MRI), computed tomography (CT), etc. In some embodiments at least one of the marker(s) is a molecular marker of inflammation, where a biological sample is obtained from the individual and analyzed for the presence of a molecule, e.g. high-sensitivity C-reactive protein (or regular CRP), erythrocyte sedimentation rate, serum amyloid A, serum amyloid P, fibrinogen, a cytokine, antibody (autoantibody or anti-microbial antibody), cartilage component, protease, RNA molecule (for example, mRNA encoding one or more cytokines or other immune molecules), etc. and compared to a control or reference value, wherein altered level of the molecular marker is indicative of early disease. In some embodiments, early-stage disease is defined by the presence of symptoms for less than about 6 months. In some embodiments, early-stage disease is defined by being formally diagnosed with the inflammatory disease for less than about 6 months. In some embodiments, early-stage disease is associated with no symptoms. In some embodiments, early-stage disease is associated with mild symptoms. In some embodiments, early-stage disease is associated with intermittent symptoms, such as symptoms occurring only once every couple years, or symptoms occurring once every couple months, or symptoms occurring once every couple days, or symptoms occurring for only part of each day. Such individuals identified as having early-stage inflammatory disease can then be treated, advantageously, with DHCQ, or with a synergistic combination of DHCQ and a statin, as described herein.

In certain embodiments, this invention is directed to the treatment of individuals with established inflammatory disease or disease associated with inflammation. The inflammatory disease is diagnosed based on an individual exhibiting symptoms, signs, clinical features, laboratory test results, imaging test results, biomarker results, and other findings that enable a physician to formally diagnose that individual with the inflammatory disease. In some embodiments, established inflammatory disease is an inflammatory disease for which an individual has had a formal diagnosis of the disease made by a physician for longer than 6 months. In established inflammatory disease, the signs or symptoms of disease may be more severe as compared to, for example, the symptoms for an individual diagnosed with early-stage inflammatory disease. In established inflammatory disease, the disease process may cause tissue or organ damage. As described herein, in certain embodiments, determination of inflammation in an individual with established disease can comprise analyzing the individual for the presence of at least one marker indicative of the presence of inflammation.

Determination of inflammation in an individual at risk for, with early-stage, or with established disease can comprise analyzing the individual for the presence of at least one marker indicative of the presence of inflammation or metabolic abnormalities. Markers of inflammation include molecular markers, metabolic markers, clinical markers and imaging markers. In some embodiments, the method comprises analyzing an individual for the presence of one, two, three, four, or more markers of inflammation that are diagnostic for inflammation, which can be systemic or localized inflammation. In some embodiments at least one of the marker(s) of inflammation is an imaging marker, including without limitation radiographic imaging, ultrasound imaging, magnetic resonance imaging (MRI), computed tomography (CT), etc. In some embodiments at least one of the marker(s) of inflammation is a molecular marker, where a biological sample is obtained from the individual and analyzed for the presence of a molecule, e.g. high-sensitivity CRP (or regular CRP), cytokine, serum amyloid A, serum amyloid P, fibrinogen, antibody (autoantibody or anti-microbial antibody), cartilage component, protease, RNA sequence (for example, mRNA encoding one or more cytokines or other immune molecules), etc. and compared to a control or reference value, wherein altered level of the molecular marker is indicative of inflammation. In some embodiments, the marker of inflammation is an abnormal clinical marker. Examples of abnormal clinical markers of inflammation include swelling on physical examination, tenderness on physical examination, and combinations thereof. In some embodiments the marker indicative of inflammation indicates the presence of local inflammation, i.e. inflammation present at the affected joint, in the central nervous system, or in another tissue, organ or site within the body. In some embodiments, the marker of inflammation is an abnormal metabolic marker, and the abnormal metabolic marker is selected from the group consisting of a blood pressure of about 140/90 mmHg or more, plasma triglyceride levels of about 1.7 mmol/L or more, high-density lipoprotein cholesterol (HDL-C) levels of about 0.9 mmol/L or less for males and about 1.0 mmol/L or less for females, a microalbuminuria:urinary albumin excretion ratio of about 20 μg/min or more, or an albumin:creatinine ratio of about 30 mg/g or more, a fasting blood glucose greater than about 100 mg/dL, 2 hour post-prandial blood glucose greater than about 200, or a hemoglobin A1c greater than about 6.5 mg/dL. The measurement or detection of an abnormal inflammatory or metabolic marker in an individual is predictive for that individual being at increased risk of developing, in the pre-clinical phase of, in the early-stages of, or having an established inflammatory disease or disease associated with inflammation.

BRIEF DESCRIPTION OF THE DRAWINGS

FIG. 6 is a chart of various parameters related to the progression of mouse osteoarthritis, including "cartilage degeneration score", "osteophyte score", and "synovitis score", comparing treatment with vehicle, HCQ, and DHCQ.

FIG. 20 is a chart comparing cartilage degeneration scores, osteophyte scores, and synovitis scores for subjects treated with atorvastatin, HCQ, DHCQ, BDCQ, DCQ, atorvastatin+HCQ, atorvastatin+DHCQ, and atorvastatin+BDCQ, as compared to subjects treated with vehicle (control).

FIG. 21 is a chart comparing cartilage degeneration scores, osteophyte scores, and synovitis scores for mice treated with HCQ+atorvastatin as compared to HCQ, HCQ+atorvastatin as compared to atorvastatin, DHCQ+atorvastatin as compared to DHCQ, and DCHQ+atorvastatin as compared to atorvastatin.

DETAILED DESCRIPTION OF THE EMBODIMENTS

Figure 1:
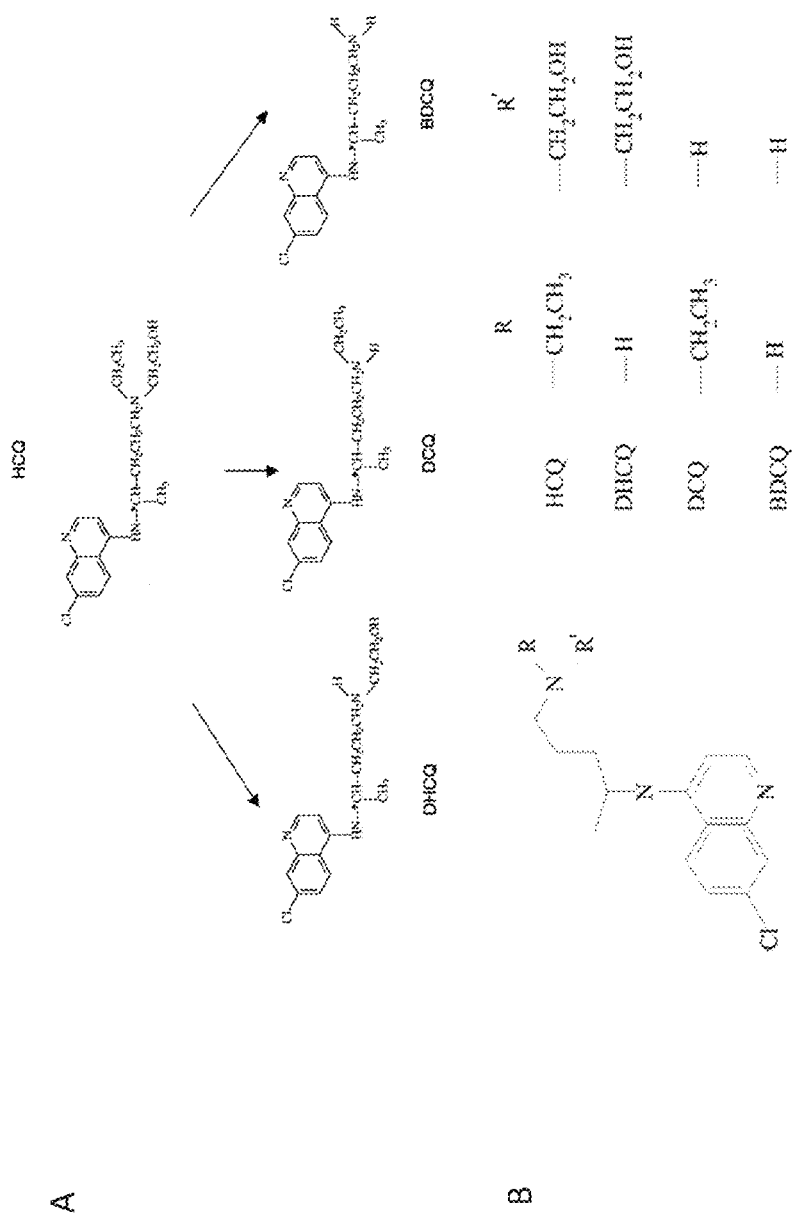
FIG. 1 provides the chemical structures of hydroxychloroquine (HCQ), desethylhydroxychloroquine (DHCQ), desethylchloroquine (DCQ), and bisdesethylchloroquine (BDCQ).

Many diseases have an underlying inflammatory component that contributes to disease initiation and/or progression. Thus, the spectrum of inflammatory diseases and diseases associated with inflammation is broad and includes autoimmune diseases such rheumatoid arthritis (RA), systemic lupus erythematosus (SLE), multiple sclerosis (MS), and autoimmune hepatitis; degenerative diseases such as osteoarthritis (OA), Alzheimer's disease (AD), and macular degeneration; chronic infections such as human immunodeficiency virus (HIV), chronic hepatitis C virus (HCV) infection, chronic hepatitis B virus (HBV), chronic cytomegalovirus (CMV) infection, tuberculosis (TB) infection, as well as other chronic viral and bacterial infections; metabolic diseases including type II diabetes, metabolic syndrome, non-alcoholic steatohepatitis (NASH), and alcoholic steatohepatitis; cardiovascular diseases such as atherosclerosis; cancers which can arise from and induce inflammation; as well as other diseases with an inflammatory component.

Additional inflammatory diseases and diseases associated with inflammation include but are not limited to acne vulgaris, acne congloblata, acne fulminans, asthma, celiac disease, chronic prostatitis, ulcerative colitis, microscopic colitis, collagenous colitis, Crohn's disease, atopic dermatitis, diverticulitis, glomerulonephritis, interstitial cystitis, viral hepatitis including but not limited to hepatitis B and hepatitis C, interstitial cystitis, irritable bowel syndrome, reperfusion Injury, sarcoidosis, amyloidosis, and transplant rejection including but not limited to heart, lung, kidney, pancreas, bone marrow, stem cell, skin, corneal, and islet cell transplants. Additional inflammatory diseases and diseases associated with inflammation include cancers and pre-cancerous states and the associated inflammatory responses. Additional inflammatory diseases and diseases associated with inflammation include infectious diseases associated with inflammation which include but are not limited to chronic infection with human immunodeficiency virus (HIV), hepatitis C virus (HCV), hepatitis B virus (HBV), syphilis, rickettsial diseases, lyme disease, bacterial cellulitis, chronic fungal infection, ehrlichiosis, HHV-6, Herpes simplex virus 1 and 2, stongyloidiasis, Epstein barr virus, cytomegalovirus, mycoplasma infection, Creutzfeldt- Jacob disease, oncocerciasis, nocardia, Whipples disease, mycobacterial disease, tinea infection, and alphaviruses including but not limited to chikungunya, ross river virus, or other alphaviruses. Additional inflammatory diseases and diseases associated with inflammation include but are not limited to anti-phosholipid syndrome, Hashimoto's thyroiditis, Dequervains thyroiditis, Graves thyroiditis, adrenalitis, type I diabetes mellitus, hypophysitis, pemphigus vulgaris, bullous pemphigoid, Eaton Lambert syndrome, myasthenia gravis, Addison's disease, ankylosing spondylitis, alopecia aureate, autoimmune hemolytic anemia, immune thrombocytopenic purpura, autoimmune hepatitis, Behcets disease, cardiomyopathy, chronic fatigue syndrome, chronic inflammatory demyelinating polyneuropathy, autoimmune inner ear disease, cicatricial pemphigoid, Dego's Disease, dermatomyositis/juvenile dermatomyositis, polymyositis, inclusion body myositis, Guillain-Barre syndrome, Meniere's Disease, mixed connective tissue disease, pernicious anemia vasculitis, polychondritis, polyglandular autoimmune syndrome, polymyalgia rheumatic, primary biliary cirrhosis, psoriasis, psoriatic arthritis, Raynaud's phenomenon, Reiter's syndrome, reactive arthritis, rheumatic fever, scleroderma, Sjogren's syndrome, stiff-man syndrome, Takayasu arteritis, temporal arteritis/giant cell arteritis, polyartereitis nodosa, uveitis, vitiligo, autoimmune Wilsons disease, bleeding disorders due to autoreactivity against clotting factors, chronic urticaria, vasculitis including but not limited to granulomatosus with polyangiitis, eosinophilic granulomatosis with polyangiits, microscopic polyangiits, henoch schonlien purpura, hypersensitivity vasculitis, hypocomplementemic urticarial vasculitis, polyarteritis nodosa.

In one classification, an inflammatory disease is considered a disease which exhibits clinical manifestations (abnormal clinical markers) such as visible inflammation including pain, swelling, warmth, and redness. This classification of inflammatory disease would include, but certainly not be limited to, RA, SLE, NAFLD, NASH, MS, metabolic syndrome, type II diabetes, atherosclerosis, cardiovascular disease and OA.

Diseases associated with inflammation have in their underlying pathology a focal, multifocal, or systemic inflammatory process, but which are manifested as organ or system dysfunction without apparent clinical inflammation. In this classification, hyperlipidemia and insulin resistance are referred to as diseases associated with inflammation. Conditions such as hyperlipidemia can be considered a disease herein because it is a metabolic abnormality associated potential pathology. Likewise, insulin resistance can be considered a disease herein because it is a metabolic abnormality associated potential pathology. Hyperlipidemia and insulin resistance can thus be considered diseases associated with inflammation. It should be noted that a significant proportion of patients with hyperlipidemia, insulin resistance, with or without frank NASH or its precursor NAFLD, have what is known as the metabolic syndrome. The metabolic syndrome refers to a group of factors, including hypertension, obesity, hyperlipidemia, and insulin resistance (manifesting as frank diabetes or high fasting blood glucose or impaired glucose tolerance), that raises the risk of developing heart disease, diabetes, or other health problems; (Grundy et al, Circulation. 2004; 109:433-438). The metabolic syndrome has been associated with inflammation both as an effect of the syndrome and as a contributor to its initiation, progression, and ultimate pathogenesis. (Romeo G R et al, Arterioscler Thromb Vasc Biol. 2012 32(8):1771-6; de Luca C et al, FEBS Lett. 2008 582(1):97-105; Ma K et al, Diabetes Metab Res Rev. 2012 28(5):388-94). In part, this is due to macrophage accumulation in obese adipose tissue, where they produce TNF and other inflammatory cytokines in response to stimulation with saturated fatty acids and circulating lipopolysaccharide (LPS) (Johnson et al, Cell 2013. 152(4):673-84; Bhargava P et al, Biochem J. 2012 442(2):253-62). Moreover, TNF inhibition can abrogate insulin resistance (Johnson et al, Cell 2013. 152(4): 673-84). However, the risks of long term TNF inhibition are significant and require injection therapy. The identification of a safe and effective agent to ameliorate adipose macrophage activation and cytokine production would be beneficial. As many anti-inflammatory and immunosuppressive agents are themselves associated with adverse metabolic risk (i.e. hypertension, insulin resistance, hyperlipidemia, and/or hepatic steatosis), if such an agent had a favorable effect on metabolic profile this would be highly advantageous.

A variety of therapeutics exist for inflammatory diseases, and examples include: non-steroidal anti-inflammatory drugs (NSAIDs) such as ibuprofen, Naprosyn and aspirin; steroids such as prednisone and methylprednisolone; small molecule drugs that inhibit immune cell proliferation including methotrexate, sulfasalazine, imuran, cyclophosphamide; small molecule kinase inhibitors including imatinib, tofacitinib, and others; antibody therapeutics targeting TNF (adalimumab, infliximab, etc), IL-6 (tocilizumab which targets the IL-6 receptor), IL-1 (canakinumab), IL-17 (secukinumab), IL-12p40 (ustekinumab), and others; non-antibody biological therapeutics including CTLA4-Ig, etanercept, and IL-1 receptor antagonist (anakinura). It is well known that these drugs exhibit differential therapeutic activity against different inflammatory diseases. For example, anti-TNF antibodies effectively treat rheumatoid arthritis (RA), psoriasis and ankylosing spondylitis; but are not effective at treating systemic lupus erythematosus (SLE) and vasculitis; exacerbate multiple sclerosis; are appropriate to use in RA and psoriasis patients with chronic hepatitis C virus infection, but are contraindicated in patients with chronic hepatitis B virus infection due to their propensity to trigger hepatitis B viral replication and exacerbation of the infection. In contrast, ustekinumab effectively treats psoriasis, but does not provide benefit in rheumatoid arthritis or multiple sclerosis. In contrast, methotrexate exhibits efficacy in rheumatoid arthritis and psoriasis, but does not treat SLE or Crohn's disease. As a result, it is not possible to predict for which inflammatory diseases or diseases associated with inflammation a particular anti-inflammatory drug will provide a benefit. Not only does the clinical effectiveness of anti-inflammatory drugs vary widely depending upon the indication, but also particular anti-inflammatory drugs can exacerbate other symptoms of the disease. Accordingly, each anti-inflammatory drug candidate must be empirically tested and demonstrated to provide efficacy for treating a specific inflammatory disease in order to establish the candidate anti-inflammatory drug as a safe, appropriate, and efficacious treatment for that particular inflammatory disease.

Rheumatoid Arthritis (RA) is a chronic syndrome characterized usually by symmetric inflammation of the peripheral joints, potentially resulting in progressive destruction of articular and periarticular structures, with or without generalized manifestations (Firestein (2003) Nature 423(6937): 356-61; McInnes and Schett. (2011) N Engl J Med. 365(23): 2205-19). The cause is unknown. A genetic predisposition has been identified, and, in some populations, localized to a pentapeptide in the HLA-DR beta1 locus of class II histocompatibility genes. Environmental factors may also play a role. For example, cigarette smoking places individuals possessing HLA-DR4 containing the "shared epitope" polymorphism at approximately 10-20 fold increased risk of developing RA. Cigarette smoking is thought to induce anti-citrullinated protein antibody (ACPA) responses, which are measured using the commercial cyclic-citrullinated peptide (CCP) assay (Klareskog et al. (2006) Arthritis Rheum. 54(1):38-46). In addition, periodontitis and infection with *P. gingivalis* might also play a role in the initiation of autoimmune responses that result in development of RA (Rutger and Persson. 2012, J Oral Microbiol. 4). Immunologic changes may be initiated by multiple factors. About 0.6% of all populations are affected, women two to three times more often than men. Onset may be at any age, most often between 25 and 50 yr.

Prominent immunologic abnormalities that may be important in pathogenesis include antibodies and immune complexes found in joint fluid cells and in vasculitis. Plasma cells produce antibodies that contribute to these complexes. Lymphocytes that infiltrate the synovial tissue are primarily T helper cells, which can produce pro-inflammatory cytokines. Macrophages and their cytokines (e.g., tumor necrosis factor, granulocyte-macrophage colony-stimulating factor) are also abundant in diseased synovium. Increased adhesion molecules contribute to inflammatory cell emigration and retention in the synovial tissue. Increased macrophage-derived lining cells are prominent along with some lymphocytes and vascular changes in early disease.

In chronically affected joints, the normally delicate synovium develops many villous folds and thickens because of increased numbers and size of synovial lining cells and colonization by lymphocytes and plasma cells. The lining cells produce various materials, including collagenase and stromelysin, which can contribute to cartilage destruction; interleukin-1, which stimulates lymphocyte proliferation; and prostaglandins. The infiltrating cells, initially perivenular but later forming lymphoid follicles with germinal centers, synthesize interleukin-2, other cytokines, RF, and other immunoglobulins. Fibrin deposition, fibrosis, and necrosis also are present. Hyperplastic synovial tissue (pannus) may erode cartilage, subchondral bone, articular capsule, and ligaments. PMNs are not prominent in the synovium but often predominate in the synovial fluid.

Onset is usually insidious, with progressive joint involvement, but may be abrupt, with simultaneous inflammation in multiple joints. Tenderness in nearly all inflamed joints is the most sensitive physical finding. Synovial thickening, the most specific physical finding, eventually occurs in most involved joints. Symmetric involvement of small hand joints (especially proximal interphalangeal and metacarpophalangeal), foot joints (metatarsophalangeal), wrists, elbows, and ankles is typical, but initial manifestations may occur in any joint. RA is characterized by the development of focal bone erosions through degradation and remodeling of bone at the joint margins and in subchondral bone of patients with RA. A hallmark of a subset of RA is the development of autoantibodies, including rheumatoid factors (RF) and anti-citrullinated protein antibodies (ACPA). RF, antibodies to human γ-globulin, are present in about 70% of patients with RA. However, RF, often in low titers, occurs in patients with other diseases, including other connective tissue diseases such as systemic lupus erythematous, granulomatous diseases, chronic infections such as viral hepatitis, subacute bacterial endocarditis, and tuberculosis, and cancers. Low RF titers can also occur in a small percentage of the general population, and more commonly in the elderly. Another disease indicator is the presence of ACPA, which are measured using the clinical anti-CCP (cyclic citrullinated peptide) antibody test. Anti-CCP antibodies are approximately 60% sensitive and 95% specific for the diagnosis of RA, and like RF, predict a worse prognosis.

Systemic lupus erythematosus (SLE) is a systemic autoimmune disease characterized by malar rashes, oral ulcers, photosensitivity, serositis, seizures, low white blood cell counts, low platelet counts, seizures, a positive anti-nuclear antibody (ANA) test, and other positive autoantibodies. SLE is an autoimmune disease characterized by polyclonal B cell activation, which results in a variety of anti-protein and non-protein autoantibodies that result in immune complexes and inflammation which contributes to tissue damage (see, e.g., Kotzin et al., 1996, Cell 85:303-06 for a review of the disease). SLE has a variable course characterized by exacerbations and remissions and is difficult to study. For example, some patients may demonstrate predominantly skin rash and joint pain, show spontaneous remissions, and require little medication. The other end of the spectrum includes patients who demonstrate severe and progressive kidney involvement (glomerulonephritis and cerebritis) that requires therapy with high doses of steroids and cytotoxic drugs such as cyclophosphamide. Hydroxychloroquine slows SLE progression, and is a mainstay therapeutic for the management of SLE.

Multiple sclerosis (MS) is a debilitating, inflammatory, neurological illness characterized by demyelination of the central nervous system. The disease primarily affects young adults with a higher incidence in females. Symptoms of the disease include fatigue, numbness, tremor, tingling, dysesthesias, visual disturbances, dizziness, cognitive impairment, urological dysfunction, decreased mobility, and depression. Four types classify the clinical patterns of the disease: relapsing-remitting, secondary progressive, primary-progressive and progressive-relapsing (S. L. Hauser and D. E. Goodkin, Multiple Sclerosis and Other Demyelinating Diseases in Harrison's Principles of Internal Medicine 14th Edition, vol. 2, Mc Graw-Hill, 1998, pp. 2409-19).

Inflammatory bowel diseases, include Crohn's disease and ulcerative colitis, involve autoimmune attack of the bowel. These diseases cause chronic diarrhea, frequently bloody, as well as symptoms of colonic dysfunction.

Systemic sclerosis (SSc, or scleroderma) is an autoimmune disease characterized by fibrosis of the skin and internal organs and widespread vasculopathy. Patients with SSc are classified according to the extent of cutaneous sclerosis: patients with limited SSc have skin thickening of the face, neck, and distal extremities, while those with diffuse SSc have involvement of the trunk, abdomen, and proximal extremities as well. Internal organ involvement tends to occur earlier in the course of disease in patients with diffuse compared with limited disease (Laing et al. (1997) Arthritis. Rheum. 40:734-42). The majority of patients with diffuse SSc who develop severe internal organ involvement will do so within the first three years after diagnosis at the same time the skin becomes progressively fibrotic (Steen and Medsger (2000) Arthritis Rheum. 43:2437-44.). Common manifestations of diffuse SSc that are responsible for substantial morbidity and mortality include interstitial lung disease (ILD), Raynaud's phenomenon and digital ulcerations, pulmonary arterial hypertension (PAH) (Trad et al. (2006) Arthritis. Rheum. 54:184-91.), musculoskeletal symptoms, and heart and kidney involvement (Ostojic and Damjanov (2006) Clin. Rheumatol. 25:453-7). Current therapies focus on treating specific symptoms, but disease-modifying agents targeting the underlying pathogenesis are lacking.

Autoimmune hepatitis is a disease in which the body's immune system attacks liver cells. This immune response causes inflammation of the liver, also called hepatitis. Researchers think a genetic factor may make some people more susceptible to autoimmune diseases. About 70 percent of those with autoimmune hepatitis are female. The disease is usually quite serious and, if not treated, gets worse over time. Autoimmune hepatitis is typically chronic, meaning it can last for years, and can lead to cirrhosis—scarring and hardening—of the liver. Eventually, liver failure can result.

Four subtypes of autoimmune hepatitis are recognized, but the clinical utility of distinguishing subtypes is limited. (1) positive ANA and SMA, elevated immunoglobulin G (classic form, responds well to low dose steroids); (2) positive LKM-1 (typically female children and teenagers; disease can be severe), LKM-2 or LKM-3; (3) positive antibodies against soluble liver antigen (this group behaves like group 1) (anti-SLA, anti-LP), and (4) no autoantibodies detected (~20%) (of debatable validity/importance) (Krawitt et al. Autoimmune hepatitis. New England Journal of Medicine, 1996 334 (14): 897-903).

Many degenerative diseases have an underlying inflammatory component, and examples of such degenerative diseases include osteoarthritis (OA), Alzheimer's disease (AD), and macular degeneration.

Osteoarthritis (OA) affects nearly 27 million people in the United States, accounting for 25% of visits to primary care physicians, and half of all NSAID prescriptions. Rheumatoid arthritis (RA) is an autoimmune synovitis that affects approximately 0.6% of the world population. OA is a chronic arthropathy characterized by disruption and potential loss of joint cartilage along with other joint changes, including bone remodeling that may include bone hypertrophy (osteophyte formation), subchondral sclerosis, and formation of subchondral cysts. OA is viewed as failure of the synovial joint (Abramson et al, Arthritis Res Ther. 2009; 11(3):227; Krasnokutsky et al, Osteoarthritis Cartilage. 2008; 16 Suppl 3:S1-3; Brandt et al, Rheum Dis Clin North Am. 2008 August; 34(3):531-59). OA results in the degradation of joints, including articular cartilage and subchondral bone, resulting in mechanical abnormalities and impaired joint function. Symptoms may include joint pain, tenderness, stiffness, sometimes an effusion, and impaired joint function. A variety of causes can initiate processes leading to loss of cartilage.

OA may begin with joint damage from trauma to the joint; mechanical injury to the meniscus, articular cartilage, a joint ligament, or another joint structure; defects in cartilage matrix components; and the like. Mechanical stress on joints may underlie the development of OA in many individuals, with many and varied sources of mechanical stress, including misalignments of bones caused by congenital or pathogenic causes; mechanical injury; overweight; loss of strength in muscles supporting joints; and impairment of peripheral nerves, leading to sudden or dyscoordinated movements that overstress joints.

Articular cartilage comprises chondrocytes that generate and are surrounded by extracellular matrix. In synovial joints there are at least two movable bony surfaces that surrounded by the synovial membrane, which secretes synovial fluid, a transparent alkaline viscid fluid which fills the joint cavity, and articular cartilage, which is interposed between the articulating bony surfaces. The earliest gross pathologic finding in osteoarthritis is softening of the articular cartilage in habitually loaded areas of the joint surface. This softening or swelling of the articular cartilage is frequently accompanied by loss of proteoglycans from the cartilage matrix. With progression of osteoarthritis the integrity of the cartilage surface is lost and the articular cartilage thins, with vertical clefts extending into the depth of the cartilage in a process called fibrillation. Joint motion may cause fibrillated cartilage to shed segments that expose the bone underneath (subchondral bone). The subchondral bone is remodeled in OA, including the development of subchondral sclerosis, development of subchondral cysts, and the formation of ectopic bone termed osteophytes. Subchondral cysts also develop which may be filled with synovial fluid. At the joint margins osteophytes (bone spurs) form. The remodeling of subchondral bone increases the mechanical strain and stresses on both the overlying articular cartilage and subchondral bone, leading to further damage of both the cartilage and subchondral bone.

The tissue damage stimulates chondrocytes to attempt repair, which increases production of proteoglycans and collagen. However, efforts at repair also stimulate the enzymes that degrade cartilage, as well as inflammatory cytokines, which are normally present in small amounts. Inflammatory mediators trigger an inflammatory cycle that further stimulates the chondrocytes and synovial lining cells, eventually breaking down the cartilage. Chondrocytes undergo programmed cell death (apoptosis).

OA is characterized pathologically by low-grade infiltration of inflammatory cells including inflammatory cells, primarily macrophages, but also B cells and T cells. These cells, again primarily macrophages, are capable of producing inflammatory cytokines and MMPs in the OA joint. However, when stimulated by inflammatory cytokines including IL-1 and TNF, primary cells within the joint, including synovial fibroblasts and chondrocytes, are capable of producing further cytokines including IL-6 as well as multiple MMPs.

OA should be suspected in patients with gradual onset of symptoms and signs, particularly in older adults, usually beginning with one or a few joints. Pain can be the earliest symptom, sometimes described as a deep ache. Pain is usually worsened by weight bearing and relieved by rest but can eventually become constant. Stiffness follows awakening or inactivity. If OA is suspected, plain x-rays should be taken of the most symptomatic joints. X-rays generally reveal marginal osteophytes, narrowing of the joint space, increased density of the subchondral bone, subchondral cyst formation, bony remodeling, and joint effusions (which are considered abnormal imaging markers). Standing x-rays of knees are more sensitive in detecting joint space narrowing. Magnetic resonance imaging (MRI) can be used to detect cartilage degeneration, and several MRI-based based scoring systems have been developed to characterize the severity of OA (Hunter et al, P M R. 2012 May; 4(5 Suppl):568-74).

OA commonly affects the hands, feet, spine, and the large weight bearing joints, such as the hips and knees, although in theory, any joint in the body can be affected. As OA progresses, the affected joints appear larger, are stiff and painful, and usually feel better with gentle use but worse with excessive or prolonged use. Treatment generally involves a combination of exercise, lifestyle modification, and analgesics. If pain becomes debilitating, joint replacement surgery may be used to improve the quality of life.

Among the agents proposed to provide for disease modification, such as doxycycline (presumably though its action at an MMP inhibitor), bisphosphonates (presumably aimed at inhibiting osteoclast activation) and licofelone (by inhibiting the cyclooxygenase and lipoxegenase pathways), none have demonstrated robust chondroprotection as defined by slowing of cartilage breakdown. Among the agents that have demonstrated partial efficacy in control of pain associated with OA are analgesics such as acetaminophen and anti-inflammatories including non-steroidal anti-inflammatory agents (NSAIDs), opiates, intraarticular corticosteroids, and hyaluronic acid derivatives injected into the joint. These agents have not been demonstrated to prevent cartilage loss or slow the loss of joint function.

Given the slow progression seen in OA, the need to take an agent for lengthy periods of time necessitates a high degree of safety. Thus, there is need for therapeutic options that provide disease modifying functional activity and a safety profile that allows an extended duration of therapy.

Murine models of OA include induction of OA through destabilization of the medial meniscus (DMM) or medial meniscectomy (MM). Histological analysis of stifle (knee) joint articular cartilage at serial time points after medial meniscectomy in the MM model. Approximately 2-6 months following surgical induction, mice are sacrificed and histologic sections stained with toluidine-blue, Safranin-O, and/or hematoxylin and eosin (H&E) to determine the level of cartilage loss (or level of cartilage degeneration, or "OA score"), as well as the degree of osteophyte formation, and the degree of synovial inflammation (termed synovitis).

Alzheimer's disease (AD) is the most common neurodegenerative disease in the population (Cummings et al., Neurology 51, S2-17; discussion S65-7, 1998). AD affects approximately 10% of people over age 65 and almost 50% of people over age 85. It is estimated that by the year 2025, about 22 million individuals will be afflicted with AD. AD is characterized by a slowly progressive dementia. The definitive diagnosis of AD is made if the triad of dementia, neurofibrillary tangles, and senile plaques are found post-mortem. Senile plaques are invariably found in the brains of patients with Alzheimer disease. The principal constituent of senile plaques is amyloid beta protein (Aβ) (Iwatsubo et al., Neuron 13:45-53, 1994) (Lippa et al., Lancet 352:1117-1118, 1998). Aβ is a 42 amino acid peptide that is derived from the amyloid precursor protein (APP), which is a transmembrane glycoprotein with a variety of physiologic roles, including cell proliferation, adhesion, cell signaling, and neurite outgrowth (Sinha et al., Ann N Y Acad Sci 920:206-8, 2000). APP is normally cleaved within the Aβ domain to generate a secreted fragment. However, alternative processing leads to the cleavage of APP to generate soluble Aβ that can accumulate within senile plaques. Currently available drugs are central cholinesterase inhibitors aimed at increasing the concentration of postsynaptic acetylcholine in the brain (Farlow and Evans, Neurology 51, S36-44; discussion S65-7, 1998); (Hake, Cleve Clin J Med 68, 608-9:613-4, 616, 2001). These drugs provide minimal clinical benefit in only a few cognitive parameters.

Macular degeneration can be of the wet type related to retinal neovascularization and vascular leak but is more commonly of the dry type also known as age-related macular degeneration (AMD). AMD is a chronic disease associated with loss of central vision, blurred vision, and ultimately blindness. Though the causes and risk factors for AMD are multifactorial, activation of innate immunity involving complement activation as well as cytokine production by macrophage and microglia has been implicated in development of AMD. Anti-inflammatory therapy including corticosteroids, non-steroidal anti-inflammatory agents, methotrexate, rapamycin, and biologic agents including TNF inhibitors and complement inhibitors have been suggested to slow progression of AMD (Wang et al, 2011. Eye (2011)25, 127-139). However, because these treatments are not curative and AMD is a chronic, non-fatal disease, their use is limited by risk of toxicity.

The HIV virus is the cause of AIDS, a nearly uniformly fatal disease without treatment. However, the advent of highly active antiretroviral therapy (HAART) has resulted in the change of HIV from fatal disease to a chronic condition. With the prolonged lifespan of individuals with HIV, it has been noted that despite viral suppression and even immune reconstitution as measured by peripheral CD4 T cell counts, there is still an increased morbidity and mortality which is primary due to metabolic derangements and increased cardiovascular risk. The exact source of this immune activation not been determined, but the continued low grade replication of HIV virus and activation of the endosomal TLR7 receptor as well as activation of CD8 T cell response have been implicated. Additionally, irreversible damage to the immune cells of gut mucosa result in increased bacterial and endotoxin translocation and thus systemic inflammation (Deeks 2011 Annu Rev Med. 62:141-55). As expected, levels of cytokines including TNF, IL-6 as well as other inflammatory markers such as CRP as well as coagulation markers such as D-dimer are notably elevated despite successful HAART therapy (Deeks 2011. Annu Rev Med. 62:141-55).

Other chronic infections can also cause persistent inflammation. Such infections include chronic hepatitis B virus infection, chronic hepatitis C virus infection, cytomegalovirus (CMV) infection, herpes simplex virus (HSV) infection, Epstein Barr virus (EBV) infection, chronic pseudomonas infection, chronic *Staphylococcus* infection, and other chronic viral, bacterial, fungal, parasitic, and other infections.

Non-alcoholic fatty liver disease (NAFLD) and non-alcoholic steatohepatitis (NASH) are conditions associated with fatty infiltration of the liver. NAFLD is one cause of a fatty liver, occurring when fat is deposited (steatosis) in the liver not due to excessive alcohol use (Clark J M et al, J. American Medical Association 289 (22): 3000-4, 2003). It can be related to insulin resistance and the metabolic syndrome and may respond to treatments originally developed for other insulin-resistant states (e.g. diabetes mellitus type 2) such as weight loss, metformin and thiazolidinediones.

NAFLD is considered to cover a spectrum of disease activity. This spectrum begins as fatty accumulation in the liver (hepatic steatosis). A liver can remain fatty without disturbing liver function, but by varying mechanisms and possible insults to the liver may also progress to become NASH, a state in which steatosis is combined with inflammation and fibrosis. NASH is a progressive disease: over a 10-year period, up to 20% of patients with NASH will develop cirrhosis of the liver, and 10% will suffer death related to liver disease. NASH is the most extreme form of NAFLD, and is regarded as a major cause of cirrhosis of the liver of unknown cause (McCulough A J et al, Clinics in Liver Disease 8 (3): 521-33, 2004).

Common findings in NAFLD and NASH are elevated liver enzymes and a liver ultrasound showing steatosis. An ultrasound may also be used to exclude gallstone problems (cholelithiasis). A liver biopsy (tissue examination) is the only test widely accepted as definitively distinguishing NASH from other forms of liver disease and can be used to assess the severity of the inflammation and resultant fibrosis (Adams L A et al, Postgrad Med J 82(967):315-22, 2006). Non-invasive diagnostic tests have been developed, such as FibroTest, that estimates liver fibrosis, and SteatoTest, that estimates steatosis, however their use has not been widely adopted (McCulough A J et al, Clinics in Liver Disease 8 (3): 521-33, 2004).

Although fatty infiltration alone does not cause liver damage, when it is accompanied by an inflammatory reaction it can lead to fibrosis and liver cirrhosis and ultimately hepatic failure. The inflammation in NASH is characterized by infiltration of the liver by macrophages and lymphocytes, as well as alterations in the liver's macrophage-like Kupfer cell population (Tilg, et al, 2010. Hepatology. 52(5):1836-46). Inflammatory cytokines, particularly TNF, are central to the pathology of NASH. The source of TNF is unclear: it may be peripheral, i.e., inflammatory adipose tissue, or local, i.e., innate immune cells activated by portal-derived endotoxin or by free fatty acid. The endotoxin-responsive TLR4 receptor has been shown to be critical to disease in a mouse model of NASH (Tsukumo et al, Diabetes 2007. 56(8):1986-98).

A large number of treatments for NAFLD and NASH have been studied. Treatment approaches include: (i) Treatment of nutrition and excessive body weight, (ii) weight loss, (iii) weight loss surgery, (iv) insulin sensitizers including metformin and thiazolidinediones, (v) Vitamin E can improve some symptoms, (vi) statins have been shown to improve liver biochemistry and histology in patients with NAFLD; McCulough A J et al, supra; Chalasani N. et al, Gastroenterology 142(7):1592-1609, 2012).

Type II diabetes mellitus and metabolic syndrome. Type II diabetes mellitus is characterized by insulin resistance and hyperglycemia, which in turn can cause retinopathy, nephropathy, neuropathy, or other morbidities. Additionally, diabetes is a well-known risk factor for atherosclerotic cardiovascular disease. Metabolic syndrome refers to a group of factors, including hypertension, obesity, hyperlipidemia, and insulin resistance (manifesting as frank diabetes or high fasting blood glucose or impaired glucose tolerance), that raises the risk of developing heart disease, diabetes, or other health problems; (Grundy et al, Circulation. 2004; 109:433-438). There is a well-characterized progression from normal metabolic status to a state of impaired fasting glucose (IFG: fasting glucose levels greater than 100 mg/dL) or to a state of impaired glucose tolerance (IGT: two-hour glucose levels of 140 to 199 mg/dL after a 75 gram oral glucose challenge). Both IFG and IGT are considered pre-diabetic states, with over 50% of subjects with IFG progressing to frank type II diabetes within, on average, three years (Nichols, Diabetes Care 2007. (2): 228-233). The insulin resistance is caused, at least in part, by chronic low-grade inflammation (Romeo G R et al, Arterioscler Thromb Vasc Biol. 2012 32(8):1771-6; de Luca C et al, FEBS Lett. 2008 582(1):97-105; Ma K et al, Diabetes Metab Res Rev. 2012 28(5):388-94). Macrophages accumulate in obese adipose tissue, where they produce TNF and other inflammatory cytokines in response to stimulation with saturated fatty acids and circulating lipopolysaccharide (LPS) (Johnson et al, Cell 2013. 152(4): 673-84; Bhargava P et al, Biochem J. 2012 442(2):253-62). Moreover, TNF inhibition can abrogate insulin resistance (Johnson et al, Cell 2013. 152(4):673-84).

Hyperlipidemia is considered a disease herein because it is a metabolic abnormality associated potential pathology. Hyperlipidemia involves abnormally elevated levels of any or all lipids and/or lipoproteins in the blood. The term lipids includes cholesterol and triglycerides. There are many different types of lipid (also called lipoproteins). Blood tests can measure the levels of lipoproteins. The standard lipid blood tests include a measurement of total cholesterol, LDL (low density lipoproteins) and HDL (high density lipoproteins), and triglycerides.

Total cholesterol—A high total cholesterol level can increase an individual's risk of cardiovascular disease. However, decisions about when to treat high cholesterol are usually based upon the level of LDL or HDL cholesterol, rather than the level of total cholesterol. A total cholesterol level of less than 200 mg/dL (5.17 mmol/L) is normal. A total cholesterol level of 200 to 239 mg/dL (5.17 to 6.18 mmol/L) is borderline high. A total cholesterol level greater than or equal to 240 mg/dL (6.21 mmol/L) is high. The total cholesterol level can be measured any time of day. It is not necessary to fast (avoid eating for 12 hours) before testing.

LDL cholesterol—The low density lipoprotein (LDL) cholesterol (sometimes called "bad cholesterol") is a more accurate predictor of cardiovascular disease than total cholesterol. Higher LDL cholesterol levels increase your risk of cardiovascular disease.

Most healthcare providers prefer to measure LDL cholesterol after you have not eaten (fasted) for 12 to 14 hours. A test to measure LDL in people who have not fasted is also available, although the results may differ slightly. Increased LDL cholesterol is associated with increased risk of heart attack and stroke. In general, LDL levels fall into these categories: Less than 100 mg/dL Optimal; 100 to 129 mg/dL Near or above optimal; 130 to 159 mg/dL Borderline high; 160 to 189 mg/dL High; 190 mg/dL and above Very high.

The Framingham Risk Score is a gender-specific algorithm used to estimate the 10-year cardiovascular risk, including the risk of cardiovascular events, myocardial infarction, stroke, heart failure, and other events, of an individual—such cardiovascular diseases represent an inflammatory disease and/or diseases associated with inflammation. The Framingham Risk Score was first developed based on data obtained from the Framingham Heart Study, to estimate the 10-year risk of developing coronary heart disease (Wilson et al, Prediction of coronary heart disease using risk factor categories. 1998 Circulation 97 (18): 1837-1847; D'Agostino et al, General cardiovascular risk profile for use in primary care: the Framingham Heart Study 2008. Circulation 117 (6): 743-753). The Framingham risk score is based on gender and gender-specific formulas that incorporate age, total cholesterol level, cigarette smoking history, HCL cholesterol level, and systolic blood pressure.

Atherosclerosis and atherosclerotic cardiovascular disease are diseases of the arterial wall. They are characterized by accumulation of fatty materials in the arterial wall, resulting in development of fatty plaques, which may rupture and cause vascular occlusion and ischemia. If such vascular occlusion and ischemia occur in a coronary artery, myocardial infarction may result. The atherosclerotic lesion comprises a highly inflammatory milieu characterized by the accumulation of inflammatory cells, including macrophages and to a lesser extent T and B cells, and the production of high levels of inflammatory cytokines, chemokines, and MMPs (Libby et al, Nature 2011. 473(7347):3170-25). Atherosclerosis may also be associated with low-grade systemic inflammation, as evidenced by high levels of high-sensitivity CRP (hsCRP) in the blood, an abnormality that can be partially countered by treatment with the drug rosuvastatin (Libby et al, Nature 2011. 473(7347):3170-25).

Hydroxychloroquine (HCQ) can be a potent anti-inflammatory agent used for treating inflammatory diseases. However, the use of HCQ in such therapies is limited due to the significant risk of retinal toxicity. Thus vigilant ophthalmologic monitoring coupled with dose reduction or even avoidance of HCQ is recommended, particularly for those at increased risk for retinal toxicity. Individuals at increased risk for retinal toxicity include those who have taken HCQ for longer than five years; have other risk factors, such as a high body fat level, concomitant kidney or liver disease or concomitant retinal disease; are older than 60 years of age; or are particularly diminutive in size and/or body mass. The population of patients with concomitant retinal disease, or who are at significant risk for development of concomitant retinal disease includes the rapidly growing population of patients with type II diabetes and the associated metabolic syndrome. As the prevalence of diabetes is currently over 10% in most parts of the United States, and is approaching similar levels in other developed countries, this places a significant proportion of the population at increased risk of HCQ-mediated retinal toxicity. Notably, rates of type II diabetes are further increased among patients with inflammatory diseases for which HCQ is currently indicated, including rheumatoid arthritis and systemic lupus (Dubreil H, Rheumatology (2014) 53 (2): 346-352.) Another inflammatory condition not previously treated (nor suggested to be treated) with HCQ is non-alcoholic steatohepatitis (NASH). This is an inflammatory condition associated with fatty infiltration of the liver and most commonly associated with concomitant presence of type II diabetes and the associated metabolic syndrome. In fact, it is estimated that 86% of patient with type II diabetes have NASH with nearly the same proportion of NASH patients having type II diabetes (Verderese J P, Expert Rev Gastroenterol Hepatol. 2013 July; 7(5):405-7.) Thus, the majority of patients with NASH have type II diabetes and are at increased risk for retinal toxicity in general, which is a contraindication for HCQ therapy. Accordingly, there is a need for improved therapies for such patients, with decreased retinal toxicity.

The metabolites of hydroxychloroquine (HCQ) include desethylhydroxychloroquine (DHCQ), desethylchloroquine (DCQ), and bisdesethylchloroquine (BDCQ); their chemical structures are presented in FIG. 1. Desethylhydroxychloroquine (DHCQ) is assigned CAS 4298-15-1; and also referred to as cletoquine; DESETHYL HYDROXY CHLOROQUINE.

HCQ increases lysosomal pH in antigen-presenting cells, and this is believed to be a primary mechanism by which it exerts anti-inflammatory effects and alters toll-like receptor (TLR) activity (Waller et al. Medical pharmacology and therapeutics (2nd ed.). p. 370). HCQ inhibits TLRs on plasmacytoid dendritic cells, macrophage and other cells. Activation of TLR 9, a TLR that recognizes DNA-containing immune complexes, leads to the production of interferon and causes the dendritic cells to mature and present antigen to T cells. HCQ, by decreasing TLR 9 signaling, reduces the activation of dendritic cells and hence the inflammatory process.

As described herein, desethylhydroxychloroquine (DHCQ) exhibits similar, and in various cases superior (FIGS. 2-9, 19-21) activity in treating or preventing inflammatory diseases compared to HCQ treatment. Further, it was unexpected and surprising that only the DHCQ metabolite of HCQ exhibited potent efficacy in preventing and treating inflammatory diseases and diseases associated with inflammation, while the BDCQ and DCQ metabolites of HCQ did not provide activity in treating inflammatory diseases and diseases associate with inflammation (FIGS. 1, 2, 3, 9, 19 and 20). In addition to unexpectedly exhibiting efficacy in treating inflammatory disease, DHCQ also unexpectedly and surprisingly exhibits levels of efficacy superior to that of HCQ in treating metabolic abnormalities, specifically in reducing hyperglycemia, reducing serum lipids, and treating metabolism-induced inflammatory disease.

Figure 11:
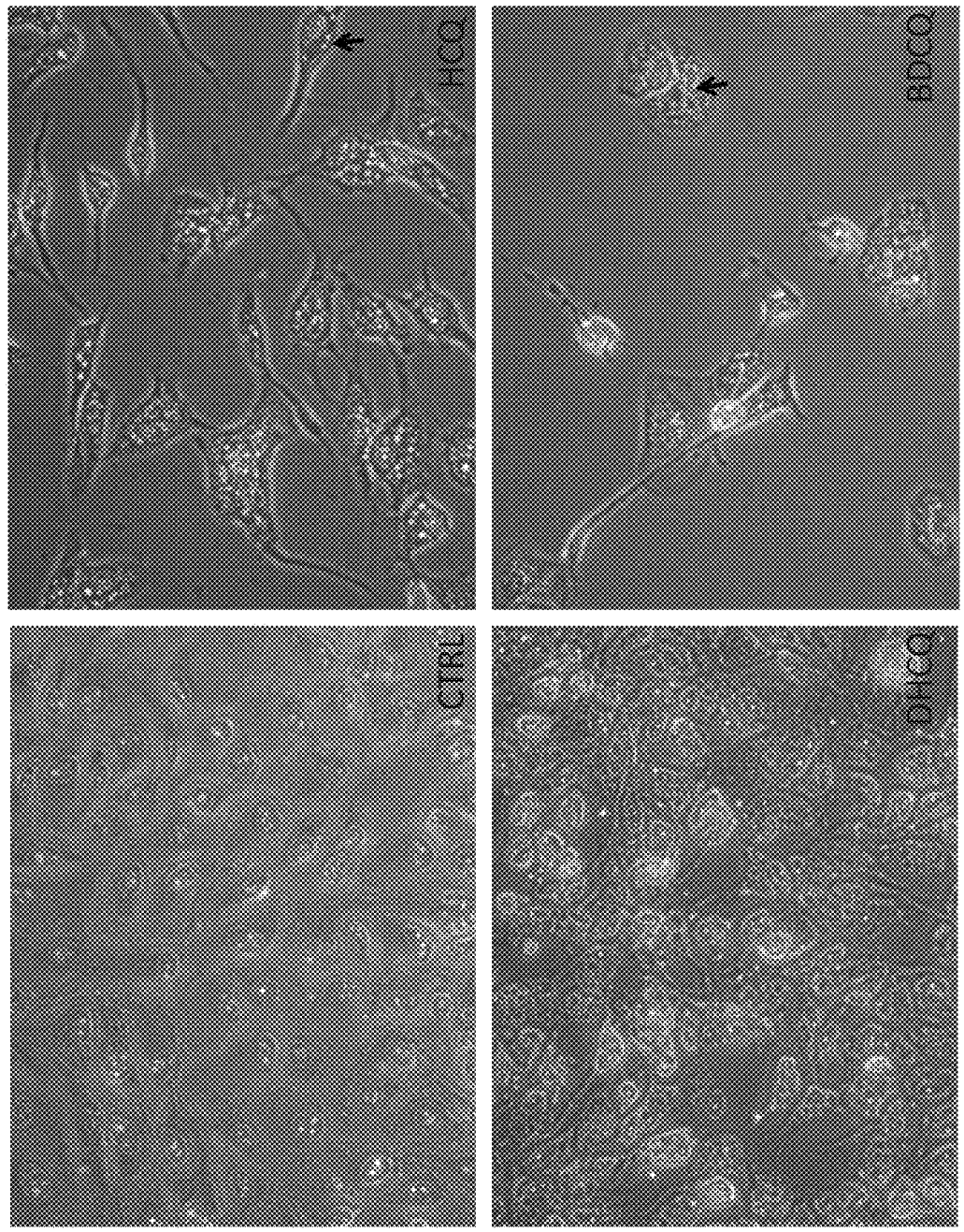
FIG. 11 shows micrographs of in vitro cultured pigmented retinal epithelial cells, comparing exposure to vehicle (control, CTRL), HCQ, DHCQ, and BDCQ for 24 hours.
Figure 12:
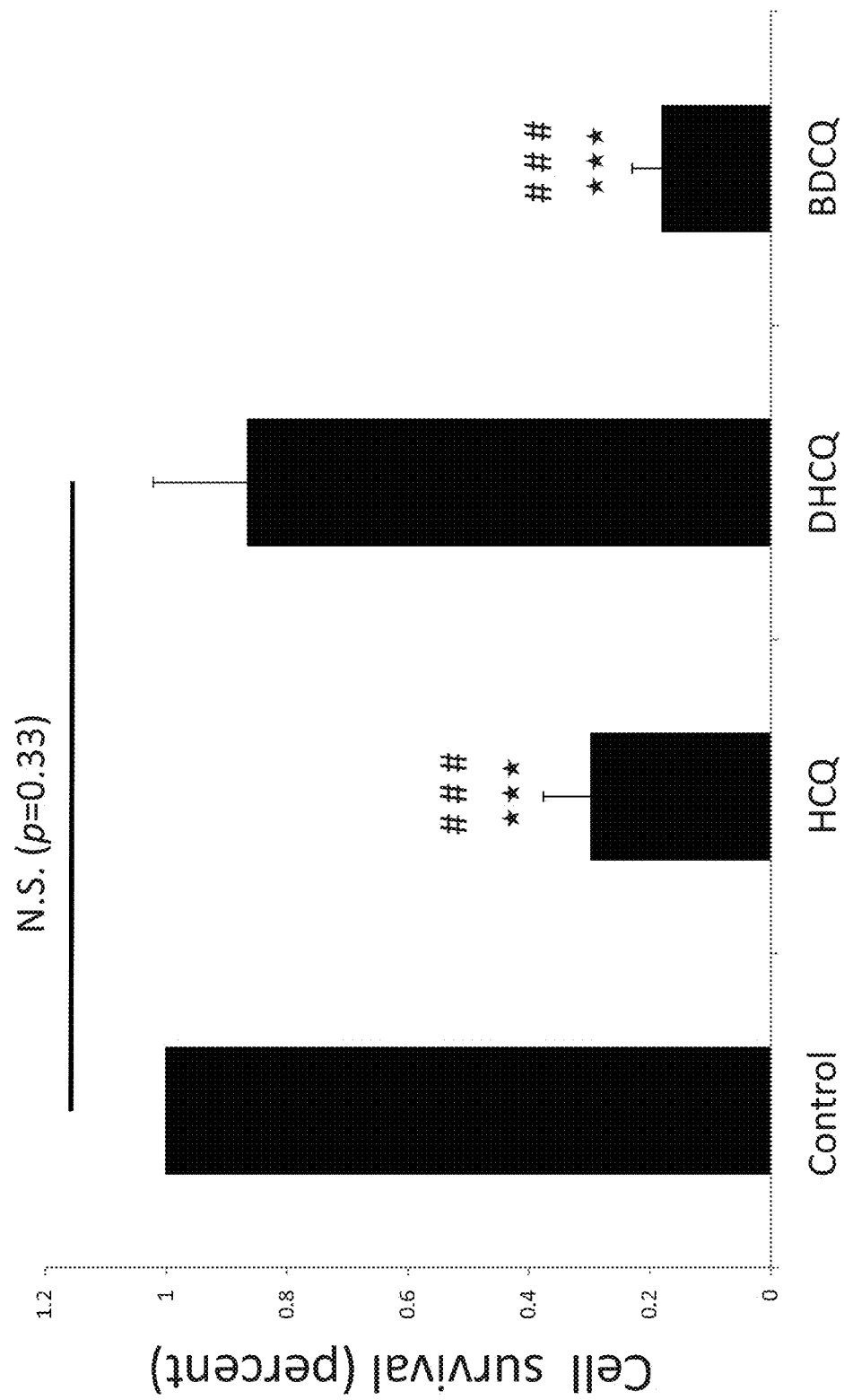
FIG. 12 is a graph comparing percentages of pigmented retinal cell survival, comparing exposure to vehicle, HCQ, DHCQ, and BDCQ.

Despite both DHCQ and HCQ both exhibiting activity in preventing and treating inflammatory diseases and diseases associated with inflammation, DHCQ exhibits significantly reduced retinal accumulation as well as significantly reduced toxicity to retinal cells as compared to the retinal accumulation and toxicity observed for HCQ. The reduced retinal cell toxicity in DHCQ is unexpected and surprising since only treatment with the DHCQ metabolite of HCQ, and not treatment with the BDCQ metabolite of HCQ, provided reduced retinal toxicity (FIGS. 11-12). Further, the reduced retinal cell toxicity by DHCQ is unexpected and surprising since only the DHCQ metabolite of HCQ, and not the BDCQ metabolite of HCQ, provided reduced retinal cell toxicity (FIGS. 11-12). In addition, only the DHCQ, and not the BDCQ and DCQ metabolites of HCQ, exhibited anti-inflammatory efficacy (FIGS. 2, 3, 9, 19 and 20).

Compositions and methods are provided for preventing or treating inflammatory diseases or diseases associated with inflammation, including autoimmune diseases, degenerative diseases, metabolic diseases, and other inflammatory diseases, by administration to an individual in need thereof an effective dose of the aminoquinoline desethylhydroxychloroquine (DHCQ). In further embodiments, the compositions and methods provided herein are suitable for treating low-grade inflammation or ameliorating inflammation or treating diseases associated with inflammation or treating metabolic abnormalities associated with diseases associated with inflammation. A benefit of the methods of the present invention is the ability to deliver a dose of an agent that is effective in treating inflammation while sparing the individual from retinal accumulation and toxicity found with hydroxychloroquine (HCQ) treatment. Reduced monitoring of retinal toxicity during treatment can be a feature of treatment with DHCQ compared to HCQ treatment. Treatment with DHCQ can be initiated earlier in the disease process, and can be maintained for more extended periods of time compared to conventional treatment methods and agents.

In some embodiments the present invention provides compositions of DHCQ or pharmaceutically acceptable salts or esters thereof; or a combination DHCQ or pharmaceutically acceptable salts or esters thereof and one or more second agent from a different drug class, for example a drug that exerts distinct but overlapping mediatory effects, which compositions are utilized to treat an inflammatory disease.

Recent clinical observations in humans demonstrated that taking conventional doses of HCQ (with 400 mg/day being a common dose), the incidence of retinal toxicity increases markedly with the duration of therapy and occurs in approximately 1% of HCQ treated humans after 5 years of treatment, and approximately 2% of HCQ treated humans after 10-15 years of treatment (Marmor et al. Arthritis Care Res. 2010; 62(6):775-84; Levy et al, Incidence of hydroxychloroquine retinopathy in 1,207 patients in a large multicenter outpatient practice. Arthritis Rheumatism 1997, 40(8):1482-6; Mavrikakis et al, The incidence of irreversible retinal toxicity in patients treated with hydroxychloroquine: a reappraisal. Opthalmology, 2003, 110(7):1321-6). Notably, despite the observed rates of retinal toxicity, total rates of physician discontinuation of HCQ for earlier eye problems (including asymptomatic changes noted on ophthalmologic examination) approach 7% of treated patients over 5 years (Marmor et al. Rates and predictors of hydroxychloroquine retinal toxicity in patients with rheumatoid arthritis and systemic lupus erythematosus, Arthritis Care Res. 2010; 62(6):775-84).

The present data demonstrates that DHCQ surprisingly exhibits significantly decreased retinal accumulation as well as significantly decreased retinal toxicity both in vivo and in vitro (see FIGS. 11-18), at dosage levels which provide clinical efficacy similar to that of conventional treatments with HCQ. The estimated rate of retinal toxicity for long-term treatment with DHCQ is less than 50% of the currently reported rate for HCQ when used at a similar effective cumulative dose and over a similar time period. More specifically, as compared to the rates of retinal toxicity described by Marmor et al. for treatment with HCQ (Ophthalmology. 2011 February; 118(2):415-22), given a similar level of therapeutic activity and time period of dosing for both HCQ and DHCQ, DHCQ is estimated to provide less than 50% of retinal toxicity as compared to that with HCQ dosing. Thus, in patient populations analogous to that described by the American College of Opthamolology and Marmor et al (Ophthalmology. 2011 February; 118(2):415-22) where the retinal toxicity rate approach 1% after 5 years, DHCQ therapy is estimated to reduce the retinal toxicity to less that 0.5% of treated individuals. Further, given conventional assumptions that retinal screening is justified as rates of toxicity approach 1%, the reduced cumulative rates of retinal toxicity associated with DHCQ therapy will substantially reduce the need for retinal toxicity screening to a single screening at 5 and 10 years, or entirely negate the need for screening.

In the description that follows, a number of terms conventionally used in the field of treating inflammation are utilized extensively. In order to provide a clear and consistent understanding of the specification and claims, and the scope to be given to such terms, the following definitions are provided.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

All publications, patents, and patent applications mentioned in this specification are herein incorporated by reference in their entirety for all purposes to the same extent as if each individual publication, patent, or patent application was specifically and individually indicated to be incorporated by reference.

Inflammatory diseases are diseases that involve inflammation. The presence of inflammation can be detected by a variety of approaches, including clinical history, physical examination, laboratory testing, histologic analysis of tissue, analysis of biomarkers, and imaging. Clinical features and physical exam markers of inflammation include swelling, effusions, edema, redness, warmth, pain, or associated pathologically with the influx of inflammatory cells or production of inflammatory mediators. Laboratory testing and/or histologic markers are abnormal when increased numbers of inflammatory cells are demonstrated. Markers of inflammation can include a molecular marker(s), and examples of a molecular marker(s) include C-reactive protein, a cytokine, an antibody, a DNA sequence, an RNA sequence, a cartilage marker, a metabolic marker, a bone marker, or combinations thereof. Imaging can reveal findings including enhancement of tissues, edema and swelling of tissues, and other findings indicative of inflammation. Examples of imaging markers of inflammation can include imaging markers measured using magnetic resonance imaging, ultrasound, computed tomography, angiography, and combinations thereof.

The presence of low-grade inflammation is characterized by an elevation(s) in the local or systemic concentrations of cytokines such as TNF-α, IL-6, and c-reactive protein (CRP), and occurs in adiposity, osteoarthritis, Alzheimer's disease, type II diabetes, metabolic syndrome, coronary artery disease, nonalcoholic fatty liver disease (NAFLD), non-alcoholic steatohepatitis, and many chronic and degenerative diseases. Low-grade inflammation is manifest by inflammation present at a level below the "high-grade" inflammation detected in active autoimmune diseases (such as active rheumatoid arthritis, psoriasis, Crohn's disease, systemic lupus erythematous, autoimmune hepatitis, and other autoimmune states) and in certain viral and bacterial infections during which humans experience clinical symptoms (such as influenza virus infection, *Staphylococcus aureus* infection, and other infections).

The reduction or amelioration of inflammation is indicated by dissipation of inflammation, a reduction in number of inflammatory cells or in levels of inflammatory mediators as evidenced by symptomatic relief (including but not limited to pain relief), radiographic changes, biochemical changes, pathologic/histologic changes, decreased progression of such markers of inflammation, decreased development of findings indicative of tissue or organ damage, decreased development of symptoms or signs of disease, or decreased development of disease.

A symptom is a departure from normal function or feeling which is noticed by an individual, indicating the presence of disease or abnormality. A symptom is subjective, observed by the individual patient, and cannot be measured directly.

A sign of disease or a medical sign (also termed marker(s) herein) is an objective indication of some medical fact or characteristic that may be detected during a physical examination, by an in vivo examination of a patient, by a laboratory test, by a radiographic or other imaging test, or by another. Signs or markers may have no meaning to the patient, and may even go unnoticed, but may be meaningful and significant to the healthcare provider in assisting the diagnosis of medical condition(s) responsible for the patient's symptoms. Examples of abnormal markers or signs include elevated blood pressure (greater than about 140 mmHg systolic and/or 90 mmHg diastolic), cholesterol (LDL greater than about 140 mg/dL, triglycerides greater than about 200 mg/dL, or HDL less than about 40 mg/dL), a clubbing of the fingers (which may be a sign of lung disease, or many other things), *arcus senilis*, loss of proteoglycans in the cartilage, increased blood glucose, increased levels of certain markers of liver inflammation, elevated levels of acute phase proteins include ESR greater than about 20, hsCRP greater than about 0.75 mg/L, and other findings. Signs are any indication of a medical condition that can be objectively observed (i.e., by someone other than the patient), whereas a symptom is merely any manifestation of a condition that is apparent to the patient (i.e., something consciously affecting the patient). From this definition, it can be said that an asymptomatic patient is uninhibited by a disease. However, a doctor may discover the signs of hypertension in an asymptomatic patient who does not experience "disease", and the sign indicates a pre-clinical or early-stage disease state that poses a hazard to the patient.

Administration of a drug or other chemical entity to an animal, human or other mammal includes administration via any route including but not limited to oral, intradermal, intramuscular, intraperitoneal, or intravenous.

A pharmaceutical formulation is a composition comprising different chemical substances including but not limited to active drugs, excipients, etc. which are combined and formulated to produce a final medicinal product for the treatment of humans or other organisms.

A sterile formulation is a formulation substantially free of living germs or microorganisms.

A therapeutically effective amount is that mass of an active drug in a formulation, and the frequency of administration of a formulation, that results in the prevention of the development of symptoms, prevention of development of markers or signs of a disease, prevention of the development of tissue or organ damage, prevention of the progression of a disease, reduction in the severity of a disease, or treatment of disease symptoms as defined above.

Dose range for each individual agent is the range of the mass of active drug in, and frequency of administration of, a formulation which results in the prevention of the development of symptoms, prevention of the development of a disease, prevention of development of abnormal markers or signs of a disease, prevention of the development of tissue or organ damage, prevention of the progression of a disease, reduction in the severity of a disease, or treatment of disease symptoms as defined above.

Regimen means dose, frequency of administration, for example twice-per day, daily, weekly, bi-weekly etc., and duration of treatment, for example one day, several days, one week, several weeks, one month, several months, one year, several years, etc.

A loading dose is a large initial dose of a substance or series of such doses given to more rapidly achieve a therapeutic concentration in the body. A loading dose can be higher or lower than the maintenance dose. In some instances, therapy is initiated at a loading dose for days, weeks or months in order to rapidly achieve therapeutic levels of the drug or other chemical entity in tissue, and then the dose is lowered to the long-term maintenance dose. In some cases, an initial low dose is used for a brief period of time to tolerize and accommodate the patient to the drug (e.g. about 200 mg per day for 1 week), followed by a loading dose (e.g. about 800 mg/day for 12 weeks), followed by the maintenance dose (about 400 mg/day). For hydroxychloroquine sulfate and chloroquine phosphate, the standard dose of 400 mg/day can take 4-6 months to achieve therapeutic tissue levels. Therefore, some physicians use loading doses of hydroxychloroquine sulfate or chloroquine phosphate, for example a dose of at least about 600 mg/day (about 10 mg/kg/day), at least about 800 mg/day (about 13.3 mg/kg/day), at least about 1000 mg/day (about 16.67 mg/kg/day), and up to about 1200 mg/day (about 20 mg/kg/d), and up to about 1600 mg/day (about 26.7 mg/kg/day) for 1-16 weeks to more rapidly achieve therapeutic levels in the tissues where it is needed for activity. Desethylhydroxychloroquine (DHCQ) is expected to also accumulate slowly in tissues, such that using, for example, loading doses of at least about 600 mg/day (about 10 mg/kg/day), at least about 800 mg/day (about 13.33 mg/kg/day), at least about 1000 mg/day (about 16.67 mg/kg/day), and up to about 1200 mg/day (about 15 mg/kg/d), up to about 1400 mg/day (about 23.33 mg/kg/day), up to about 1600 mg/day (about 26.6 mg/kg/day), for 1-24 weeks, and preferably for 1-16 weeks may also prove therapeutically beneficial when treating with DHCQ. Loading doses of HCQ for treatment of inflammatory disease are discussed in Furst et al. (Arthritis Rheum. 1999 February; 42(2):357-65. PMID: 10025931).

Unit doses (also called dosage forms) are essentially pharmaceutical products in the form in which they are marketed for use, typically involving a mixture of active drug components and nondrug components (excipients), along with other non-reusable material that may not be considered either ingredient or packaging (such as a capsule shell, for example). Depending on the context, multi(ple) unit dose can refer to distinct drug products packaged together, or to a single drug product containing multiple drugs and/or doses. The term dosage form can also sometimes refer only to the chemical formulation of a drug product's constituent drug substance(s) and any blends involved.

A dose pack is a premeasured amount of drug to be dispensed to a patient in a set or variable dose and in a package including but not limited to a blister pack or other series of container for the purpose of facilitating a dose regimen. A dose pack can be used to facilitate delivery of an initial and/or loading dose to an individual, followed by a maintenance dose.

An excipient is generally a pharmacologically inactive substance formulated with the active pharmaceutical ingredient ("API") of a medication. Excipients are commonly used to bulk up formulations that contain potent active ingredients (thus often referred to as "bulking agents," "fillers," or "diluents"), to allow convenient and accurate dispensation of a drug substance when producing a dosage form. They also can serve various therapeutic-enhancing purposes, such as facilitating drug absorption or solubility, or other pharmacokinetic considerations.

A "marker of inflammation" (also referred to herein as biomarkers of inflammation) is an objectively measured characteristic that reflects the presence of inflammation in a pre-disease state, or disease state including but not limited to molecular, biochemical, imaging, or gross physical measurements. As used herein, "markers of inflammation" include inflammatory markers, metabolic markers, imaging markers, biochemical markers, genetic markers, proteomic markers, gene expression markers, and other markers that can be used to assess inflammation within an individual. The measurement of abnormal markers in an individual identifies that individual as being at increased risk for development of, in the pre-clinical phases of, in the early-stages of, or having an established, inflammatory disease or disease associated with inflammation.

Molecular marker(s) of inflammation (also referred to herein as a "biomarker" or "biomarkers of inflammation") are molecules obtained from tissue (e.g., blood) samples of a patient which indicate the presence of inflammation. Nonlimiting example of such markers can include, for example, C-reactive protein, a cytokine, an antibody, a DNA sequence, an RNA sequence, a cartilage marker, a metabolic marker, a bone marker, or combinations thereof. Molecular markers of inflammation include biochemical markers.

Imaging marker(s) of inflammation (also referred to herein as an "imaging marker" or "imaging biomarkers") are markers that measure or otherwise determine the presence of inflammation through use of an imaging modality, including but not limited to ultrasound, radiography, computerized tomography, magnetic resonance imaging, or nuclear medical scanning.

Biochemical marker(s) (also referred to herein as a "molecular marker") are biologic substances that are measured in blood or other tissue as a biomarker. Biological biomarkers of interest include without limitation proteins, nucleic acids, metabolites, fatty acids, peptides, and the like.

"Inflammatory markers" (also referred to herein as an "inflammatory biomarkers") are biomarkers indicating an inflamed state. Inflammatory biomarkers of interest include without limitation cytokines, chemokines, high sensitivity C-reactive protein (hs-CRP), erythrocyte sedimentation rate (ESR), expression of mRNA encoding inflammatory mediators, inflammatory cells, imaging biomarkers demonstrating inflammation, and other markers indicative of inflammation.

A reference range is defined as the set of values within which 95 percent of the normal population falls. It typically refers to the value or level of a marker (as termed herein as a "marker" or "biomarker", and examples of such markers include but are not limited to inflammatory markers, metabolic markers, imaging markers, biochemical markers, clinical markers, radiographic markers, and other biomarkers. If the value or level of a marker in an individual patient is outside the set of values or levels within which 95 percent of the normal population falls, then the marker is considered to exhibit an abnormal level in that patient (e.g. that patient is determined to have an "abnormal marker"). In some embodiments, if the value or level of an inflammatory marker in an individual patient is outside the set of values or levels within which 95 percent of the normal population falls, then the inflammatory marker is considered to exhibit an abnormal level in that patient (e.g. that patient is determined to have an "abnormal inflammatory marker"). In some embodiments, if the value or level of a metabolic marker (also termed a "metabolic disease marker") in an individual patient is outside the set of values or levels within which 95 percent of the normal population falls, then the metabolic marker is considered to exhibit an abnormal level in that patient (e.g. that patient is determined to have an "abnormal metabolic marker"). In some embodiments, if the result of an imaging marker in an individual patient is outside the range of variation of the same imaging marker observed within 95 percent of the normal population, then the imaging marker is considered to exhibit an abnormal result (e.g. it is an "abnormal imaging marker"). In some embodiments, if the result of a clinical marker in an individual patient is outside the range of variation of the same clinical marker observed within 95 percent of the normal population, then the clinical marker is considered to exhibit an abnormal result (e.g. it is an "abnormal clinical marker"). The measurement of abnormal markers in an individual identifies that individual as being at increased risk for development of, in the pre-clinical phases of, in the early-stages of, or having an established, inflammatory disease or disease associated with inflammation.

Aminoquinolines are derivatives of quinoline, most notable for their roles as antimalarial drugs. Representative examples of the aminoquinoline class include, but are not limited to 4-aminoquinolines, such as amodiaquine, hydroxychloroquine, chloroquine; and 8-aminoquinolines, such as primaquine and pamaquine. Such drugs may be formulated as a "free base" or more usually as a salt thereof.

Metabolites of hydroxychloroquine (HCQ) include desethylhydroxychloroquine (DHCQ), desethylchloroquine (DHQ), and bisdesethylchloroquine (BDCQ), and their chemical structures are presented in FIG. 1. FIG. 1B provides a summary of the experimental findings presented in FIGS. 2-25 for the anti-inflammatory disease and anti-metabolic disease activity (termed "efficacy") and the retinal toxicity (termed "toxicity") for HCQ and its metabolites DHCQ, DCQ and BDCQ.

The phrase "pharmaceutically acceptable salt(s)", as used herein, means those salts of compounds of the invention that are considered (e.g. by regulatory bodies such as the FDA and EMEA) as safe and effective for oral and topical use in mammals and that possess the desired biological activity. Pharmaceutically acceptable salts include salts of acidic or basic groups present in compounds of the invention. Pharmaceutically acceptable salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, pamoate (i.e., 1,1'-methylene-bis-(2-hydroxy-3-naphthoate)), aluminum, calcium, lithium, magnesium, potassium, sodium, zinc, and diethanolamine salts and the like, as known in the art.

The dose of DHCQ in the present invention comprises, consists of, or consists essentially of DHCQ or pharmaceutically acceptable salts or esters thereof in a daily dose of at least about 50 mg per day (about 0.83 mg/kg/day), at least about 100 mg per day (about 1.67 mg/kg/day), at least about 155 mg per day (about 2.58 mg/kg/day), at least about 200 mg per day (about 3.33 mg/kg/day), at least about 250 mg per day (about 4.16 mg/kg/day), at least about 300 mg per day (about 5 mg/kg/day), at least about 310 mg per day (about 5.16 mg/kg/day), at least about 350 mg per day (about 5.83 mg/kg/day), at least about 400 mg per day (about 6.67 mg/kg/day), about 450 mg per day (about 7.5 mg/kg/day), about 465 mg per day (about 7.75 mg/kg/day), about 500 mg per day (about 8.33 mg/kg/day), about 550 mg per day (about 9.16 mg/kg/day), about 600 mg per day (about 10 mg/kg/day), about 620 mg per day (about 10.33 mg/kg/day), about 800 mg per day (about 13.33 mg/kg/day), about 930 mg/kg/day (about 15.5 mg/kg/day), about 1000 mg per day (about 16.67 mg/kg/day), about 1200 mg per day (about 20 mg/kg/day), about 1300 mg per day (about 21.67 mg/kg/day), about 1400 mg per day (about 23.3 mg/kg/day), about 1500 mg per day (about 25 mg/kg/day), or about 1600 mg per day (about 26.67 mg/kg/day), inclusive of all ranges and subranges there between. In a particular embodiment, the DHCQ pharmaceutical composition is delivered in a once-daily dose.

As discussed herein, in various embodiments, the compositions and methods of the present invention can comprise any of the enumerated amounts or daily doses of DHCQ, or pharmaceutically acceptable salts or esters thereof described herein. The DHCQ can be delivered in a pharmaceutical composition in the form of a tablet, suspension or capsule. The DHCQ pharmaceutical composition can be administered in separate administrations or 2, 3, 4, 5, or 6 equal doses each day. Unless otherwise specified, an indicated dose of a pharmaceutically acceptable salt or ester of an active compound, e.g. DHCQ, is expressed as the amount of the corresponding "freebase" (non-salt, non-ester) form of the active compound.

Current recommendations for screening for HCQ-mediated and other aminoquinoline-mediated retinal toxicity are described (Marmor et al, Ophthalmology. 2011, 118(2):415-22; Bernstein H N. Surv Ophthalmol. October 1967; 12(5): 415-47; Anderson C et al, Retina. 2009; 29(8):1188-92; Michaelides M et al, Arch Ophthalmol. January 2011; 129 (1):30-9). The recommendations include performing a baseline examination of patients starting these drugs to serve as a reference point. Annual screening for eye toxicity should begin after 5 years, or sooner if there are additional risk factors including total cumulative dose of more than 1000 g, maintenance dose >6.5 mg/kg/day, renal abnormalities, liver disease, underlying retinal disease, or age greater than 60 years of age. Annual screening should include 10-2 automated field tests, along with at least one of the following tests: multifocal electroretinogram (mfERG), spectral domain optical coherence tomography (SD-OCT), or fundus autofluorescence (FAF). Because mfERG testing is an objective test that evaluates function, it may be used in place of visual field tests. Fundus examinations are advised for documentation, but visible bull's-eye maculopathy is a late change, and the goal of screening is to detect toxicity at an earlier stage. On annual HCQ toxicity screening examination, demonstration of a worsening of the results (deterioration of performance on the test and/or worsening of retinal or macular findings) of the multifocal electroretinogram (mfERG), spectral domain optical coherence tomography (SD-OCT), fundus autofluorescence (FAF), visual field tests, and/or direct visualization of the macula indicates the development of retinal toxicity. Early fundus changes in chloroquine/hydroxychloroquine toxicity include the loss of foveal reflex, macular edema, and pigment mottling that is enhanced with the red-free filter. The appearance of the macula correlates poorly with visual-field testing results. Decreased retinal toxicity (or less retinal toxicity) means that the results of these tests are stable and unchanged from the baseline results obtained in the initial pre-treatment baseline exam.

Baseline central visual field examination (perimetry) may be useful because the earliest macular changes due to aminoquinoline and HCQ toxicity are nonspecific and may be indistinguishable from age-related changes. The Humphrey 10-2 program (white target) is recommended for confirming defects found by the Amsler grid.

Electroretinography (ERG) can be full field, focal, or multifocal. Focal ERG techniques can record an ERG response from the foveal and parifoveal regions. mfERG, which is typically available in large clinical centers, is more appropriate for the evaluation of chloroquine and/or hydroxychloroquine toxicity because it generates local ERG responses topographically across the posterior pole and can document a bull's eye distribution of ERG depression. mfERG objectively evaluates function and can be used in place of visual fields.

Spectral Domain Optical Coherence Tomography (SD-OCT) measures peripapillary retinal nerve fiber layer (RNFL) thickness and macular inner and outer retinal thickness in patients with long-term exposure to hydroxychloroquine or chloroquine. OCT is useful to detect peripapillary RNFL thinning in clinically evident retinopathy. In addition, selective thinning of the macular inner retina can be detected in the absence of and before clinically apparent fundus changes.

In animal studies, the first morphologic changes, which become visible within 1 week after initiation of chloroquine treatment, involve ganglion cells manifesting membranous cytoplasmic bodies. Other neural cells of the retina later show these changes. Reversible changes are present for up to 5 months of therapy. Prolonged therapy resulted in progressive degeneration of the ganglion cells and photoreceptor cell bodies and nuclei with outer segment involvement. The most severe changes tended to be perifoveal, with relative foveal sparing. Abnormalities of the pigment epithelium and choroid were seen only after degeneration of the ganglion cells and photoreceptors was established. All of the observations described were made before any abnormalities became detectable in the fundus or on ERG. Pathologic studies of patients with chloroquine retinopathy are few and are limited to cases with advanced retinopathy. Consistent findings include degeneration of the outer retina, particularly the photoreceptors and the outer nuclear layer, with relative sparing of the photoreceptors in the fovea. Pigment migration into the retina is seen. Pathologic changes in the ganglion cells have been a consistent finding. Sclerosis of the retinal arterioles is variable.

The use of HCQ is often contraindicated in treating patients at increased risk for retinal toxicity due to the undesirable safety profile of HCQ in such patients. Patients at increased risk for retinal toxicity include patients with known retinal abnormalities such as diabetic or hypertensive retinopathy, macular degeneration prior retinal trauma. There is similar increased risk in any patient with type I or type II diabetes, patients who have taken HCQ for long periods of time (e.g., about 5 years or more), patients having received cumulative doses of about 1000 g or more, patients over age 60, or patients of small stature (ideal body weights of about 60 kg or less) as well as well as obese patients and patients with hepatic or renal impairment.

Withdrawal of the medication and shifting to another form of treatment is the standard of care for individuals with HCQ and other aminoquinoline-associated early retinal toxicity or retinal abnormalities. Coordination with the rheumatologist or the dermatologist is warranted for comprehensive care of the patient. If serious toxic symptoms occur from overdosage or sensitivity, it has been suggested that ammonium chloride (8 g daily in divided doses for adults) be administered orally 3-4 times/wk for several months after therapy has been stopped. Acidification of the urine with ammonium chloride increases renal excretion of the 4-aminoquinoline compounds by 20-90%. In patients with impaired renal function and/or metabolic acidosis, caution must be taken.

Recent clinical observations demonstrated that in humans taking conventional doses of HCQ (with 400 mg/day being a common dose), the prevalence of retinal toxicity was 6.8 users per 1,000 (Marmor et al, Ophthalmology. 2011 February; 118(2):415-22). The prevalence was dependent on the duration of HCQ use. Toxicity sharply increased towards 1% after 5-7 years of use. Treatment for >15 years resulted in even higher rates of retinal toxicity.

Based on the discoveries presented herein, the rate of retinal toxicity after long-term treatment of inflammatory diseases or conditions with DHCQ will be lower than that reported for treatment with HCQ (Marmor et al. describes rates of retinal toxicity for treatment with HCQ alone (Ophthalmology. 2011 February; 118(2):415-22)) when the DHCQ and HCQ are used at the same effective total cumulative dose and over the same time period. HCQ-mediated retinal toxicity is identified based on a worsening of the results (deterioration of performance on the test and/or worsening of retinal or macular findings) on annual screening multifocal electroretinogram (mfERG), spectral domain optical coherence tomography (SD-OCT), fundus autofluorescence (FAF), visual field tests, and/or direct visualization of the macula. Decreased retinal toxicity (or less retinal toxicity) means that for a group of individuals treated with DHCQ, there will be at least about a 25%, at least about a 35%, at least about a 45%, at least about a 55%, at least about a 65%, at least about a 75%, and may be around or up to about a 50% lower rate of retinal toxicity (e.g. toxicity determined based on worsening of function or performance, or development or worsening of abnormal physical characteristics or findings, of the retina or macula on annual screening test results) as compared to that reported for individuals treated with HCQ (or compared to a group of individuals treated with HCQ).

Specific measurements to document the rate (incidence) of retinal toxicity in individuals receiving treatment with DHCQ as compared to individuals taking HCQ at a similar effective cumulative dose and over a similar time period include, without limitation, the following (Marmor, Ophthalmology. 2011 February; 118(2):415-22):

(1) Ophthalmologic Examination. A thorough ophthalmologic dilated fundus examination to examine the retinal macula for evidence of bull's-eye maculopathy. Visible bull's-eye retinopathy indicates that toxicity has persisted long enough to cause RPE degeneration, and is a relatively late finding. The treatment with DHCQ provides at least about a 25%, at least about a 35%, at least about a 45%, at least about a 55%, at least about a 65%, at least about a 75%, and may be around or up to about a 50% lower rate of bull's-eye maculopathy at 5 years, at 10 years, at 15 years, and at 20 years of treatment as compared to treatment with HCQ at a similar effective cumulative dose and over a similar time period.

(2) Automated Threshold Visual Fields. Parafoveal loss of visual sensitivity may appear before changes are seen on fundus examination. Automated threshold visual field testing with a white 10-2 pattern (i.e., testing with white targets within 10 degrees of the fovea) gives high resolution within the macular region. The finding of any reproducibly depressed central or parafoveal spots can be indicative of early toxicity. Advanced toxicity will typically show a well-developed paracentral scotoma (with or without central sensitivity loss). The treatment with DHCQ provides at least about a 25%, at least about a 35%, at least about a 45%, at least about a 55%, at least about a 65%, at least about a 75%, and up to about a 50% lower rate of depressed central or parafoveal spots at 5 years, at 10 years, at 15 years, and at 20 years of treatment as compared to treatment with HCQ at a similar effective cumulative dose and over a similar time period. The treatment with DHCQ is anticipated to be associated with at least about a 25%, at least about a 35%, at least about a 45%, at least about a 55%, at least about a 65%, at least about a 75%, and may be around or up to about a 50% lower rate of reproducibly depressed central or parafoveal spots at 5 years, at 10 years, at 15 years, and at 20 years of treatment as compared to treatment with HCQ at a similar effective cumulative dose and over a similar time period.

(3) Spectral Domain-Optical Coherence Tomography. Optical coherence tomography shows a cross-section of retinal layers in the macula. High-resolution instruments (SD or Fourier domain OCT) can show localized thinning of the retinal layers in the parafoveal region and confirm toxicity. Loss of the inner-/outer-segment line may be an early objective sign of parafoveal damage. Further work is needed to evaluate the sensitivity of SD-OCT relative to visual fields or mfERG, but a number of cases have shown prominent SD-OCT changes before visual field loss; 16, 19-22 SD-OCT testing is rapid and the equipment is available in many offices and clinics. The treatment with DHCQ provides at least about a 25%, at least about a 35%, at least about a 45%, at least about a 55%, at least about a 65%, at least about a 75%, and up to about a 50% lower rate of localized thinning of the retinal layers in the parafoveal region at 5 years, at 10 years, at 15 years, and at 20 years of treatment as compared to treatment with HCQ at a similar effective cumulative dose and over a similar time period.

(4) Fundus Autofluorescence. Autofluorescence imaging may reveal subtle RPE defects with reduced autofluorescence or show areas of early photoreceptor damage (which appear as increased autofluorescence from an accumulation of outer segment debris). It has the advantage over fluorescein angiography of being faster and not requiring dye injection. Some cases have demonstrated FAF abnormalities before visual field loss. The treatment with DHCQ provides at least about a 25%, at least about a 35%, at least about a 45%, at least about a 55%, at least about a 65%, at least about a 75%, and up to about a 50% lower rate of subtle RPE defects with reduced autofluorescence or areas of early photoreceptor damage at 5 years, at 10 years, at 15 years, and at 20 years of treatment as compared to treatment with HCQ at a similar effective cumulative dose and over a similar time period.

(5) Multifocal Electroretinogram. The mfERG generates local ERG responses topographically across the posterior pole and can objectively document localized paracentral ERG depression in early CQ and HCQ retinopathy. mfERG may be more sensitive to early paracentral functional loss than the white 10-2 field. The treatment with DHCQ provides at least about a 25%, at least about a 35%, at least about a 45%, at least about a 55%, at least about a 65%, at least about a 75%, and up to about a 50% lower rate of localized paracentral ERG depression at 5 years, at 10 years, at 15 years, and at 20 years of treatment as compared to treatment with HCQ at a similar effective cumulative dose and over a similar time period.

As described herein, as compared to the rates of retinal toxicity described in the art, given a similar level of therapeutic activity and time period of dosing for HCQ, treatment with DHCQ provides less retinal toxicity as compared to treatment with HCQ used at a similar effective total cumulative HCQ dose. In one embodiment, substantially without retinal toxicity means that in a patient population analogous to that described by the American College of Opthamolology and Marmor et al (Ophthalmology. 2011 February; 118(2):415-22), in which the retinal toxicity rate approached 1% after 5 years in individuals treated with HCQ, treatment with DHCQ will reduce the rate of retinal toxicity to less that about 0.5% of treated individuals. Retinal toxicity is identified based on worsening of the results (deterioration of performance on the test, and/or development or worsening of physical abnormalities, of retinal or macular physical characteristics or findings) on annual screening multifocal electroretinogram (mfERG), spectral domain optical coherence tomography (SD-OCT), fundus autofluorescence (FAF), visual field tests, and/or direct visualization of the macula examinations. Further, given current assumptions that retinal screening is justified as rates of toxicity approach 1%, the reduction in cumulative rates of retinal toxicity associated with DHCQ treatment can in turn reduce the need for retinal toxicity screening to a single screening at 5 and 10 years, or to entirely negate the need for screening, or to performing screening on an every other year basis starting 7 years following initiation of therapy. Due to the lower retinal toxicity of DHCQ, use of DHCQ will enable a higher total cumulative dose to be delivered as compared to treatment with HCQ, thereby enabling dosing of DHCQ at higher daily doses and/or over a longer period of time which to provide greater efficacy in treating the inflammatory disease. Due to the lower retinal toxicity of DHCQ, use of DHCQ will enable treatment of individuals at increased risk, in the pre-clinical phases, or in the early-stages of an inflammatory disease or disease associated with inflammation who require treatment over a long period of time to prevent development of the inflammatory disease or disease associated with inflammation.

In another embodiment, substantially without retinal toxicity means that in groups of subjects in which one group is treated with DHCQ and a second group is treated with HCQ (when the DCHQ and HCQ are used at the same total cumulative doses), that after 5 years of treatment the group treated with DHCQ will exhibit an approximately 50% lower incidence of retinal toxicity as compared to the group treated with HCQ. In another embodiment, substantially without retinal toxicity means that in groups of subjects in which one group is treated with DHCQ and a second group is treated with HCQ (when the DHCQ and HCQ are used at the same total cumulative dose), that after 10 years of treatment the group treated with DHCQ will exhibit an approximately 50% lower incidence of retinal toxicity as compared to the group treated with HCQ. In another embodiment, substantially without retinal toxicity means that in groups of subjects in which one group is treated with DHCQ and a second group is treated with HCQ (when the DHCQ and HCQ are used at the same total cumulative dose), that after 15 years of treatment the group treated with DHCQ will exhibit an approximately 50% lower retinal toxicity as compared to the group treated with HCQ. In another embodiment, substantially without retinal toxicity means that in groups of subjects in which one group is treated with DHCQ and a second group is treated with HCQ (when the DHCQ and HCQ are used at a similar total cumulative doses), that after 20 years of treatment the group treated with DHCQ will exhibit an approximately 50% lower incidence of retinal toxicity as compared to the group treated with HCQ.

In addition to reducing the incidence of retinal toxicity as described above, the use of DHCQ can reduce the severity of retinal toxicity when it does occur. The use of DHCQ reducing the severity of retinal toxicity means that for an individual taking DHCQ that develops retinal toxicity that there will be at least about a 25%, at least about a 35%, at least about a 45%, at least about a 55%, at least about a 65%, at least about a 75%, and may be around or up to about a 50% reduction in the severity of the retinal toxicity (e.g. the degree of toxicity determined based on worsening of function or performance, or development or worsening of abnormal physical characteristics or findings, of the retina or macula on annual screening test results) as compared to that reported for individuals treated with a similar cumulative dose of, and over a similar time frame with, HCQ.

As discussed above, current recommendations for screening for HCQ-mediated and other aminoquinoline-mediated retinal toxicity are described (Marmor et al, Ophthalmology. 2011, 118(2):415-22; Bernstein H N. Surv Ophthalmol. October 1967; 12(5):415-47; Anderson C et al, Retina. 2009; 29(8):1188-92; Michaelides M et al, Arch Ophthalmol. January 2011; 129(1):30-9). The recommendations include performing a baseline examination of patients starting these drugs to serve as a reference point. Following this baseline exam, the recommendations are for annual screening for retinal toxicity begin at 5 years of HCQ treatment in individuals who do not have risk factors for retinal toxicity. For individuals with risk factors for retinal toxicity, it is recommended that annual screening begin before an individual reaches 5 years of HCQ therapy. The recommendations outline risk factors for retinal toxicity as including one or more of the following: total cumulative dose of HCQ sulfate of more than 1000 g, maintenance dose of HCQ sulfate >6.5 mg/kg/day, renal insufficiency, liver disease, underlying retinal disease, age older than 60 years of age. Annual screening should include 10-2 automated field tests, along with at least one of the following tests: multifocal electroretinogram (mfERG), spectral domain optical coherence tomography (SD-OCT), or fundus autofluorescence (FAF). Because mfERG testing is an objective test that evaluates function, it may be used in place of visual field tests. Fundus examinations are advised for documentation, however, visible bull's-eye maculopathy is a late change, and the goal of screening is to detect toxicity at an earlier stage. On annual HCQ toxicity screening examination, demonstration of a worsening of the results (deterioration of performance on the test and/or worsening of retinal or macular findings) of the multifocal electroretinogram (mfERG), spectral domain optical coherence tomography (SD-OCT), fundus autofluorescence (FAF), visual field tests, and/or direct visualization of the macula indicates the development of retinal toxicity. Early fundus changes in chloroquine/hydroxychloroquine toxicity include the loss of foveal reflex, macular edema, and pigment mottling that is enhanced with the red-free filter. The appearance of the macula correlates poorly with visual-field testing results. Decreased retinal toxicity (or less retinal toxicity) means that the results of these tests are stable and unchanged from the baseline results obtained in the initial pre-treatment baseline exam.

The discovery described herein of lower toxicity of DHCQ relative to conventional therapies such as HCQ reduces the concerns regarding retinal toxicity, and therefore retinal toxicity screening can be safely initiated much later when DHCQ is used, compared to HCQ. In one embodiment, the use of DHCQ would allow retinal toxicity screening to be safely performed beginning at about 5 years following initiation of therapy. In another embodiment, the use of DHCQ would allow retinal toxicity screening to be safely performed beginning at about 7 years following initiation of therapy. In another embodiment, the use of DHCQ would allow retinal toxicity screening to be safely performed beginning at about 10 years following initiation of therapy. In another embodiment, the use of DHCQ would allow retinal toxicity screening to be safely performed beginning at about 15 years following initiation of therapy. In another embodiment, the use of DHCQ would allow retinal toxicity screening to be safely performed beginning at about 20 years following the initiation of therapy. In another embodiment, the use of DHCQ would allow for no retinal toxicity screening. In contrast, the use of HCQ requires retinal toxicity screening at baseline and annually starting 5 years following the initiation of HCQ therapy.

Similarly, the lower toxicity of DHCQ permits less frequent retinal toxicity screening compared to treatment with HCQ. In one embodiment, the use of DHCQ allows retinal toxicity screening to be safely performed at about 1 year intervals. In another embodiment, the use of DHCQ allows retinal toxicity screening to be safely performed at about 18 month intervals. In another embodiment, the use of DHCQ allows retinal toxicity screening to be safely performed at about 2 year intervals. In another embodiment, the use of DHCQ allows retinal toxicity screening to be safely performed at about 3 year intervals. In another embodiment, the use of DHCQ allows retinal toxicity screening to be safely performed at about 5 year intervals. In another embodiment, the use of DHCQ allow retinal toxicity screening to be safely performed at about 7 year intervals. In another embodiment, the use of DHCQ allows retinal toxicity screening to be safely performed at about 10 year intervals. In another embodiment, the use of DHCQ enables a patient to continue treatment without any retinal toxicity screening.

In another embodiment, the therapeutic use of DHCQ allows the safe use or continued use of aminoquinoline therapy in those at increased risk for retinal toxicity, including but not limited to individuals with prior use of hydroxychloroquine. In one embodiment, the use of DHCQ enables the treatment (or continued treatment) of individuals who are at risk of unacceptable levels of retinal toxicity because they previously used HCQ for longer than about 2.5 years. In another embodiment, the use of DHCQ enables the treatment (or continued treatment) of individuals who are at risk of unacceptable levels of retinal toxicity because they previously used HCQ for longer than about 5 years. In another embodiment, the use of DHCQ enables the treatment (or continued treatment) of individuals who are at risk of unacceptable levels of retinal toxicity because they previously used HCQ for longer than about 7 years. In another embodiment, the use of DHCQ enables the treatment (or continued treatment) of individuals who are at risk of unacceptable levels of retinal toxicity because they previously used HCQ for longer than about 10 years. In another embodiment, the use of DHCQ enables the treatment (or continued treatment) of individuals who are at risk of unacceptable levels of retinal toxicity because they previously used HCQ for longer than about 15 years.

In another embodiment, the use of DHCQ therapy enables aminoquinoline therapy (or continued therapy) in individuals over age >60 years. In another embodiment, the use of DHCQ therapy enables treatment of individuals with small stature or low body weight, with retinopathy, at risk for underlying retinopathy, other ocular pathology, or have taken 1000 grams or more of HCQ. Short stature, in certain cases referred to as small stature or diminutive stature in the literature, refers to humans who weight <60 Kg or less that 135 lbs.

In another embodiment, the use of DHCQ allows the use of aminoquinoline therapy (or continued therapy) in patients who are at risk of unacceptable levels of retinal toxicity because they have taken doses of HCQ of 1000 grams or more in their lifetime. In another embodiment, the use of DHCQ allows the use of aminoquinoline therapy (or continued therapy) in patients who are at risk of unacceptable levels of retinal toxicity because they have taken doses of HCQ of 2000 grams or more in their lifetime. In another embodiment, the use of DHCQ allows the use of aminoquinoline therapy (or continued therapy) in patients who are at risk of unacceptable levels of retinal toxicity because they have taken doses of HCQ of 3000 grams or more in their lifetime. In another embodiment, the use of DHCQ allows the use of aminoquinoline therapy (or continued therapy) in patients who are at risk of unacceptable levels of retinal toxicity because they have taken doses of HCQ of 5000 grams or more in their lifetime. In another embodiment, the use of DHCQ reduces the risk of aminoquinoline therapy in patients who are at risk of unacceptable levels of retinal toxicity because they have taken doses of HCQ >500 grams in their lifetime. In another embodiment, the use of DHCQ reduces the risk of aminoquinoline therapy in patients who are at risk of unacceptable levels of retinal toxicity because they have taken doses of HCQ >250 grams in their lifetime. In another embodiment, the use of DHCQ reduces the risk of aminoquinoline therapy in patients who are at risk of unacceptable levels of retinal toxicity because they have taken doses of HCQ >100 grams in their lifetime. In another embodiment, the use of DHCQ reduces the risk of aminoquinoline therapy in patients who are at risk of unacceptable levels of retinal toxicity because they have taken doses of HCQ >50 grams in their lifetime.

In another embodiment, the use of DHCQ allows the safe use of aminoquinoline therapy in patients who are at risk of unacceptable levels of retinal toxicity because they have taken doses of DHCQ of 1000 grams or more in their lifetime. In another embodiment, the use of DHCQ allows the safe use of aminoquinoline therapy in patients who are at risk of unacceptable levels of retinal toxicity because they have taken doses of DHCQ of 2000 grams or more in their lifetime. In another embodiment, the use of DHCQ allows the safe use of aminoquinoline therapy in patients who have taken doses of DHCQ of 3000 grams or more in their lifetime. In another embodiment, the use of DHCQ allows the safe use of aminoquinoline therapy in patients who have taken doses of DHCQ of 5000 grams or more in their lifetime. In another embodiment, the use of DHCQ provides a reduced risk of using of aminoquinoline therapy in patients who have taken doses of DHCQ >500 grams in their lifetime. In another embodiment, the use of DHCQ provides a reduced risk of using of aminoquinoline therapy in patients who have taken doses of DHCQ >250 grams in their lifetime. In another embodiment, the use of DHCQ provides a reduced risk of using of aminoquinoline therapy in patients who have taken doses of DHCQ >100 grams in their lifetime. In another embodiment, the use of DHCQ provides a reduced risk of using of aminoquinoline therapy in patients who have taken doses of DHCQ >50 grams in their lifetime.

In another embodiment, the use of DHCQ provides a reduced risk of retinal toxicity from aminoquinoline therapy in patients that would be candidates for therapy with anti-malarials including but not limited to HCQ. In another embodiment, the use of DHCQ provides a reduced risk of retinal toxicity from aminoquinoline therapy in obese patients (body mass index >30) that would be candidates for therapy with anti-malarials including but not limited to HCQ. In another embodiment, the use of DHCQ provides a reduced risk of retinal toxicity from aminoquinoline therapy in patients or small stature (body mass index <18.5) and/or low ideal body weight (<60 Kg) that would be candidates for therapy with anti-malarials including but not limited to hydroxychloroquine.

In another embodiment, the use of DHCQ provides a reduced risk of retinal toxicity from aminoquinoline therapy in patients with renal impairment (creatinine clearance <60 ml/ml) or hepatic impairment (serum albumin <3.5 mg/dL or INR >1.2 or direct bilirubin >0.2 mg/dL) that would be candidates for therapy with anti-malarials including but not limited to HCQ.

In another embodiment, the use of DHCQ provides a reduced risk of using of aminoquinoline therapy in patients with underlying retinal disease (including diabetic or hypertensive retinopathy, macular degeneration, or prior retinal trauma) that would be candidates for therapy with antimalarials including but not limited to hydroxychloroquine In another embodiment use of DHCQ provides a reduced risk of using of aminoquinoline therapy in patients at risk for concurrent retinal disease (including diabetic patients, hypertensive patients, and patients with a strong family history of macular degernation) that would be candidates for therapy with antimalarials including but not limited to hydroxychloroquine Statins are inhibitors of HMG-CoA reductase enzyme. These agents are described in detail in various publications. For example, mevastatin and related compounds are disclosed in U.S. Pat. No. 3,983,140, lovastatin (mevinolin) and related compounds are disclosed in U.S. Pat. No. 4,231,938, pravastatin and related compounds are disclosed in U.S. Pat. No. 4,346,227, simvastatin and related compounds are disclosed in U.S. Pat. Nos. 4,448,784 and 4,450,171; fluvastatin and related compounds are disclosed in U.S. Pat. No. 5,354,772; atorvastatin and related compounds are disclosed in U.S. Pat. Nos. 4,681,893, 5,273,995 and 5,969,156; and cerivastatin and related compounds are disclosed in U.S. Pat. Nos. 5,006,530 and 5,177,080. Additional statin compounds are disclosed in U.S. Pat. Nos. 5,208,258, 5,130,306, 5,116,870, 5,049,696, RE 36,481, and RE 36,520. Statins include the salts and/or ester thereof.

For the purposes of the present invention, an effective dose of a statin in a combination with DHCQ (or salt or ester thereof) is the dose that, when administered for a suitable period of time, usually at least about one week, about two weeks or more, or up to extended periods of time such as months or years, will evidence a reduction in the progression of the disease. It will be understood by those of skill in the art that an initial dose may be administered for such periods of time, followed by maintenance doses, which, in some cases, will be at a reduced dosage.

The formulation and administration of statins is well known, and will generally follow conventional usage. The dosage required to treat inflammation may be commensurate with the dose used in the treatment of high cholesterol. For example, atorvastatin may be administered in a daily dose of at least about 1 mg, at least about 5 mg, at least about 10 mg, and not more than about 250 mg, not more than about 150 mg, or not more than about 80 mg, inclusive of a values, ranges, and subranges therebetween. The use of statins in general and atorvastatin in particular can be at doses from about 1-250 mg (about 0.01-2.5 mg/kg), and DHCQ specifically from about 50-1000 mg per day (about 0.83-16.67 mg/kg). Table 1 presents the half life ($T_{1l2}$), maximum concentration ($C_{max}$ in mg/L), the time it takes to reach $C_{max}$ ($T_{max}$ in hours), volume distribution ($V_d$ in L) and percent oral bioavailability of atorvastatin.

The DHCQ (or salt or ester thereof), and/or statins can be incorporated into a variety of formulations for therapeutic administration. More particularly, the compounds of the present invention can be formulated into pharmaceutical compositions by combination with appropriate pharmaceutically acceptable carriers or diluents either alone or in combination with an aminoquinoline, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, intraarticular, etc., administration. The active agent may be systemic after administration or may be localized by the use of regional administration, intramural administration, or use of an implant that acts to retain the active dose at the site of implantation. In particular embodiments, the formulations are oral formulations.

The use of combination therapy may allow lower doses of each monotherapy than currently used in standard practice while achieving significant efficacy, including efficacy beyond that conventional dosing of either monotherapy. Those of skill in the art will readily appreciate that dose levels can vary as a function of the specific compound, the severity of the symptoms, and the susceptibility of the subject to side effects. Some of the specific compounds are more potent than others. Preferred dosages for a given compound are readily determinable by those of skill in the art by a variety of means. A preferred means is to measure the physiological potency of a given compound. The use of combination therapy may allow lower doses of each monotherapy than currently used in standard practice while achieving significant efficacy, including efficacy greater than that achieved by conventional dosing of either monotherapy.

Specific examples of statins useful in the methods of the invention are atorvastatin (LIPITOR™); cerivastatin (LIPOBAY™); fluvastatin (LESCOL™); lovastatin (MEVACOR™); mevastatin (COMPACTIN™); pitavastatin (LIVALO™); pravastatin (PRAVACHOL™); Rosuvastatin (CRESTOR™); simvastatin (ZOCOR™); etc.

A combination drug product of the invention, which can be provided as a single formulation or as two separate formulations of the active ingredients, DHCQ and a statin. In particular embodiments the combination provides for a synergistic improvement in disease markers or disease symptoms over the administration of either drug as a single agent.

In some embodiments, the formulation or combination of active agents consists essentially of the combination of DHCQ and atorvastatin, i.e. no additional active agents are included in the formulation, although excipients, packaging and the like will be present. In some embodiments the formulation is free of NSAIDs, including aspirin. In some embodiments the formulation is free of folic acid or folate. Importantly, this combination does not require use of an antibiotic, an anti-viral, or an anti-bacterial agent, and in some embodiments the formulation is free of antibiotics, anti-viral, or anti-bacterial agents.

The combination can be defined based on the dose ratio of the two drugs, where the DHCQ is usually expressed as the amount of base drug that is present, i.e. not including the weight contribution of the counter ion. Where the composition comprises DHCQ and atorvastatin, the ratio of these two active agents may range from about 160 mg:80 mg (about 2.6 mg/kg:1.3 mg/kg) to about 600 mg:1 mg (about 10 mg/kg:0.016 mg/kg), from about 500 mg:100 mg (about 8.33 mg/kg:1.6 mg/kg) to about 500 mg:10 mg (about 8.33 mg/kg:0.16 mg/kg), from about 100 mg:10 mg (about 1.6 mg/kg:0.16 mg/kg) to about 600 mg:10 mg (about 10 mg/kg:0.16 mg/kg), to about 150 mg:10 mg (2.5 mg/kg:0.16 mg/kg), to about 600 mg:20 mg (about 10 mg/kg:0.28 mg/kg).

In a particular embodiment, the combination of desethylhydroxychloroquine (DHCQ) and atorvastatin are administered in one of the following once-daily fixed dosages (DHCQ base mg:atorvastatin base mg): about 800:80, about 600:80, about 500:80, about 465:80, about 450:80, about 425:80, about 400:80, about 375:80, about 325:80, about 310:80, about 300:80, about 275:80, about 250:80, about 225:80, about 200:80, about 155:80 about 100:80, about 800:60, about 600:60, about 500:60, about 465:60, 450:60, about 425:60, about 400:60, about 375:60, about 325:60, about 310:60, about 300:60, about 275:60, about 250:60, about 225:60, about 200:60, about 155:60 about 100:60, 800:50, 600:50, 500:50, 465:50, 450:50, 425:50, 400:50, 375:50, 325:50, 310:50, about 300:50, about 275:50, about 250:50, about 225:50, about 200:50, about 155:50, about 100:50, about 800:45, about 600:45, about 500:45, about 465:45, about 450:45, about 425:45, about 400:45, about 375:45, about 325:45, about 310:45, about 300:45, about 275:45, about 250:45, about 225:45, about 200:45, about 155:45, about 100:45, about 800:40, about 600:40, about 500:40, about 465:40, about 450:40, about 425:40, about 400:40, about 375:40, about 325:40, about 310:40, about 300:40, about 275:40, about 250:40, about 225:40, about 200:40, about 155:40, about 100:40, about 800:35, about 600:35, about 500:35, about 465:35, about 450:35, about 425:35, about 400:35, about 375:35, about 325:35, about 310:35, about 300:35, about 275:35, about 250:35, about 225:35, about 200:35, about 155:35, about 100:35, about 800:30, about 600:30, about 500:30, about 465:30, about 450:30, about 425:30, about 400:30, about 375:30, about 325:30, about 310:30, about 300:30, about 275:30, about 250:30, about 225:30, about 200:30, about 155:30, about 100:30, about 800:25, about 600:25, about 500:25, about 465:25, about 450:25, about 425:25, about 400:25, about 375:25, about 325:25, about 310:25, about 300:25, about 275:25, about 250:25, about 225:25, about 200:25, about 155:25, about 100:25, about 800:20, about 600:20, about 500:20, about 465:20, about 450:20, about 425:20, about 400:20, about 375:20, about 325:20, about 310:20, about 300:20, about 275:20, about 250:20, about 225:20, about 200:20, about 155:20, about 100:20, about 800:15, about 600:15, about 500:15, about 465:15, about 450:15, about 425:15, about 400:15, about 375:15, about 325:15, about 310:15, about 300:15, about 275:15, about 250:15, about 225:15, about 200:15, about 155:15, about 100:15, about 800:10, about 600:10, about 500:10, about 465:10, about 450:10, about 425:10, about 400:10, about 375:10, about 325:10, about 310:10, about 300:10, about 275:10, about 250:10, about 225:10, about 200:10, about 155:10, about 100:10, about 800:5, about 600:5, about 500:5, about 465:5, about 450:5, about 425:5, about 400:5, 375:5, about 325:5, about 310:5, about 300:5, about 275:5, about 250:5, about 225:5, 200:5, about 155:5, or about 100:5.

For demonstrating the synergistic activity of the two drugs (e.g., DHCQ and a statin such as atorvastatin) and establishing an appropriate fixed-dose ratio for clinical investigation, varying amounts of the two drugs are administered to appropriate animal models of inflammatory disease, either at a time of active disease (following disease onset) or at an early time point representative of pre-clinical disease, and the effect on disease activity or progression is measured. Alternatively, the effects of varying amounts of the two drugs are tested on a cellular response mediating inflammation that may be involved in the pathogenesis of disease.

It is within the level of skill of a clinician to determine the preferred route of administration and the corresponding dosage form and amount, as well as the dosing regimen, i.e., the frequency of dosing. In particular embodiments, the combination therapy will be delivered in once-a-day (s.i.d.) dosing. In other embodiments, twice-a-day (b.i.d.) dosing may be used. However, this generalization does not take into account such important variables as the specific type of inflammatory disease, the specific therapeutic agent involved and its pharmacokinetic profile, and the specific individual involved. For an approved product in the marketplace, much of this information is already provided by the results of clinical studies carried out to obtain such approval. In other cases, such information may be obtained in a straightforward manner in accordance with the teachings and guidelines contained in the instant specification taken in light of the knowledge and skill of the artisan. The results that are obtained can also be correlated with data from corresponding evaluations of an approved product in the same assays.

In some embodiments, the DHCQ is dosed at a higher initial dosing range (dose loading) to ensure more rapid achievement of therapeutic levels in blood and tissue, because this agent is known to have wide distribution and thus an extended terminal half-life. Such loading achieves steady-state blood levels, and increases tissue levels, more rapidly than single-dose daily dosing and results in earlier therapeutic efficacy (Furst et al, Arthritis Rheum. 1999 February; 42(2):357-65). Based on the loading dose used for HCQ, the typical dose loading may be in the range of about 500-1600 mg/d (about 8.33-26.6 mg/kg/d) for about 1-24 weeks, or for about 1-16 weeks, for DHCQ. This dose loading is done either alone, administered separately from the statin, or combined with the statin, including use of a "dose pack" with a blister packaging or other mechanism that provides clear information about daily dosing that would facilitate initial dose loading followed by continuation with a stable daily dosing, or other regular dosing intervals sufficient to achieve target drug levels and pharmacodymamic efficacies. The loading dose is typically delivered daily for 1-16 weeks, following which the dose is decreased to the typical maintenance dose of about 400-800 mg per day (about 6.67-13.3 mg/kg/day), or about 550-700 mg per day (9.16-11.67 mg/kg/day). DHCQ can be delivered in once-daily doses (e.g. about 600 mg per day orally [about 10 mg/kg/day]), or in a divided twice-daily dose (e.g. about 300 mg orally twice per day [for a total of about 10 mg/kg/day]). DHCQ can be delivered in once-daily doses (e.g. about 550 mg per day orally [about 9.16 mg/kg/day]), or in a divided twice-daily dose (e.g. about 275 mg orally twice per day [for a total of about 9.16 mg/kg/day]).

In one aspect, the present invention provides a unit dosage form of the formulation of the invention. The term "unit dose" or "unit dosage form," refers to physically discrete units suitable as unitary dosages for human subjects, each unit containing a predetermined quantity of drugs in an amount calculated sufficient to produce the desired effect in association with a pharmaceutically acceptable diluent, carrier, or vehicle. The specifications for the unit dosage forms of the present invention depend on the particular combination employed and the effect to be achieved, and the pharmacodynamics associated with the host.

In one aspect, the DHCQ is formulated into a pharmaceutical composition by combination with appropriate, pharmaceutically acceptable carriers or diluents, and are formulated into preparations in solid, semi-solid, liquid, suspension, emulsion, or gaseous forms, such as tablets, capsules, powders, granules, ointments, solutions, suspensions, emulsions, suppositories, injections, inhalants, gels, microspheres, and aerosols. As such, administration can be achieved in various ways, usually by oral administration. In pharmaceutical dosage forms, the drugs may be administered in the form of their pharmaceutically acceptable salts, or they may also be used alone or in appropriate association, as well as in combination with other pharmaceutically active compounds. The following methods and excipients are exemplary and are not to be construed as limiting the invention.

In particular embodiments, the $T_{max}$ of DHCQ after administration of the compositions of the present invention ranges from about 15 minutes to about 2 hours, about 15 minutes to about 1 hour, about 30 minutes to about 1 hour, about 30 minutes to about 2 hours, about 30 minutes to about 3 hours, about 1 hour to about 2 hours, about 1 hour to about 2.5 hours, about 1 hour to about 3 hours, about 1 hour to about 4 hours, or about 1 hour to about 5 hours, about 2 hours to about 6 hours, about 2 hours to about 7 hours, about 1 hour to about 8 hours, about 1 hour to about 9 hours, about one hour to about 10 hours, about 1 hour to about 11 hours, about 1 hour to about 12 hours. In some other embodiments, the $T_{max}$ of DHCQ after administration of the compositions of the present invention ranges from about 2 hours to 2.5 hours, about 2-3 hours, about 2-4 hours, about 2-5 hours, about 2-6 hours, about 2-7 hours, about 2-8 hours, about 2-9 hours, about 2-10 hours, about 2-11 hours, or about 2-12 hours.

In particular embodiments, the $C_{max}$ (in ng/ml of whole blood) of DHCQ after administration of the compositions of the present invention ranges from about 25-50, about 25-100, about 25-150, about 25-200, about 50-75, about 50-100, about 50-150, about 50-200, about 50-250, about 50-300, about 50-400, or about 50-500. In another embodiment, the $C_{max}$ (in ng/ml of whole blood) of DHCQ after administration of the compositions of the present invention ranges from about 100-150, about 100-200, about 100-250, about 100-250, about 100-300, about 100-350, about 100-400, about 100-450, about 100-500, about 100-550, about 100-600, or about 100-700. In another embodiment, the $C_{max}$ (in ng/ml of whole blood) of DHCQ after administration of the compositions of the present invention ranges from about 150-200, about 150-250, about 150-300, about 150-350, about 150-400, about 150-450, about 150-500, about 150-550, about 150-600, about 150-650, about 150-700, or about 150-800. In another embodiment, the $C_{max}$ (in ng/ml of whole blood) of DHCQ after administration of the compositions of the present invention ranges from about 200-250, about 200-300, about 200-350, about 200-400, about 200-450, about 200-500, about 200-550, about 200-600, about 200-650, about 200-700, about 200-750, or about 200-800. In another embodiment, the $C_{max}$ (in ng/ml of whole blood) of DHCQ after administration of the compositions of the present invention ranges from about 250-300, about 250-350, about 250-400, about 250-450, about 250-500, about 250-550, about 250-600, about 250-650, about 250-700, about 250-750, about 250-800, or about 250-850.

In particular embodiments, the volume of distribution ($V_d$; in liters) of DHCQ after administration of the compositions of the present invention ranges from about 100-150, about 100-200, about 100-250, about 100-250, about 100-300, about 100-350, about 100-400, about 100-450, about 100-500, about 100-550, about 100-600, or about 100-700. In another embodiment, the volume of distribution ($V_d$; in liters) of DHCQ after administration of the compositions of the present invention ranges from about 150-200, about 150-250, about 150-300, about 150-350, about 150-400, about 150-450, about 150-500, about 150-550, about 150-600, about 150-650, about 150-700, or about 150-800. In another embodiment, the volume of distribution ($V_d$; in liters) of DHCQ after administration of the compositions of the present invention ranges from about 200-250, about 200-300, about 200-350, about 200-400, about 200-450, about 200-500, about 200-550, about 200-600, about 200-650, about 200-700, about 200-750, or about 200-800. In another embodiment, the volume of distribution ($V_d$; in liters) of DHCQ after administration of the compositions of the present invention ranges from about 250-300, about 250-350, about 250-400, about 250-450, about 250-500, about 250-550, about 250-600, about 250-650, about 250-700, about 250-750, about 250-800, or about 250-850. In another embodiment, the volume of distribution ($V_d$; in liters) of DHCQ after administration of the compositions of the present invention ranges from about 300-350, about 300-400, about 300-450, about 300-350, about 300-400, about 300-450, about 300-500, about 300-550, about 300-600, about 300-650, about 300-700, about 300-750. In another embodiment, the volume of distribution ($V_d$; in liters) of DHCQ after administration of the compositions of the present invention ranges from about 350-400, about 350-450, about 350-500, about 350-550, about 350-600, about 350-650, about 350-700, about 350-750, about 350-800, about 350-850, about 350-900, about 350-950. In another embodiment, the volume of distribution ($V_d$; in liters) of DHCQ after administration of the compositions of the present invention ranges from about 400-450, about 400-500, about 400-550, about 400-600, about 400-650, about 400-700, about 400-750, about 400-800, about 400-850, about 400-900, about 400-950, or about 400-1000.

In particular embodiments, the clearance (Cl; in liters per hour) of DHCQ after administration of the compositions of the present invention ranges from about 0.5-1, about 0.5-1.5, about 0.5-2, about 0.5-2.5, about 0.5-3, about 0.5-3.5, about 0.5-4, about 0.5-4.5, about 0.5-5, about 0.5-5.5, about 0.5-6, about 0.5-6.5. In another embodiment, the clearance (Cl; in liters per hour) of DHCQ after administration of the compositions of the present invention ranges from about 1-1.5, about 1-2, about 1-2.5, about 1-3, about 1-3.5, about 1-4, about 1-4.5, about 1-5, about 1-5.5, about 1-6, about 1-6.5, about 1-7. In another embodiment, the clearance (Cl; in liters per hour) of DHCQ after administration of the compositions of the present invention ranges from about 1.5-2, about 1.5-2.5, about 1.5-3, about 1.5-3.5, about 1.5-4, about 1.5-4.5, about 1.5-5, about 1.5-5.5, about 1.5-6, about 1.5-6.5, about 1.5-7, about 1.5-7.5. In another embodiment, the clearance (Cl; in ml per hour) of DHCQ after administration of the compositions of the present invention ranges from about 150-200, about 150-250, about 150-300, about 150-350, about 150-400, about 150-450, about 150-500, about 150-550, about 150-600, about 150-650, about 150-700, or about 150-800.

In another embodiment, the clearance (Cl; in ml per hour) of DHCQ after administration of the compositions of the present invention ranges from about 250-300, about 250-350, about 250-400, about 250-450, about 250-500, about 250-550, about 250-600, about 250-650, about 250-700, about 250-750, about 250-800, or about 250-850. In another embodiment, the clearance (Cl; in ml per hour) of DHCQ after administration of the compositions of the present invention ranges from about 350-400, about 350-450, about 350-500, about 350-550, about 350-600, about 350-650, about 350-700, about 350-750, about 350-800, about 350-850, about 350-900, or about 350-950. In another embodiment, the clearance (Cl; in ml per hour) of DHCQ after administration of the compositions of the present invention ranges from about 400-450, about 400-500, about 400-550, about 400-600, about 400-650, about 400-700, about 400-750, about 400-800, about 400-850, about 400-900, about 400-950, or about 400-1000.

For oral preparations, DHCQ can be used alone or in combination with appropriate additives to make tablets, suspensions, powders, granules or capsules, for example, with conventional additives, such as lactose, mannitol, corn starch, or potato starch; with binders, such as crystalline cellulose, cellulose derivatives, acacia, corn starch or gelatins; with disintegrators, such as corn starch, potato starch, or sodium carboxymethylcellulose; with lubricants, such as talc or magnesium stearate; and if desired, with diluents, buffering agents, moistening agents, preservatives, and flavoring agents.

Pharmaceutically acceptable excipients, such as vehicles, adjuvants, carriers or diluents, are commercially available. Moreover, pharmaceutically acceptable auxiliary substances, such as pH-adjusting and buffering agents, tonicity-adjusting agents, stabilizers, wetting agents and the like, are commercially available. Any compound useful in the methods and compositions of the invention can be provided as a pharmaceutically acceptable base-addition salt. "Pharmaceutically acceptable base-addition salt" refers to those salts that retain the biological effectiveness and properties of the free acids, which are not biologically or otherwise undesirable. These salts are prepared by adding an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Exemplary organic bases are isopropylamine, diethylamine, ethanolamine, trimethylamine, dicyclohexylamine, choline, and caffeine. In some embodiments the salt is chloride or sulfate. In other embodiments the salt is a bidentate salt such as fumaric acid or succinic acid.

The active agent, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The active agents of the present invention or salts thereof may form a solvate and/or a crystal polymorph, and the present invention contains such solvates and crystal polymorphs of various types. A solvate means a solvate of the compound of the present invention or its salt, and example includes solvate of which solvent is alcohol (e.g., ethanol), hydrate, or the like. Example of hydrate includes monohydrate, dihydrate or the like. A solvate may be coordinated with an arbitrary number of solvent molecules (e.g., water molecules). The compounds or salts thereof may be left in the atmosphere to absorb moisture, and a case where adsorbed water is attached or a case where hydrate is formed may arise. Moreover, the compounds or salts thereof may be recrystallized to form their crystal polymorph.

As used herein, compounds that are "commercially available" may be obtained from commercial sources including but not limited to Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen A G (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

Compounds can also be made by methods known to one of ordinary skill in the art. As used herein, "methods known to one of ordinary skill in the art" may be identified through various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

Although specific drugs are exemplified herein, any of a number of alternative drugs and methods apparent to those of skill in the art upon contemplation of this disclosure are equally applicable and suitable for use in practicing the invention. The methods of the invention, as well as tests to determine their efficacy in a particular patient or application, can be carried out in accordance with the teachings herein using procedures standard in the art. Thus, the practice of the present invention may employ conventional techniques of molecular biology (including recombinant techniques), microbiology, cell biology, biochemistry, and immunology within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991); as well as updated or revised editions of all of the foregoing.

The terms "subject," "individual," and "patient" are used interchangeably herein to refer to a mammal being assessed for treatment and/or being treated. In an embodiment, the mammal is a human. The terms "subject," "individual," and "patient" thus encompass humans having pre- or early-stage inflammatory disease. Subjects may be human, but also include other mammals, particularly those mammals useful as laboratory models for human disease, e.g. mouse, rat, cats, dogs, horses, etc.

The expression "body fluid" as used herein in intended to include all of those accessible body fluids usable as clinical specimens which may contain a compound being tested for in sufficient concentration in said fluid to be within the limits of detection of the test device or assay being used. Body fluids will thus include whole blood, serum, plasma, urine, cerebrospinal fluid, synovial fluid, and interstitial and other extracellular fluids, particularly synovial fluid of affected joints. In some embodiments a body fluid used for determination of an abnormal marker of early-stage inflammation is a synovial fluid from a joint suspected of being involved in early arthritis. In other embodiments a body fluid used for marker determination is systemic, e.g. blood, urine, etc.

Care should be exercised in the collection and storage of the fluids to be tested. Steps should be taken to avoid proteolysis of the compounds to be tested for in said fluids, and freezing of the fluids is usually warranted unless the test involved can be carried out within a shortly after the fluids are collected. It is usually preferable to use synovial fluid rather than serum because of the likelihood that there will be greater concentrations of the compounds being tested for in the synovial fluid. On the other hand, increased levels of viscosity in synovial fluids pose problems in immunoassay systems that must be addressed by the artisan. It may be preferable to conduct longitudinal studies of a selection of cytokines and markers as well as their respective inhibitors and binding proteins in order to obtain the most accurate profile possible in determining whether an individual is in the early stages of articular cartilage degeneration and is therefore a candidate for intervention with the methods of the invention.

The methods of the invention can be used for prophylactic as well as therapeutic purposes. As used herein, in one embodiment the term "treating" refers to prophylactic or preventative use of the intervention in individuals with increased risk for or with early-stage inflammatory disease. In such individuals, treatment prevents development of symptoms or signs of disease, prevents development of disease, and/or reverses signs or symptoms of disease. In another embodiment, the term "treating" refers to treating individuals with established disease to reduce symptoms or signs of disease, to prevent disease progression, and/or to reverse symptoms of signs of disease.

Individuals at increased risk for or with early stages of an inflammatory disease are generally asymptomatic, and exhibit no or minimal symptoms and signs of the disease. In some embodiments, individuals at increased risk for developing an inflammatory disease are treated with DHCQ to prophylactically prevent them from developing signs of an inflammatory disease, symptoms of an inflammatory disease, or the inflammatory disease. In some embodiments, individuals at increased risk for developing an inflammatory disease are treated with DHCQ to prevent them from exhibiting progression of signs of an inflammatory disease or symptoms of an inflammatory disease, and/or to prevent them from developing the inflammatory disease. Thus, the invention provides a significant advance in the treatment of at-risk individuals, individuals with pre-clinical findings, or individuals with early-stage disease, by preventing the development of clinical symptoms or signs of a disease or by preventing the progression of the clinical symptoms or signs of a disease. Such treatment is desirably performed prior to the development of clinical symptoms or signs of disease, and before significant loss of function in the affected tissues, i.e. in the "at increased risk" for or "early-stage" inflammatory disease states.

In particular embodiments, the present invention provides for the treatment of humans and other mammals that are at increased risk for, have pre-clinical, or have early-stage inflammatory disease but are asymptomatic, or have early and mild symptoms or signs of the disease—all of these subgroups are referred to herein as patients at increased risk of developing an inflammatory disease or a disease associated with inflammation. In such asymptomatic individuals with pre-clinical or early-stage inflammatory disease, this invention can prevent the development of symptomatic inflammatory disease, prevent the development of signs of the disease, or reduce the progression of early-symptomatic inflammatory disease. In individuals with early symptoms of signs of inflammatory disease, with such early symptoms and signs being present for less than 6 months or being mild in severity, this invention can prevent the development of the full symptoms of an inflammatory disease, prevent the development of signs and features of the disease, or reduce the progression of early-stage inflammatory disease. An aspect of this invention is the treatment of asymptomatic individuals with pre-clinical or early-stage inflammatory disease to prevent them from developing symptomatic inflammatory disease.

In various embodiments, the present invention specifically provides for the treatment of humans and other mammals that have early-stage (which in certain cases and diseases can have mild symptoms, or intermittent symptoms, or symptoms for less than 6 months) or established-inflammatory disease. In such symptomatic individuals with early-stage or established inflammatory disease, this invention can prevent progression of or reduce the severity of the symptoms and signs of the inflammatory disease.

In one embodiment, treatment of individuals at increased risk for development of an inflammatory disease reduced their overall risk for development of the inflammatory disease. Decreasing an individual's risk for development of an inflammatory disease means that for an individual or a group of individuals treated with DHCQ, there will be at least about a 25%, at least about a 35%, at least about a 45%, at least about a 55%, at least about a 65%, at least about a 75%, and may be around or up to about a 50% lower rate of development of the inflammatory disease as compared to the rate of development of the inflammatory disease in individuals not treated with DHCQ (either previously described in the literature for a patient population with similar characteristics, or for individuals treated with alternative therapies).

Developing an inflammatory disease means being formally diagnosed with the inflammatory disease by a physician. Further, developing an inflammatory disease means developing the symptoms, physical exam findings, laboratory test findings, imaging findings, and other findings that meet the established diagnostic criteria for the inflammatory disease and thereby enable a physician to diagnose an individual with the inflammatory disease.

The expression "presently or prospectively" as used herein is intended to mean that in accordance with the methods discussed below of making that determination, it is possible to identify an individual as either being presently in need of such treatment, or very likely or expected to be in need of such treatment in the near-term future. Prospective need of treatment may be established by those determinations of positive factors that from the experience of the artisan lead directly to the early stages of an inflammatory disease.

The expression "at increased risk of developing an inflammatory disease or a disease associated with inflammation" (also referred to herein as "at increased risk") is intended to mean individuals who are asymptomatic but having an increased likelihood for developing such a disease, individuals who have mild symptoms and having an increased likelihood for developing such a disease, individuals who asymptomatic but in the pre-clinical phase of such a disease, individual who have mild symptoms disease but are in the pre-clinical phase of such a disease, individuals who are asymptomatic who are in the early-stages of disease, and individuals who have mild symptoms who are in the early-stages of disease. "Early stages of inflammatory disease" is intended to mean the very beginning of the initial pathologic changes. Said pathologic changes include changes in the composition, form, density, signs and/or inflammatory state and/or metabolic state of the involved tissue or organ as compared to that present in healthy individuals.

Individuals at increased risk for developing an inflammatory disease or a disease associated with inflammation can be treated with DHCQ to prevent the development of disease, to prevent development of signs of the disease, to prevent the onset of symptomatic disease, to prevent progression of signs or symptoms of disease, or to prevent progression of inflammation, or to prevent progression of metabolic abnormalities, or to prevent progression of associated metabolic conditions or diseases. The DHCQ can be orally delivered using tablets, capsules or a suspension.

The retinal toxicity of HCQ significantly limits its medical use to treat humans who are at-risk for, in the pre-clinical stages of, or in the early-stages of an inflammatory disease or disease associated with inflammation. Many physicians are reluctant to treat individuals at-risk, in the pre-clinical stages of, or in the early-stages of an inflammatory disease or disease associated with inflammation with HCQ for years or decades due to the approximately 0.5-1% risk (incidence) for the development of retinal toxicity after about 5 years of treatment, approximately 1% risk of retinal toxicity after about 7 years of treatment, and approximately 2% risk of retinal toxicity after 10-15 years of treatment. Individual humans who are informed by a physician or other healthcare professional that they are in the pre-clinical stages of, or in the early-stages of, an inflammatory disease or disease associated with inflammation are reluctant or unwilling to take HCQ for years or decades to attempt to prevent development of a disease due to the approximately 0.5-1% risk (incidence) for the development of retinal toxicity after about 5 years of treatment, approximately 1% risk of retinal toxicity after about 7 years of treatment, and approximately 2% risk of retinal toxicity after 10-15 years of treatment.

It is the unexpected and surprising finding that DHCQ possesses robust anti-inflammatory efficacy, while possessing minimal retinal cell toxicity, that enables DHCQ to be safely used for years or decades to treat individuals at-risk for an inflammatory disease or disease associated with inflammation to prevent development of that disease. It is the unexpected and surprising finding that DHCQ possesses robust anti-inflammatory efficacy, while possessing minimal retinal cell toxicity, that enables DHCQ to be safely used for years to decades to treat individuals in the pre-clinical stages of an inflammatory disease or disease associated with inflammation to prevent development of or progression of that disease. It is the unexpected and surprising finding that DHCQ possesses robust anti-inflammatory efficacy, while possessing minimal retinal cell toxicity, that enables DHCQ used to be safely used for years to decades to treat individuals in the pre-clinical stages of an inflammatory disease or disease associated with inflammation to prevent development of or progression of that disease. With DHCQ treatment, the rates of retinal toxicity for a cumulative dose similar to that of HCQ, and over a similar dosing period, are expected to be about 30, 40, 50, 60, or 70% lower than the rates of retinal toxicity observed with HCQ therapy. With DHCQ therapy, the rate (incidence) of retinal toxicity after about 5 years of treatment is expected to be less than 0.5%, or less than 0.25%, or less than 0.1%. With DHCQ therapy, the rate of retinal toxicity after about 7 years of treatment is expected to be less than 0.6%, or less than 0.5%, less than 0.25%, or less than 0.1%. With DHCQ therapy, the rate of retinal toxicity after about 10 years of treatment is expected to be less than 1%, or less than 0.75%, or less than 0.5%, less than 0.25%, or less than 0.1%. With DHCQ therapy, the rate of retinal toxicity after about 15 years of treatment is expected to be less than 1.5%, or less than 1%, or less than 0.5%, or less than 0.25%, or less than 0.1%.

In another embodiment, this invention provides for the treatment of individuals with established inflammatory disease. The inflammatory disease is diagnosed based on an individual exhibiting symptoms, signs, clinical features, laboratory test results, imaging test results, marker results, and other findings that enable a physician to formally diagnose that individual with the inflammatory disease. In some embodiment, established inflammatory disease is an inflammatory disease for which an individual has had a formal diagnosis of the disease made by a physician for longer than 6 months. In established inflammatory disease, the signs or symptoms of disease may be more severe. In established inflammatory disease, the disease process may cause tissue or organ damage.

Individuals at increased risk for development of an inflammatory disease, with early-stage inflammatory disease, or with established inflammatory disease can be treated with DHCQ of the invention to prevent the development of disease, to prevent the progression of disease, and to prevent the progression of the symptoms or signs of disease. The dose of DHCQ is generally about 400 mg per day, or about 500 mg per day, or about 550 per day, or about 600 mg per day, or about 650 mg per day, or about 700 mg per day, or about 750 mg per day, or about 800 mg per day, but can vary between 25-1600 mg per day. Inflammatory diseases and diseases associated with inflammation include autoimmune diseases including multiple sclerosis, systemic lupus erythematosus, rheumatoid arthritis, Crohn's disease, psoriasis, autoimmune hepatitis, and other autoimmune diseases; degenerative diseases including osteoarthritis, Alzheimer's disease, macular degeneration and other degenerative diseases; metabolic diseases including type II diabetes, atherosclerosis, coronary artery disease, non-alcoholic steatohepatitis (NASH), hyperlipidemia, insulin resistance, metabolic syndrome, and other metabolic diseases; chronic infections that result in inflammation including human immunodeficiency virus infection, hepatitis C virus infection, cytomegalovirus infection, and other viral, bacterial, fungal, parasite and other infection; and other inflammatory diseases such as fatty liver disease.

The present invention provides a method of treating or preventing degeneration or destruction of articular cartilage or remodeling of the subchondral bone in the joints of an individual in need of such treatment, comprising establishing the status of an individual as presently or prospectively being in said early stages and thus in need of such treatment; and administering to the individual DHCQ, or a combination of DHCQ and atorvastatin, in an amount therapeutically effective for treating or preventing said degeneration or destruction of articular cartilage or subchondral bone. In some embodiments the criteria for treatment further includes evidence of inflammation in the affected joint.

Assessment of OA may use the Kellgren Lawrence (KL) grading system (Kellgren and Lawrence, Ann. Rheum. Dis., 16:494-502, 1957, herein specifically incorporated by reference). The KL grading system relies on an anterior-posterior (AP) radiograph and is as follows: grade 0=no features of OA; grade 1=presence of OA is doubtful, presence of minute osteophyte(s), unchanged joint space; grade 2=minimal OA, definite osteophyte(s), unchanged joint space; grade 3=moderate OA, moderate diminution of joint space; grade 4=severe OA, joint space greatly reduced with sclerosis of subchondral bone. For the purposes of the present invention, the KL score is less than 3, in some embodiments less than 2, and desirably less than one.

The use of DHCQ described herein, in some embodiments, is aimed at intervention during the pre-clinical or early stages of OA, during which there is evidence of only mild cartilage abnormalities or lesions as defined by the presence of at least one abnormal imaging marker indicative of pre-clinical or early-stage OA, as determined by imaging or direct visualization modalities, molecular marker analysis, or clinical history of a condition or event predisposing to the development of OA. The DHCQ therapy of the invention modifies OA disease progression as measured by either stabilization of KL score and/or joint-space narrowing, or prevention of further cartilage breakdown (as assessed by imaging using MRI or another imaging modality), or reduction in levels of molecular markers of cartilage breakdown.

Individuals with pre-clinical or "pre-OA" are those at increased risk of developing OA, as evidenced by abnormal inflammatory markers, abnormal biochemical markers, abnormal imaging markers, or abnormal clinical markers. Conditions or events that predispose to the development of OA include, without limitation, a history of injury to a joint; clinically or radiographically diagnosed meniscal injury with or without surgical intervention; a ligamentous sprain with clinically or radiographically diagnosed anterior or posterior cruciate or medial or lateral collateral ligament injury (Chu et al, Arthritis Res Ther. 2012 14(3):212. PMID: 22682469); clinically measured limb-length discrepancy; obesity with a current, or prolonged historical period of, BMI >27; or biomechanical features of abnormal gait or joint movement. In general, a determination of pre-clinical OA is associated with one or more, two or more, three or more parameters (abnormal markers) of joint pathology including, without limitation and relative to a healthy control sample, cartilage proteoglycan loss; cartilage damage; or elevated levels of degradative enzymes, the presence of products of cartilage or extracellular matrix degradation or bone remodeling. Humans at risk for OA, who have pre-OA, and who have early-stage OA are often asymptomatic, but a subset of patients experience joint pain due to cartilage injury (e.g. meniscal injury), ligamentous injury (e.g. tearing of the anterior cruciate ligament), or another joint abnormality. The joint pain in individuals with pre-OA and early-stage OA is generally intermittent and mild in nature.

Compared to the joints of healthy control individuals, a joint in an individual with pre-clinical OA will exhibit a KL score of 0, and have one, two, three, four or more abnormal markers indicative of pre-clinical disease. MRI-detected imaging markers indicative of the presence of pre-clinical OA include cartilage edema, cartilage proteoglycan loss, cartilage matrix loss, bone marrow edema, articular cartilage fissures, articular cartilage degeneration, a meniscal tear, an anterior cruciate ligament tear, a posterior cruciate ligament tear, and other abnormalities of the cartilage or ligaments in the joint. Ultrasound will show evidence of cartilage edema or damage. Arthroscopy can allow direct detection or visualization of cartilage edema, cartilage softening, cartilage thinning, cartilage fissures, cartilage erosion, or other cartilage abnormalities. Cartilage damage is frequently defined by the Outerbridge classification criteria or similar directly observed changes within the joint. For example, one such scoring system defines the presence of damage is as follows: grade 0=normal cartilage; grade I: softening and swelling of cartilage; grade II: a partial-thickness defect in the cartilage with fissures on the surface that do not reach subchondral bone or exceed 1.5 cm in diameter; grade III: fissures in the cartilage that extend to the level of subchondral bone in an area with a diameter of more than 1.5 cm. Humans at risk for OA or with "pre-clinical OA" may be asymptomatic or have mild symptoms, with have a KL score of 0, but may have signs of cartilage damage, meniscal damage, ligament damage, or other abnormalities of the joint based on MRI imaging, ultrasound imaging, or direct visualization of the joint on arthroscopy.

As compared to joints in healthy individuals, a joint in an individual with early-stage OA will typically exhibit a KL score of 0 or 1 (an abnormal imaging marker), and have one, two, three, four or more abnormal markers indicative of early disease. Plain X-rays of the involved joint would demonstrate features consistent with a KL score of 0-2, including no osteophytes or small osteophytes, and no or minimal joint space narrowing. MRI-detected imaging markers indicative of early-stage OA include cartilage proteoglycan loss, cartilage thinning, cartilage fissures or cartilage breakdown. Ultrasound will show evidence of cartilage edema or damage. Arthroscopy can provide for direct detection or visualization of cartilage edema, cartilage softening, cartilage thinning, cartilage fissures, cartilage erosion, or other cartilage abnormalities. Cartilage damage is frequently defined by the Outerbridge classification criteria or similar direct observational changes within the joint. Humans with early OA may be asymptomatic, or may have mild or intermittent symptoms, or may have symptoms for less than 6 months, but may exhibit findings associated with cartilage damage as represented by Outerbridge grade 0, grade I and grade II scores or similar direct observational changes within the joint, as well as with other cartilage, meniscal and ligament damage based on MRI imaging, ultrasound imaging, or direct visualization of the joint on arthroscopy.

In contrast to pre-clinical (also termed at-risk for) OA and early-stage OA, established or advanced OA can be defined radiographically as KL grade >=2 or as MRI evidence of extensive, complete, or near-complete loss of articular cartilage. Other marker evidence of joint failure can be determined by direct or arthroscopic visualization of extensive, complete, or near-complete loss of joint space or cartilage, by biomechanical assessment of inability to maintain functional joint integrity, or by clinical assessment of joint failure, as evidenced by inability to perform full range of motion or to maintain normal joint function. On physical examination, patients with advanced OA can have abnormal clinical markers including bony enlargement, small effusions, crepitus, and malalignment of the synovial joints. Examples of semiquantitative MRI scoring systems that can be used to classify the severity of OA include: WORMS (Whole-Organ Magnetic Resonance Imaging Score; Peterfy C G, et al. Osteoarthritis Cartilage 2004; 12:177-190); KOSS (Knee Osteoarthritis Scoring System; Kornaat P R, et al. Skeletal Radiol 2005; 34:95-102); BLOKS (Boston Leeds Osteoarthritis Knee Score; Hunter D J, et al. Ann Rheum Dis 2008; 67:206-211); MOAKS (MRI Osteoarthritis Knee Score; Hunter D J, et al. Osteoarthritis Cartilage. 2011; 19(8):990-1002); HOAMS (Hip Osteoarthritis MRI Score; Roemer F W, et al. Osteoarthritis Cartilage. 2011; 19(8):946-62); OHOA (Oslo Hand Osteoarthritis MRI Score). Advanced OA can result in significant joint pain and loss of mobility owing to joint dysfunction.

In a preferred embodiment, the individual treated with the compositions and by the methods of the invention has pre-clinical (at-risk) or early-stage OA or RA. In other embodiments, the individual treated by the methods of the invention has established OA, RA or other type of arthritis.

A variety of markers can be used to assess inflammation in pre-clinical OA, early-stage OA, and advanced OA, including imaging markers, molecular markers, and clinical markers. Examples of abnormal clinical markers include the presence of a joint effusion on physical examination. Another example of an abnormal clinical marker is the presence of morning stiffness in the joint. Examples of abnormal imaging markers include the use of MRI or ultrasound-detected signs of inflammation in the joint. MRI can be performed either with or without gadolinium contrast, and MRI-evidenced inflammation is defined as the presence of one or more of the following findings: synovitis (synovial lining thickening, proliferation, and/or enhancement (increased signal), including a positive Doppler-flow signal in the synovial lining), joint effusion, bone marrow edema, etc (Krasnokutsky et al, Arthritis Rheum. 2011 63(10):2983-91. doi: 10.1002/art.30471 PMID: 21647860; Roemer et al, Osteoarthritis Cartilage. 2010 October; 18(10):1269-74. PMID: 20691796; Guermazi et al, Ann Rheum Dis. 2011 70(5):805-11, PMID: 21187293). Ultrasound-evidenced inflammation (an abnormal imaging marker) is defined as the presence of one or more of the following findings: synovial lining thickening and/or enhancement, a joint effusion, bone marrow enhancement, etc. (Guermazi et al, Curr Opin Rheumatol. 2011 23(5):484-91. PMID: 21760511; Hayashi et al, Osteoarthritis Cartilage. 2012 March; 20(3):207-14. PMID: 22266236; Haugen et al, Arthritis Res Ther. 2011; 13(6):248. PMID: 22189142). Molecular markers that can be used to assess inflammation include erythrocyte sedimentation rate (ESR), CRP, cytokines, chemokines, and other inflammatory mediators. ESR and CRP are measured in blood, and the other molecular markers of inflammation can be measured in blood or synovial fluid.

In one embodiment, one or more of these inflammatory markers including abnormal physical exam markers, abnormal imaging (MRI findings, ultrasound findings) markers, abnormal laboratory markers (CRP, ESR), and other abnormal biomarkers are used to identify individuals with active inflammation that are most likely to respond to treatment with DHCQ, or DHCQ+atorvastatin. In another embodiment, individuals with degenerative meniscal tear of the knee are subjected to MRI analysis of the knee and hs-CRP laboratory testing. If the MRI synovitis score (Guermazi et al., Ann Rheum Dis. 2011 70(5):805-11. PMID: 21187293) is measured to be >5 or the hs-CRP is measured to be >2.5 mg/L, then the individual is determined to be at increased risk for or having early-stage OA and is thus treated with DHCQ. In another embodiment, individuals at increased risk for knee OA who experience intermittent knee pain are subjected to MRI analysis of the knee and hs-CRP laboratory testing. If the MRI synovitis score (Guermazi et al., Ann Rheum Dis. 2011 70(5):805-11. PMID: 21187293) is measured to be >5 or the hs-CRP is measured to be >2.5 mg/L, then the individual is determined to be at increased risk for or having the early-stages of OA and is therefore treated with DHCQ.

In another embodiment, one or more of these same inflammatory markers is used to monitor an individual's response to treatment, to determine if treatment should be continued, or to determine if treatment can be discontinued. For example, individuals at increased risk for OA who are being treated with DHCQ are monitored annually, or every-other year, by MRI and hs-CRP. Individuals, whose MRI synovitis score declines to below 3 or whose hs-CRP declines to below 1 mg/L are identified as having exhibited a positive response to therapy and that their at-risk state, early-disease state, or established disease state has responded well to treatment.

Individuals at increased risk for the development of RA, or with "pre-clinical RA", or with early-stage RA, are identified based on the presence of abnormal inflammatory, abnormal imaging, or abnormal clinical markers indicative of RA. Abnormal markers that suggest an individual has early-stage RA include one or more of the following: presence of one or more swollen joints, presence of anti-CCP or RF antibodies, evidence of synovial enhancement (increased signal) on MRI scan or ultrasound, elevated levels of autoantibodies or cytokines that have can predict the development of RA (as described in Sokolove et al, PLoS One. 2012; 7(5):e35296; Deane et al, Arthritis Rheum. 2010 62(11):3161-72; Gerlag et al, Ann Rheum Dis. 2012 71(5):638-41). Factors that increase an individual's risk of developing RA include one or more of the following: a family history of RA (particularly in a first-degree relative), increased levels of anti-CCP and/or RF autoantibodies, a genetic profile associated with susceptibility to RA, and cigarette smoking (as described in Deane et al, Rheum Dis Clin North Am. 2010 36(2):213-41; Klareskog et al, Semin Immunol. 2011 April; 23(2):92-8).

Individuals are classed as being at risk of developing RA on the basis of their being measured to have specific abnormal biochemical, serologic, genetic, imaging, or clinical markers. The pre-clinical phase of RA is characterized by the presence of abnormal inflammatory markers of RA, including the development of anti-citrullinated protein antibodies (ACPA) and rheumatoid factor (RF) years before the onset of clinically apparent RA. As the onset of clinical apparent disease approaches, the ACPA response spreads, i.e., there is an increase in number of levels of autoantibodies targeting citrullinated proteins. Additionally, there is often a concomitant rise in the level of serum cytokines and chemokines as well as acute phase reactants (including but not limited to ESR and CRP) (Sokolove et al, PLoS One. 012; 7(5):e35296. 2012, PMID: 22662108; Deane et al, Arthritis Rheum. 2010 November; 62(11):3161-72). Thus, "at risk" and "pre-clinical" RA can be defined by the presence of the molecular markers ACPA, RF, elevated cytokines, or combinations of these markers. Additionally, pre-clinical RA including "at risk" could be defined by genetic markers and/or family history. Such genetic markers are considered abnormal markers herein and include but are not limited to the HLA DR4 shared epitope and other genetic polymorphisms, such as PTPN22, PAD4, STAT4, and TRAF1-05.

Early-stage RA is rarely asymptomatic; it most often manifests as pain in and/or stiffness of the small or medium joints, and it can be associated with joint swelling or synovitis. Early-stage RA can be defined by the presence of signs and symptoms and abnormal markers consistent with RA of less than 3-6 months duration and lack of radiographic joint damage as determined by plain X-ray. Early-stage RA is also indicated by the presence of abnormal imaging markers (determined, for example, by MRI or ultrasound, including increased Doppler-flow signal on ultrasound), such as synovial enhancement, bone marrow edema, an effusion, or other findings indicative of inflammation (Gerlag et al, Ann Rheum Dis. 2012 71(5):638-41. PMID: 22387728).

Advanced RA is can be defined as RA of greater than 3-6 months duration and often at last 1 year duration. Radiographic signs of RA (abnormal imaging markers), such as periarticular erosions of the bone, can be detected within 1-2 years of disease onset, and therefore an alternative definition of advanced RA may include evidence of radiographic joint-space narrowing and/or erosions.

Multiple sclerosis is an autoimmune neurologic condition caused by demyelination of neurons as a result of immune injury. It is caused by a direct immunologic attack, mediated by autoreactive T cells and B cells, on protein and lipid components of the myelin sheath.

Individuals with pre-clinical MS are those at increased risk of developing MS, as indicated by abnormal biochemical, serologic, genetic, imaging, or clinical parameters. The pre-clinical phase of MS can be characterized by the presence of abnormal inflammatory markers associated with the later onset of MS, for example autoantibodies that appear several years before the onset of clinically apparent MS. Additionally or alternatively, individuals with pre-clinical MS can have neurologic signs and/or symptoms that alone do not diagnose MS but may be associated with the later onset of clinically apparent MS. Such signs or symptoms include but are not limited to optic neuritis (which generally manifests as loss of vision or decreased vision in one eye), numbness, dizziness, muscle spasms. Symptoms of pre-clinical MS are typically of limited duration but can wax and wane. They may be associated with radiographic changes including but not limited to white-matter lesions as determined by MRI, which often appear as bright areas on T2-weighted MRI. Additionally, pre-clinical MS can be associated with the presence of cerebrospinal fluid (CSF) abnormalities including abnormally high numbers of white blood cells or levels of protein, and/or the presence of oligoclonal bands.

Thus, pre-clinical MS can be defined as the presence of clinical symptoms of early demyelination and/or by the presence of specific autoantibodies in serum or CSF, abnormally high levels of protein or white blood cells in CSF, brain or spinal cord lesions detected by imaging, or combinations of these markers.

Early-stage MS most often manifests as persistent or recurrent neurologic symptoms of demyelination, including but not limited to focal or multifocal numbness, tingling, weakness, loss of balance, or compromised vision including blurry or double vision. Definitive diagnosis of MS requires evidence of 2 or more brain lesions detected by MRI and/or 2 or more episodes of neurologic symptoms lasting at least 24 hours and occurring at least one month apart.

Advanced MS can be defined as MS that has progressed to permanent neurologic disability, usually with non-resolving lesions as detected by MRI. Additionally, MS symptoms may wax and wane in a pattern known as relapsing-remitting MS. This pattern can be seen late into the course of MS, with or without continued accrual of damage in a chronic progressive pattern in which disease progresses with increasing neurologic symptoms without complete recovery from prior lesions.

Atherosclerosis is characterized by accumulation of fatty materials in the arterial wall, resulting in development of fatty plaques, which may rupture and cause vascular occlusion and ischemia. The lesion of atherosclerosis comprises a highly inflammatory milieu characterized by the accumulation of inflammatory cells, including macrophages and to a lesser extent T and B cells, and production of high levels of inflammatory cytokines, chemokines, and MMPs (Libby et al, Nature 2011. 473(7347):3170-25. PMID#21593864). Atherosclerosis is associated with and likely promoted by low-grade inflammation.

Individuals at risk for the development of atherosclerosis are those with known risk factors for atherosclerotic coronary artery disease. Risk factors include traditional risk factors for atherosclerotic heart disease, such as those described in the Framingham Risk Score, and including the following abnormal markers: high blood pressure, cigarette smoking, elevated levels of HDL cholesterol, glucose intolerance, increased age, male sex, and other factors (see D'Agostino R B Sr, Vasan R S, Pencina M J, Wolf P A, Cobain M, Massaro J M, Kannel W B. Circulation. 2008 Feb. 12; 117(6):743-53. PMID: 18212285).

Early-stage atherosclerosis is characterized by early changes in coronary arteries, cerebral arteries, and/or other arteries. Such arterial abnormalities can be visualized through imaging using MRI, CT, angiography, or other methods. Because such early-stage disease does not occlude the involved blood vessels, individuals are asymptomatic and they exhibit normal exercise (treadmill or bicycle) or chemical (persanthine or adenosine or dobutamine) stress test results (based on readouts using radiographic contrast and/or electrocardiogram (EKG) changes suggestive of ischemia).

Advanced atherosclerosis is characterized by symptomatic heart or cardiovascular disease, including angina, myocardial infarction, transient ischemic attacks, and/or stroke due to arterial occlusion. Advanced atherosclerosis manifests as more advanced arterial abnormalities that can be visualized as abnormal imaging markers through imaging using MRI, CT, angiography, and other methods. In addition, with advanced atherosclerosis functional testing with an exercise (treadmill or bicycle) or chemical (persanthine or adenosine or dobutamine) stress test results findings suggestive of ischemia detected by radiographic contrast and/or electrocardiogram (EKG).

In one embodiment, one or more abnormal markers of inflammation are used to identify individuals at increased risk for atherosclerotic disease and exhibiting active inflammation, and thus likely to respond to treatment with DHCQ, or a combination of DHCQ+atorvastatin. In another embodiment, individuals at increased risk for atherosclerotic disease with increased blood cholesterol (total cholesterol >250 mg/dL or LDL >150 mg/dL) are subjected to hs-CRP laboratory testing. If the hs-CRP is >3, then the individual is determined to be at high-risk for progression of atherosclerotic heart disease and is treated with DHCQ, or the combination of DHCQ and atorvastatin.

In another embodiment, hs-CRP is used to monitor an individual's response to treatment with DHCQ, or the combination of DHCQ and atorvastatin, to determine if the individual who is at increased risk for atherosclerotic disease has responded to treatment and/or if the treatment should be continued. For example, individuals at increased risk for atherosclerotic who are being treated with DHCQ, or the combination of DHCQ and atorvastatin, are monitored annually, or every-other year, by repeat cholesterol and hs-CRP testing. Individuals, whose total cholesterol declines below 220, LDL cholesterol declines to below 120, and whose hs-CRP declines to be below 1 are identified as having exhibited a positive response to therapy and that their at-risk state, early-disease state, or established disease state is well-controlled by DHCQ, or combination therapy with DHCQ+atorvastatin.

Type II diabetes mellitus is characterized by the presence of insulin resistance and hyperglycemia, which can cause retinopathy, nephropathy, neuropathy, or other morbidities. Insulin resistance (IR), which is referred to as a disease state herein, is a physiological condition in which cells fail to respond to the normal actions of the hormone insulin. The body produces insulin, but the cells in the body become resistant to insulin and are unable to use it as effectively, leading to hyperglycemia. Beta cells in the pancreas subsequently increase their production of insulin, further contributing to hyperinsulinemia. This often remains undetected and can contribute to a diagnosis of Type 2 Diabetes. Additionally, type 2 diabetes is a well-known risk factor for atherosclerotic cardiovascular disease. Metabolic syndrome refers to a group of factors, including hypertension, obesity, hyperlipidemia, and insulin resistance (manifesting as frank diabetes or high fasting blood glucose or impaired glucose tolerance), that raises the risk of developing heart disease, diabetes, or other health problems; (Grundy et al, Circulation. 2004; 109:433-438). There is a well-characterized progression from normal metabolic status to a state of "insulin resistance" as assess by impaired fasting glucose (IFG: fasting glucose levels greater than 100 mg/dL) or to a state of impaired glucose tolerance (IGT: two-hour glucose levels of 140 to 199 mg/dL after a 75 gram oral glucose challenge). Both IFG and IGT are considered abnormal metabolic markers indicative of a pre-diabetic states, with over 50% of subjects with IFG progressing to frank type II diabetes within, on average, three years (Nichols, Diabetes Care 2007. (2): 228-233). The insulin resistance is caused, at least in part, by chronic low-grade inflammation (Romeo G R et al, Arterioscler Thromb Vasc Biol. 2012 32(8):1771-6; de Luca C et al, FEBS Lett. 2008 582(1):97-105; Ma K et al, Diabetes Metab Res Rev. 2012 28(5):388-94).

Pre-clinical type II diabetes or "at risk" for type II diabetes can be defined as impaired fasting glucose, which is defined as a fasting glucose greater than 100 mg/dL. Humans with impaired fasting glucose levels and who are "at risk" of developing type II diabetes are asymptomatic.

Early-stage type II diabetes is defined by an abnormal fasting blood glucose reading of >126 mg/dL on two separate occasions. Individuals with early-stage type II diabetes do not have symptoms or signs of tissue damage or end-organ damage.

Advanced type II diabetes is characterized by abnormal metabolic markers including persistent elevation in blood glucose levels over 200 mg/dL in a non-fasting state, or multiple readings of >126 mg/dL in the fasting state, and a hemoglobin A1c reading of >7%. Humans with advanced type II diabetes frequently have symptoms, microvascular complications, and/or end-organ or tissue damage.

In one embodiment, measurement of one or more abnormal metabolic and inflammatory markers are used to identify individuals at increased risk for type II diabetes whom have active inflammation, and thus are at highest risk for progression of their type II diabetes and also most likely to respond to treatment with DHCQ, or the combination of DHCQ+atorvastatin. For example, individuals with a body mass index (BMI) greater than 25 are tested for their fasting blood glucose, hemoglobin A1c, and hs-CRP. Individuals who exhibit a fasting blood glucose >126 mg/dL on two separate occasions, and who have either a hemoglobin A1c >6.5% or a hs-CRP >3 mg/L, are identified as exhibiting abnormal metabolic marker(s) and are at highest risk for progression of disease and initiated on therapy with DHCQ, or the combination of DHCQ and atorvastatin.

In another embodiment, one or more of these same metabolic and inflammatory markers are used to monitor an individual's response to treatment, to determine if treatment needs to be continued, or to determine if treatment can be discontinued. For example, individuals at increased risk for type II diabetes who are being treated with DHCQ, or the combination of DHCQ and atorvastatin, are monitored annually, by testing for hemoglobin A1c and hs-CRP. Individuals, whose hemoglobin A1c declines to less than 5.6% and hs-CRP declines to below 1 are identified as having exhibited a positive response to therapy and that their at-risk state, early-disease state, or established disease state has responded well to treatment.

The International Diabetes Federation consensus worldwide definition of the term metabolic syndrome (2006) is based on the following abnormalities in inflammatory markers, metabolic markers and clinical markers: Central obesity (defined as waist circumference# with ethnicity-specific values) AND any two of the following: Raised triglycerides: >150 mg/dL (1.7 mmol/L), or specific treatment for this lipid abnormality; Reduced HDL cholesterol: <40 mg/dL (1.03 mmol/L) in males, <50 mg/dL (1.29 mmol/L) in females, or specific treatment for this lipid abnormality; Raised blood pressure (BP): systolic BP >130 or diastolic BP >85 mm Hg, or treatment of previously diagnosed hypertension; Raised fasting plasma glucose (FPG): >100 mg/dL (5.6 mmol/L), or previously diagnosed type 2 diabetes. The World Health Organization 1999 criteria require the presence of any one of diabetes mellitus, impaired glucose tolerance, impaired fasting glucose or insulin resistance, AND two of the following: Blood pressure: ≥140/90 mmHg; Dyslipidemia: triglycerides (TG): ≥1.695 mmol/L and high-density lipoprotein cholesterol (HDL-C) ≤0.9 mmol/L (male), ≤1.0 mmol/L (female); Central obesity:waist:hip ratio >0.90 (male); >0.85 (female), or body mass index >30 kg/m2; and Microalbuminuria:urinary albumin excretion ratio ≥20 μg/min or albumin:creatinine ratio ≥30 mg/g. Associated diseases and signs are: hyperuricemia, fatty liver (especially in concurrent obesity) progressing to NAFLD, polycystic ovarian syndrome (in women), and acanthosis nigricans. Progression of metabolic syndrome results in frank diabetes or high fasting blood glucose or impaired glucose tolerance, and as a result individuals develop the symptoms and signs of coronary artery disease, type II diabetes, heart disease, diabetes, or other health problems. In one embodiment, DHCQ is used to treat patients with the metabolic syndrome with resultant reduction in serum lipids (inducing reduced total cholesterol, LDL, or triglycerides or alternatively, increased HDL). In another embodiment, DHCQ is used to treat patients with the metabolic syndrome with resultant reduction in insulin resistance as manifest by reduced levels of fasting serum glucose, reduced levels of post-prandial serum glucose, and/or reduction in hemoglobin A1c. In another embodiment, DHCQ is used to treat patients with hyperlipidemia with resultant reduction in total cholesterol, or LDL, or triglycerides or alternatively, increased HDL.

Metabolic syndrome is an inflammatory condition. In the setting of the metabolic syndrome, macrophages accumulate in obese adipose tissue, where they produce TNF and other inflammatory cytokines in response to stimulation with saturated fatty acids and circulating lipopolysaccharide (LPS) (Johnson et al, Cell 2013. 152(4):673-84; Bhargava P et al, Biochem J. 2012 442(2):253-62). Moreover, TNF inhibition can abrogate insulin resistance (Johnson et al, Cell 2013. 152(4):673-84), however this is not practical or safe for long term therapy. Thus, the metabolic syndrome is a metabolic disease which is directly or indirectly associated with co-morbid inflammation. As discussed above, most commonly used anti-inflammatory therapeutics therapies themselves possess potential hepatotoxicity (i.e. corticosteroids, methotrexate, leflunomide, sulfasalazine) or the potential to worsen the components of the metabolic syndrome (i.e. calcineurin inhibitors such as tacrolimus and cyclosporine are associated with hypertension, hyperlipidemia, and diabetes as well as small potential risk of hepatotoxicity).

In one embodiment, one or more metabolic and inflammatory markers are used to identify individuals at increased risk for metabolic syndrome and who have active underlying disease, and thus are at high risk for disease progression and most likely to respond to treatment with DHCQ, or the combination of DHCQ+atorvastatin. For example, individuals with a body mass index (BMI) greater than 25 are tested for two or more of the following metabolic markers: fasting blood glucose, hemoglobin A1c, total cholesterol, LDL cholesterol, HDL cholesterol, triglycerides, and blood pressure. Individuals who have a fasting blood glucose >126 on two occasions, and at least 1 of the following signs or findings, or at least 2 of the following signs or findings, or at least 3 of the following signs or findings, are identified as having abnormal metabolic marker(s) and thus being at high-risk for development of metabolic syndrome and are initiated on treatment with DHCQ, or the combination of DHCQ+atorvastatin. Signs or findings include but are not limited to the following abnormal inflammatory markers, metabolic markers, and clinical markers: Blood pressure: ≥140/90 mmHg; Triglycerides (TG): ≥1.695 mmol/L and high-density lipoprotein cholesterol (HDL-C) ≤0.9 mmol/L (male), ≤1.0 mmol/L (female); or Microalbuminuria:urinary albumin excretion ratio ≥20 µg/min or albumin:creatinine ratio ≥30 mg/g.

In another embodiment, one or more of these same metabolic and inflammatory markers are used to monitor an individual's response to DHCQ treatment or to DHCQ+atorvastatin treatment, to determine if treatment should be continued, or to determine if treatment can be discontinued. For example, individuals at increased risk for metabolic syndrome who are being treated with DHCQ, or the combination of DHCQ and atorvastatin, are monitored annually. Individuals, who exhibit one or more of the following are identified as having exhibited a positive response to therapy: fasting blood glucose returns to less than 126 mg/dL, hemoglobin A1c declines to less than 5.6%, blood pressure becomes less than 140/90 mmHg, triglycerides (TG) below 1.695 mmol/L, high-density lipoprotein cholesterol (HDL-C) increases, and microalbuminuria:urinary albumin excretion ratio normalizes. Individuals who exhibit a positive response to therapy based on improvement in one or more signs and findings are identified as having exhibited a positive response to therapy, and that their at-risk state, early-disease state, or established metabolic disease state has responded well to treatment with DHCQ, or to treatment with DHCQ+atorvastatin.

Non-alcoholic fatty liver disease (NAFLD) and non-alcoholic steatohepatitis (NASH) are conditions associated with fatty infiltration of (or accumulation in) the liver. Although fatty infiltration alone does not cause liver damage, when it is accompanied by an inflammatory reaction it can lead to fibrosis and liver cirrhosis and ultimately hepatic failure. The inflammation in NASH is characterized by infiltration of the liver by macrophages and lymphocytes, as well as alterations in the liver's macrophage-like Kupfer cell population (Tilg, et al, 2010. Hepatology. 52(5):1836-46). Inflammatory cytokines, particularly TNF, are central to the pathology of NASH. The source of TNF is unclear: it may be peripheral, i.e., inflammatory adipose tissue, or local, i.e., innate immune cells activated by portal-derived endotoxin or by free fatty acid (Tilg et al, 2010. Hepatology. 52(5): 1836-46). The endotoxin-responsive TLR4 receptor has been shown to be critical to disease in a mouse model of NASH (Tsukumo et al, Diabetes 2007. 56(8):1986-98).

There are no currently approved drug treatments for NASH. Diet modification, weight loss, and gastric bypass resulting in the prior have shown the most efficacy in treatment of NASH. Small to moderate sized studies of metformin, pioglitazone, and vitamin E have shown small but significant benefits. However, results have not been consistent with many studies ultimately failing to show an ultimate change in fibrosis (Schwenger K J P, World J Gastroenterol. Feb. 21, 2014; 20(7): 1712-1723.). Given that inflammation is a major component of NASH, it would be anticipated that anti-inflammatory or immunosuppressive therapies could offer efficacy in the treatment of NASH. However, most commonly used anti-inflammatory and immunosupressive therapies themselves possess potential hepatotoxicity. For instance, corticosteroids are associated with development of hepatic steatosis and non-steroidal anti-inflammatory agents are associated with cholestasis and are contraindicated in the setting of cirrhosis. Similarly other drugs commonly used in systemic inflammatory diseases including methotrexate, leflunomide, and sulfasalazine are not uncommonly associated with hepatotoxicity. Likewise, other commonly used immunosuppressants are associated with many of the common co-morbidities seen in patients with NASH. For example, calcineurin inhibitors such as tacrolimus and cyclosporine are associated with hypertension, hyperlipidemia, and diabetes as well as small potential risk of hepatotoxicity.

Pre-clinical NASH or "at risk" for NASH can be defined as NAFLD, which is the presence of fatty infiltration of the liver on ultrasound (an abnormal imaging marker) in the absence of alcohol consumption or exposure to other liver toxins. The abnormal imaging marker of fatty infiltration of the liver is assessed by ultrasound imaging of the liver, and determination that an individual patient exhibits ultrasound results consistent with fatty infiltration of the liver which are outside of the range of ultrasound findings in 95% of normal humans. Humans with NAFLD and who have pre-clinical NASH (i.e., NAFLD) have normal levels of liver enzymes in their blood (e.g. normal aminotransferase [transaminase] levels, including a normal AST (SGOT) and ALT (SGPT)).

Early-stage NASH is defined as the presence of NAFLD in conjunction with hepatic inflammation and injury, as reflected by abnormally high levels of blood aminotransferases (i.e., elevated levels of AST (SGOT) and ALT (SGPT) as compared to the normal range in humans—which represent abnormal markers of inflammation for NASH).

Advanced NASH is defined as the presence of chronic liver inflammation and injury, as reflected by persistently elevated levels of liver transaminases (persistently elevated AST (SGOT) and ALT (SGPT)), and the presence of early or advanced hepatic fibrosis and/or cirrhosis. Hepatic fibrosis is identified by ultrasound or CT or MRI imaging of the liver, or by liver biopsy.

In one embodiment, measurement of one or more abnormal metabolic markers, abnormal inflammatory markers, and abnormal imaging markers are used to identify individuals at increased risk for subsequent development of NAFLD or NASH, and thus are most likely to respond to treatment with DHCQ, or the combination of DHCQ and atorvastatin. For example, individuals with elevated liver transaminases, based on AST >60 IL/L (normal range 6-40 IU/L) or ALT >50 IU/L (normal range 7-35 IU/L), ultrasound findings indicative of fatty liver, and a fasting blood glucose >126 on two separate readings, or hemoglobin A1c >6.5%, are identified as exhibiting abnormal inflammatory markers, abnormal imaging markers or abnormal metabolic markers and therefore being at high risk for progression to NASH and initiated on therapy with DHCQ, or the combination of DHCQ and atorvastatin.

In another embodiment, one or more of these same metabolic and inflammatory markers are used to monitor an individual's response to treatment, to determine if the individual has exhibited a positive response to therapy, or to determine if treatment can be discontinued. For example, individuals at increased risk for NAFLD or NASH who are being treated with DHCQ, or the combination of DHCQ and atorvastatin, are monitored periodically, by testing for AST, ALT, hemoglobin A1c and fasting blood glucose. Individuals, whose AST and ALT normalize, whose hemoglobin A1c declines to less than 5.6%, and whose fasting blood glucose normalizes are identified as having exhibited a positive response to therapy, and that their at-risk state, early-disease state, or established disease state has responded well to treatment.

Given the co-occurrence of hyperlipidemia and insulin resistance in the metabolic syndrome, DHCQ could provide a unique and unexpected role as an anti-inflammatory and anti-metabolic which would be well tolerated in the demographic of patients affected by or at risk for development of metabolic syndrome. A potential risk to use of HCQ for treatment of metabolic syndrome would be potential retinal toxicity associated with use of HCQ in the setting of type 2 diabetes. Current recommendations are that HCQ be used with caution or avoided in those with increased risk for retinal toxicity, including those with underlying retinal disease, those with diabetes, the overweight, or those over age 60. Thus, the identification of an agent in possession of the immunomodulatory and metabolic properties of HCQ but with reduced risk of retinal toxicity could provide a viable therapeutic for the metabolic syndrome, including both its metabolic and inflammatory components. An example would be treatment of a patient with metabolic syndrome with DHCQ which would potentially allow not only adequate initial dosing of therapy but could additionally allow dose titration to a level which achieves clinical efficacy, including dosing at level higher than the recommended dose limitations for HCQ. Anticipated results would be suppression of systemic inflammation with concomitant reductions in serum lipids and improvement in insulin sensitivity as well as reduction or normalization of hepatic enzymes in the setting of concurrent NASH.

The disclosed compositions and methods involving DHCQ can also be used to treat alcoholic steatohepatitis. Prolonged consumption of significant amounts of alcohol can result in a range of symptoms from simple steatosis to cirrhotic liver failure. In fact, nearly 90% of individuals who consume more than 60 grams of alcohol a day develop will develop fatty infiltration of the liver. This steatosis can progress to chronic alcoholic hepatitis which can range from mild and chronically progressive disease to a severe and fulminant necrohepatitis. Though the mechanisms of alcoholic hepatitis are likely multifactorial, there is a role for inflammation involving multiple pathways including the innate immune receptors as well as cytokines such as TNF$\alpha$ and IL-1$\beta$. Acute alcoholic hepatitis has been treated with a range of anti-inflammatory therapies including corticosteroids as well as TNF$\alpha$ blockers (O'Shea et al, Alcoholic Liver Disease, Hepatology, 2010, 51(1):307-28). Though potentially effective in the acute setting of severe alcoholic hepatitis, the risk-benefit profile of such therapies prohibits use for chronic alcoholic steatohepatitis. Given the critical role for inflammation including innate immune activation via TLRs, the disclosed compositions and methods involving DHCQ can also be used to treat chronic alcoholic steatohepatitis. This is particularly critical as hepatic insufficiency is a risk factor for retinal toxicity with hydroxychloroquine and thus a drug with a wider therapeutic window with respect to retinal toxicity would be preferred.

The following provides examples of approaches to determining whether inflammation is present in an individual, including individuals at risk for a variety of different inflammatory diseases, such as autoimmune diseases (e.g., RA, MS, Crohn's disease, psoriasis, etc), degenerative diseases involving low-grade inflammation (e.g., OA, Alzheimer's disease, macular degeneration, etc), other inflammatory diseases (e.g., NASH, type II diabetes, metabolic syndrome, atherosclerosis, cardiac disease, etc.), as well as inflammatory diseases associated with chronic inflammation (e.g., HIV infection, HCV infection, CMV infection, TB infection, etc.). Although the following describes the approach to identifying inflammation particularly in humans at risk of developing arthritis or with early-stage arthritis, in another embodiment it is use to assess disease activity or tissue or organ damage in individuals with established inflammatory disease.

A variety of markers can be used to assess inflammation in inflammatory diseases, including imaging markers, molecular markers, and clinical markers. Measurement or detection of abnormal levels or values or findings of such markers can facilitate identification of individuals at increased risk of developing or in an early-stage of an inflammatory disease or disease associated with inflammation, and can be used to identify individuals who would benefit from treatment with DHCQ, or DHCQ+atorvastatin.

Many inflammatory diseases and diseases associated with inflammation, including those described above, are associated with metabolic abnormalities, as reflected by abnormal metabolic marker levels or values. Most anti-inflammatory/ immunosuppressive therapies which would be used to treat such disorders also lack significant capability to ameliorate the metabolic abnormalities observed with inflammatory disease and many, including corticosteroids, and calcineurin inhibitors can themselves induce metabolic abnormalities including insulin resistance, hypertension, and hyperlipidemia. Similarly, given the increased risk of underlying liver disease due to NAFLD/NASH among those with metabolic syndromes, immunosuppressives such as methotrexate and leflunomide should be avoided due to their potential intrinsic hepatotoxicity. Similarly, HCQ, which may have a favorable metabolic profile is itself associated with risk of retinal toxicity and thus should be used cautiously or avoided in those at increased risk for underlying retinal disease including those with type 2 diabetes. Thus use of DHCQ has a unique ability to treat not only inflammation but also the metabolic components of inflammatory disease including but not limited to insulin resistance, hyperlipidemia, and NASH. And DHCQ can do so with a reduced risk of retinal toxicity. Thus, in one embodiment, DHCQ could be used to treat inflammation with associated metabolic disease including but not limited to insulin resistance, type 2 diabetes, hyperlipidemia, and NAFLD and/or NASH. In another embodiment, DHCQ could be used to treat inflammation with associated metabolic disease which placed the patient at increased risk for retinal toxicity. Such properties of DHCQ are unexpected in that both reduced retinal toxicity and favorable metabolic effects are lacked by the other metabolites of the parent molecule HCQ.

A comprehensive description of the markers (including inflammatory markers, metabolic markers, clinical markers and imaging markers) for OA and RA are presented as an example of how one approaches developing markers for a pre-clinical or early-stage inflammatory disease in general. In arthritis, examples of abnormal clinical markers include warmth, erythema (redness), inflammation, and effusions. Other examples of abnormal clinical markers are morning stiffness in the joint lasting more than 1 hour, and pain and swelling. Examples of abnormal imaging markers include MRI- or ultrasound-detected inflammation in the joint. MRI, performed with or without gadolinium contrast, detects inflammation (an abnormal imaging marker) on the basis of the presence of one or more of the following findings: synovitis (synovial lining thickening, proliferation and/or enhancement (increased signal on Gd-MRI)); increased Doppler-flow signal in the synovial lining); a joint effusion; extensive bone marrow edema; and other findings suggestive of inflammation. When ultrasound is the imaging method used, inflammation (an abnormal imaging marker) is defined by the presence of one or more of the following findings: synovial lining thickening and/or enhancement, a joint effusion, bone marrow enhancement, and other findings suggestive of inflammation. Molecular markers that can be used in assessing inflammation include ESR, CRP, cytokines, chemokines, and other inflammatory mediators. ESR and CRP are measured in blood, and the other molecular markers of inflammation can be measured in blood or synovial fluid. Use of molecular markers in blood for identifying individuals with pre-clinical RA or early-stage RA is described in Sokolove et al. (PLoS One. 2012; 7(5):e35296) and Deane et al. (Arthritis Rheum. 2010 62(11):3161-72.).

The presence of pre-clinical and early-stage inflammatory disease may be determined or confirmed by a difference in level of a molecular and inflammatory markers in body fluids, including without limitation synovial fluid, or joint tissue relative to that in a control body fluid or joint tissue from individuals free of arthritis. Examples of such changes in levels of molecular markers in pre-clinical and early-stage OA and RA are the following: increase in level of interleukin-1 beta (IL-1β); increase in level of TNF; increase in ratio of IL-1β to IL-1 receptor antagonist protein (IRAP); increase in expression of p55 TNF receptors (p55 TNF-R); increase in level of interleukin-6 (IL-6); increase in level of leukemia inhibitory factor (LIF); altered levels of insulin-like growth factor-1 (IGF-1), increase in levels of transforming growth factor beta (TGFβ), platelet-derived growth factor (PDGF), or basic fibroblast growth factor (b-FGF); increase in level of keratan sulfate; increase in level of stromelysin; increase in ratio of stromelysin to tissue inhibitor of metalloproteases (TIMP); increase in level of osteocalcin; increased alkaline phosphatase; increased cAMP responsive to hormone challenge; increased urokinase plasminogen activator (uPA); increase in level of cartilage oligomeric matrix protein; increase in level of collagenase; increase in level of other cytokines; increase in in level of CRP; or increase in level of autoantibodies against synovial joint proteins or other biomolecules. The term "metalloprotease" as used herein is intended to refer to MMPs, especially those whose levels are typically elevated concentrations where there is articular cartilage degeneration, i.e., stromelysins, collagenases, and gelatinases. Aggrecanase is also included within this term. The three collagenases present in articular cartilage during the early stages of degeneration are collagenase-1 (MMP-1), collagenase-2 (MMP-8), and collagenase-3 (MMP-13). Of the three stromelysins, stromelysin-1 (MMP-3), stromelysin-2 (MMP-10), and stromelysin-3 (MMP-11), only stromelysin-1 appears in articular cartilage during the early stages of its degeneration. The metalloproteases are secreted by chondrocytes as proenzymes, which must be activated before they can degrade extracellular matrix macromolecules.

A reference range for such molecular markers of inflammation is defined as the set of values within which 95 percent of the normal population falls. If the value or level of a molecular marker of inflammation in an individual patient is outside the set of values or levels within which 95 percent of the normal population falls, then the marker is considered to exhibit an abnormal level in that patient (e.g. that patient is determined to have an "abnormal marker" or an abnormal molecular marker of inflammation).

IL-1, which exists as IL-1α and IL-1β, is a catabolic cytokine that mediates articular cartilage injury and loss in mammalian joints. It suppresses the synthesis of type II collagen found in articular cartilage, while promoting the synthesis of type I collagen characteristic of fibroblasts; induces the production of enzymes involved in matrix degradation; and suppresses the ability of chondrocytes to synthesize new proteoglycans. IL-1 and its modulator IRAP are produced in an autocrine and paracrine fashion by synovial macrophages, and IRAP production may increase in the presence of granulocyte macrophage colony-stimulating factor (GM-CSF). However, IL-1 is much more potent than IRAP, with approximately 130-fold more IRAP being required to abolish the pathogenic effects of IL-1, as measured in chondrocytes and cartilage explants. Imalances between IL-1 and IRAP exacerbates the degeneration of articular cartilage. Consequently, it is also appropriate to identify abnormalities in the levels of IL-1 and IRAP, as well as in the ratio of IL-1 to IRAP, to identify an individual in the early stages of cartilage injury and loss before focal cartilage loss can be identified radiographically. Thus, determining the levels of IL-1 and IRAP, as well as the ratio of IL-1 to IRAP, could enable identification of individuals that are candidates for early pharmacological intervention before significant cartilage degeneration occurs. Furthermore, the frequency of IL-1α- and IL-1β-secreting macrophages is significantly greater in the synovial fluid and synovial tissue of joints undergoing the early stages of articular cartilage degeneration can be detected and is significantly greater than in synovial fluid and synovial tissue from normal joints, i.e., joints in which there is no articular cartilage degeneration.

In mammals subjected to sectioning of the cruciate ligament of a knee joint, the concentration of TNF is statistically higher in the synovial fluid of the sectioned knee joint than in that of the contralateral, unsectioned knee joint. The expression of p55 TNF receptors (TNF-R) on chondrocytes in articular cartilage is also higher in the sectioned knee joint. Therefore, because an increase in TNF levels, and possibly TNF signaling, is associated with early cartilage injury and loss, it is appropriate to measure levels of TNF and TNF-R in the joints of individuals at risk for cartilage degeneration and loss. These results contribute to diagnostic classification of individuals that are candidates for early pharmacological intervention before significant cartilage degeneration occurs.

IL-6 is an inflammatory cytokine whose levels are abnormally high (statistically elevated) in the joints and synovial fluid of damaged limbs as compared to healthy joints and synovial fluids. IL-6 increases the expression of TNF-R on chondrocytes and the production of proteoglycan by chondrocytes; it also induces the release of glycosaminoglycans from the cartilage matrix. Comparing IL-6 levels in synovial fluid and chondrocytes of joints in the early stages of articular cartilage injury and loss to that in synovial fluid and chondrocytes of control joints can identify individuals that are appropriate candidates for pharmacological treatment, before any focal cartilage loss is detectable by radiographic examination.

LIF is produced by monocytes, granulocytes, T cells, fibroblasts, and other cell types associated with inflammatory conditions. Synoviocytes and chondrocytes synthesize and secrete LIF in the presence of IL-1β and TNFα. Thus, identifying increases in levels of LIF can allow selection of candidates for pharmacologic treatment of the early stages of articular cartilage injury and loss.

IGF exists as types I and II, and IGF-I mediates cartilage synthesis. Furthermore, it reduces degradation and promotes synthesis of proteoglycans even in the presence of IL-1β and TNFα. Serum levels of IGF-1 are maintained by high-affinity binding proteins (IGF-BPs), and IGF-1 regulates both bone and cartilage turnover. Detecting abnormally high levels of IGF-1 permits identification of candidates for early pharmacologic treatment of articular cartilage degeneration.

TGFβ is produced by chondrocytes and acts as a powerful mitogen contributing to the turnover of both cartilage and bone. Further, it stimulates the synthesis of extracellular matrix and has anti-inflammatory activity. It also inhibits the degradation of the extracellular matrix by stimulating the production of protease inhibitor, and blocking the release of collagenases and metalloproteases. Further still, it promotes cartilage repair by stimulating production of collagen, fibronectin, inhibitors of plasminogen activators, and tissue inhibitors of metalloproteases (TIMP) by various cells in the mammal joint. Synovial fluid levels of TGFβ are abnormally low in the joints of mammals in the early stages of articular cartilage injury and loss. Consequently, levels of TGFβ compared to control permit diagnostic evaluation of candidates for early pharmacologic treatment of articular cartilage degeneration.

With progressive degeneration, i.e., catabolism of the articular cartilage in the joint, a number of metabolites are produced that are useful as markers of the cartilage degeneration, both to the occurrence and to the progression of cartilage degeneration. For example, IL-1α and IL-1β or TNFα active inflammatory and degradative pathways that mediate cartilage degradation and release of glycosaminoglycans (GAGS), which can be measured in the synovial fluid of an individual. Furthermore, GAG levels change after treatment so that it is possible to monitor the efficacy of pharmacologic intervention, by using GAG levels in synovial fluid as a marker of articular cartilage turnover. Because the degradation of articular cartilage involves collagen as well as the other cartilage components, several collagen breakdown products serve as markers of cartilage degradation in mammals. Type-II-specific collagen breakdown products, e.g., 20-30 amino acid neoepitopes, can be identified in body fluids such as synovial fluid, plasma, serum, and urine. The presence of collagen neoepitopes in these body fluids may be used as indicators of OA onset and progression.

The presence or an increase in the levels of 5D4, a neo-epitope of the GAG keratan sulfate, in synovial fluid is a marker of early articular cartilage injury and loss. Conversely, presence of or increased levels of various neo-epitopes of chondroitin sulfate, another GAG, is associated with anabolic events in the articular cartilage of mammals in the early stages of cartilage injury and loss. Levels of these epitopes in synovial fluid, particularly 3B3, 7D4 and 846, can be determined by specific monoclonal antibodies. The 3B3 epitope is expressed on chondroitin sulfate chains of cartilage during repair and remodeling of the extracellular matrix, and consequently its levels in synovial fluid correlate inversely with those of 5D4. The determination of 3B3 levels in the synovial fluid of test mammals and comparison of these levels with control values permits the creation of a diagnostic profile of a mammal that is an appropriate candidate for early pharmacologic treatment.

Additional markers of cartilage anabolism are the propeptides of type II procollagen (PIIP). Type II collagen is the major collagen of articular cartilage and is produced by chondrocytes as the procollagen PIIP. During the process of collagen fibril formation, aminopropeptide and carboxypropeptide, the noncollagenous portions of PIIP, are cleaved and released into body fluids, where they can be measured as a reflection of anabolic activity in articular cartilage. Levels of the carboxypropeptide of PIIP (carboxy-PIIP) in synovial fluid are higher during cartilage anabolism and correlate with radiographic evidence of pathologic changes in the cartilage. Accordingly, detection of increased levels of carboxy-PIIP in synovial fluid identifies individual for early pharmacologic treatment.

Perturbation of the stromelysin:TIMP ratio in articular cartilage and joint fluids of mammals is another marker of early-stage articular cartilage degeneration. Abnormal joint loading after joint injury causes the production of excess stromelysin, an enzyme produced by chondrocytes and synoviocytes in an IL-1-mediated process. The concentrations of stromelysin are higher in fibrillated (injured) cartilage than they are in cartilage more distal to the injury. Levels of stromelysin may be excessively high for only a short period of time, but where the damage to the joint transcends the tidemark zone of the articular cartilage and reaches into the subchondral bone, there is a substantial likelihood of subsequent articular cartilage degeneration, usually preceded by a stiffening of the subchondral bone. In such situations, there is an increased number of cells involved in the synthesis of stromelysin, IL-1α, IL-1β, and the oncogene proteins c-MYC, c-FOS, and c-JUN. In the synovium cells that secrete these factors are the superficial synovial lining cells, while in the cartilage such cells are the chondrocytes in the superficial and middle layers and the condrocytes in the fibrillated areas of the tibial plateau. Further, stromelysin and IL-1 diffuse into the cartilage matrix of the tibial plateau. Stromelysin, which degrades components of connective tissue, including proteoglycans and type IX collagen, is actively synthesized in the synovium of mammals in the early stages of articular cartilage degeneration, and is the primary proteolytic enzyme involved in the cartilage destruction. Increased levels of stromelysin mRNA are detectable in the synovia of such mammals, as are increased levels of collagenase mRNA. Increased levels of both isoforms of IL-1, but especially IL-1β, stimulate the synthesis of stromelysin and collagenase by synovial fibroblasts. IL-1 does not stimulate the production of tissue inhibitor of metalloprotease (TIMP), such that the levels of this metalloprotease inhibitor in the synovium remain unchanged while the levels of metalloproteases are dramatically increased. The above text represents a detailed description is for OA and RA, but the approach, the types of markers, and a subset of the markers are relevant for a wide spectrum of inflammatory diseases, and these descriptions are meant to serve as an example of how one approaches developing markers for a pre-clinical or early-stage inflammatory diseases in general.

In some embodiments the methods of the invention comprise a step of determining the presence of early-stage inflammatory disease in an individual or susceptibility to development of inflammatory disease prior to treatment, and thus indicating a need of treatment. The method may further include determining the presence of inflammation, prior to the administering step, where an individual at increased risk or in an early stage of an inflammatory disease showing signs of inflammation, particularly inflammation of the relevant organ is selected for treatment with DHCQ, or the combination therapy of DHCQ and atorvastatin. The markers relevant to each disease are presented in the descriptions of each of the diseases. Such markers include clinical markers, metabolic markers, inflammatory markers, imaging markers, research markers, and other markers, with distinct subsets of markers being relevant for different diseases. The markers are considered abnormal when their levels or values or results are outside the distribution of levels, values or results observed for 95% of the healthy population. Individuals with abnormal levels of disease-specific inflammatory markers, metabolic markers, clinical markers, imaging markers, or other markers are at increased risk for developing or in the early stages of an inflammatory disease or disease associate with inflammation.

In some embodiments, the treatment with DHCQ, or the combination of DHCQ and atorvastatin, prevents the development of disease. In some embodiments the treatment with DHCQ, or the combination of DHCQ+atorvastatin, prevents the progression of signs or symptoms of an inflammatory disease. In some embodiments the treatment with DHCQ, or the combination of DHCQ+atorvastatin, results in the early signs or symptoms of an inflammatory disease returning to normal. In some embodiments, treatment with DHCQ, or a combination of DHCQ and atorvastatin, results in normalization of inflammatory markers. In some embodiments the treatment with DHCQ, or the combination of DHCQ+ atorvastatin, prevents development of organ or tissue damage. In some embodiments the treatment with DHCQ, or the combination of DHCQ and atorvastatin, results in stabilization or normalization of laboratory test, imaging markers, or other markers of disease.

In yet other embodiments, the treatment with DHCQ, or a combination of DHCQ and atorvastatin, is used to treat established disease in an individual exhibiting elevated inflammatory markers (abnormal inflammatory markers). In some embodiments, treatment of established inflammatory disease with DHCQ, or the combination of DHCQ and atorvastatin, results in normalization of inflammatory markers and other disease markers. In some embodiments the treatment with DHCQ, or the combination of DHCQ and atorvastatin, results in stabilization or normalization of laboratory test, imaging markers, or other markers of the disease. In some embodiments the treatment with DHCQ, or the combination of DHCQ and atorvastatin, prevents development of organ or tissue damage.

Various techniques and reagents can be used in the analysis of inflammatory markers in the present invention. In one embodiment of the invention, blood or synovial fluid samples, or samples derived from blood, e.g. plasma, serum, etc., are assayed for the presence of specific biomarkers. Other sources of samples are body fluids such as synovial fluid, lymph, cerebrospinal fluid, bronchial aspirates, saliva, milk, urine, and the like. Also included are derivatives and fractions of such cells and fluids. Diagnostic samples are collected any time that an individual is suspected of having an inflammatory disease or of being at risk of developing an inflammatory disease. Such assays come in many different formats, including autoantigen arrays; enzyme-linked immunosorbent assays (ELISA) and radioimmunoassays (RIA); assays in which binding of labeled peptides in suspension or solution are measured by flow cytometry or mass spectrometry.

Many such methods are known to one of skill in the art, including ELISA, fluorescence immunoassays, protein arrays, eTag system, bead-based systems, tag or other array-based systems, surface plasmon resonance (SPR)-based detection systems, etc. Examples of such methods are set forth in the art, including, inter alia, chip-based capillary electrophoresis: Colyer et al. (1997) J Chromatogr A. 781 (1-2):271-6; mass spectroscopy: Petricoin et al. (2002) Lancet 359: 572-77; eTag systems: Chan-Hui et al. (2004) Clinical Immunology 111:162-174; microparticle-enhanced nephelometric immunoassay: Montagne et al. (1992) Eur J Clin Chem Clin Biochem. 30(4):217-22; the Luminex XMAP bead-array system (www.luminexcorp.com); and the like, each of which are herein incorporated by reference.

For multiplex analysis, arrays containing one or more detection antibodies that recognize biomarkers of interest can be generated. Various immunoassays designed to quantitate the biomarkers may be used in screening. Measuring the concentration of the target protein or other biomarker in a sample or fraction thereof may be accomplished by a variety of specific assays. For example, a conventional sandwich-type assay may be used in an array, ELISA, RIA, bead array, etc. format.

The analysis of a biological sample may be done by using any convenient protocol, for example as described below. The readout may be a mean, average, median or the variance or other statistically or mathematically derived value associated with the measurement. The readout information may be further refined by direct comparison with the corresponding reference or control readout.

Following quantitation of the marker in the sample being assayed, the value obtained is compared with a reference or control value to make a diagnosis regarding the phenotype of the patient from whom the sample was obtained. Typically a comparison is made with the analogous value obtained from a sample or set of samples from an unaffected individual. Additionally, a reference or control value may be a value that is obtained from a sample of a patient known to have an autoimmune or degenerative disease of interest, such as RA or OA, and therefore may be a positive reference or control profile.

For prognostic purposes, an algorithm can be used that combines the results of determinations of multiple antibody specificities and/or cytokine levels, and/or levels of cartilage degeneration markers, and/or other markers, and that will identify individual with abnormal levels of such markers and thus discriminate robustly between individuals with increased risk for developing or with established autoimmune disease, e.g. RA, or degenerative disease, e.g. OA, and controls.

Examples of molecular markers of inflammation (also termed markers of inflammation) include c-reactive protein (CRP), high-sensitivity CRP (hs-CRP) (or regular CRP), erythrocyte sedimentation rate (ESR), serum amyloid A, serum amyloid P, fibrinogen, cytokines in blood or other biological fluids, a cytokine, an antibody (such as an autoantibody, or an anti-microbial antibody), a DNA sequence, a RNA sequence (for example, mRNA encoding one or more cytokines or other immune molecules), other markers of inflammation, or combinations thereof.

C reactive protein (CRP), including high-sensitivity CRP (hs-CRP) are included as a marker of inflammation and provide utility as a marker in a variety of inflammatory diseases. It is known that individuals with high levels of hs-CRP (abnormal levels, e.g. an abnormal inflammatory marker), even at the high end of the normal range, have 1.5 to 4 times increased risk of developing an inflammatory disease or disease associated with inflammation, including but not limited to atherosclerotic disease, atherosclerotic cardiovascular disease, RA, psoriatic arthritis, systemic lupus erythematosus, osteoarthritis, type II diabetes, metabolic syndrome, NAFLD, NASH and other inflammatory metabolic diseases. The American Heart Association and U.S. Centers for Disease Control and Prevention have defined risk groups based on hs-CRP levels as follows:

Low risk: hs-CRP less than 1.0 mg/L
Average risk: hs-CRP 1.0 to 3.0 mg/L (which represents an abnormal inflammatory marker)
High risk: hs-CRP above 3.0 mg/L (which represents an abnormal inflammatory marker)

The range of levels of plasma fibrinogen that is deemed normal varies from laboratory to laboratory but is typically 1.5-4.0 g/L. Levels of plasma fibrinogen above 2.8 g/L are considered an abnormal inflammatory marker and are associated with increased risk of developing an inflammatory disease, and levels >4 g/L are associated with an even higher risk.

Normal levels of serum amyloid A (SAA) range widely. However, elevations in SAA levels have been associated with increased risk of inflammatory disease with moderate elevation (>3.9 but <8 mg/L; an abnormal SSA [inflammatory marker] level) conferring increase risk over the lowest tercile, and values greater than 8.2 mg/L (highest tercile; an abnormal SSA [inflammatory marker] level) imparting highest risk.

There is a wide range in ESR values that are considered normal, but ESR values that are abnormal and thus indicative of inflammation include ESR >15 mm/hr in men under 50 years old, >20 in men over 50 years old and women under 50 years old, and >30 mm/hr in women over 50 years old. The measurement of abnormal ESR (inflammatory marker) levels in a patient indicate that that individual patient is at increased risk for developing an inflammatory disease or a disease associated with inflammation.

Abnormal metabolic markers include total cholesterol (TC) greater than about 160 mg/dL, greater than about 180 mg/dL, greater than about 190 mg/dL, greater than about 200 mg/dL, greater than about 210 mg/dL, greater than about 220 mg/dL, greater than about 230 mg/dL, greater than about 240 mg/dL, greater than about 250 mg/dL, greater than about 260 mg/dL. Abnormal metabolic markers include an LDL cholesterol greater than about 70 mg/dL, greater than about 80 mg/dL, greater than about 90 mg/dL, greater than about 100 mg/dL, greater than about 110 mg/dL, greater than about 120 mg/dL, greater than about 130 mg/dL, greater than about 140 mg/dL, greater than about 150 mg/dL, greater than about 160 mg/dL. Abnormal metabolic marker levels include an HDL cholesterol less than about 60 mg/dL, less than about 50 mg/dL, less than about 40 mg/dL, less than about 30 mg/dL, less than about 20 mg/dL. Abnormal metabolic markers include an elevated LDL particle number or reduced HDL particle number relative to the general population. Abnormal metabolic markers are predictive for increased risk for development of, the pre-clinical period of, early-stages of, or established diseases including hyperlipidemia, atherosclerosis, atherosclerotic disease, NASH, NAFLD, metabolic syndrome, and other inflammatory diseases and diseases associated with inflammation.

Other inflammatory and metabolic markers of patients at risk for metabolic disease associated with inflammation include: lipoprotein a (LPa), with an abnormal metabolic marker level being greater than about 30 mg/dL; Apolipoprotein A1, with an abnormal metabolic marker level being less than about 123 mg/dL; Apolipoprotein B, with an abnormal metabolic marker level being greater than about 100 mg/dL; lipoprotein associated phospholipase A2 (Lp-PLA2), with an abnormal metabolic marker level being greater than about 200 ng/ml; or an urinary albumin/creatinine ratio, with a ratio greater than about 30 mg/g representing an abnormal marker ratio.

MRI, with or without gadolinium or other contrast enhancement, can be used to detect the presence of inflammation and thereby identify individuals with an inflammatory disease or at increased risk of developing an inflammatory disease. For example, MRI-detected inflammation (which represents an abnormal imaging marker result) is defined by the presence of one or more of the following findings: synovitis (synovial lining thickening, proliferation and/or enhancement), a joint effusion, bone marrow edema, and other MRI imaging findings suggestive of inflammation (Krasnokutsky et al, Arthritis Rheum. 2011 63(10):2983-91. doi: 10.1002/art.30471 PMID: 21647860; Roemer et al, Osteoarthritis Cartilage. 2010 October; 18(10):1269-74. PMID: 20691796; Guermazi et al, Ann Rheum Dis. 2011 70(5):805-11, PMID: 21187293). Guermazi et al. (Guermazi et al, Ann Rheum Dis. 2011 70(5):805-11, PMID: 21187293) defines a semiquantiative scoring system for grading the level of inflammation in joints, allowing one to determine (1) whether an individual has inflammation or not, and (2) the degree of inflammation in an individual. Individuals with evidence of joint inflammation according to the Guermazi scoring system can be classified as having increased risk for the development of OA, pre-clinical OA, early-stage OA, or established OA. The degree of inflammation as evaluated by the Guermazi scoring system predicts development and/or progression of the inflammatory disease OA. MRI, with or without gadolinium, can be applied to many other conditions to determine whether or not inflammation (an abnormal imaging marker result) is present, and when present an individual is at increased risk for developing, has pre-clinical, has early-stage inflammatory disease, or has established inflammatory disease or disease associated with inflammation.

Ultrasound-detected inflammation (an abnormal imaging marker) is defined by the presence of one or more of the following findings: synovial lining thickening and/or enhancement, a joint effusion, bone marrow enhancement, a Doppler-flow signal in the synovial lining, and other findings suggestive of inflammation (Guermazi et al, Curr Opin Rheumatol. 2011 23(5):484-91. PMID: 21760511; Hayashi et al, Osteoarthritis Cartilage. 2012 March; 20(3):207-14. PMID: 22266236; Haugen et al, Arthritis Res Ther. 2011; 13(6):248. PMID: 22189142). Individuals with ultrasound-detected inflammation are at increased risk for, in the early stages of, or have established inflammatory disease or disease associated with inflammation.

In various embodiments, this invention relates to the use of DHCQ, or DHCQ in combination with atorvastatin, to treat inflammatory diseases and diseases associated with inflammation. In one embodiment the statin comprises atorvastatin, and in other embodiments the statin can comprise cerivastatin, fluvastatin, lovastatin, mevastain, or pitavastatin. Importantly, this novel use of a combination of DHCQ and a statin does not require use of an antibiotic, an anti-viral, or an anti-bacterial agent. No antibiotic, anti-viral, or anti-bacterial compound is needed for the anti-inflammatory activity and disease-modifying activity described for DHCQ, or the combination of DHCQ and a statin.

In certain in vitro assays, ex vivo assays, and in vivo models, the combination of DHCQ and atorvastatin exhibits unexpected and surprising synergy in reducing the production of inflammatory mediators in in vitro and ex vivo assays, and in reducing disease activity and inflammation in in vivo models. In other in vitro assays, ex vivo assays, and in vivo models, the combination exhibits an unexpected and surprising additive effect in reducing the production of inflammatory mediators in in vitro and ex vivo assays, and reducing disease activity and inflammation in the in vivo model. In general, the DHCQ alone and individual statin alone, did not provide as robust anti-inflammatory or disease-modifying activity as did the combinations (the combination of DHCQ+atorvastatin), which can provide for a synergistic benefit when combined.

Multiple markers of inflammatory disease, and specifically detection of abnormal levels of these markers, can be used to identify individuals at increased risk for disease, with early-stage disease, as well as to monitor response to intervention with DHCQ, or DHCQ and atorvastatin therapy. Such markers, also termed biomarkers, including laboratory test results, imaging results, physical findings, research test markers, and other markers of inflammation and disease. Examples of laboratory markers include: hs-CRP as a measure of systemic inflammation; ESR as a measure of systemic inflammation; hemoglobin A1C as a measure of poor glucose control and thus the severity of diabetes and/or metabolic syndrome; liver enzyme tests as a measure of hepatic dysfunction and of the activity of NAFLD or NASH; and cholesterol and LDL cholesterol as a sign of atherosclerosis. Examples of imaging markers include, evidence of early synovitis on MRI of the hand joints in individuals with pre-clinical or early stage RA; evidence of low-grade synovitis on MRI of a joint in individuals at-risk for OA; evidence of demyelinating lesions on MRI of the brain of an individual at risk for MS. Examples of research biomarkers include: multiplex profiling of cytokines in blood to identify individuals with systemic inflammation, and to determine the specific subset of cytokines causing the individual to be "at-risk" or mediating early-stage disease; analysis of gene expression to subtype the inflammatory disease; analysis of genetic variants through genotyping or sequencing the genome of an individual to determine which inflammatory disease(s) an individual is at increased risk for developing. In other embodiments, such laboratory, imaging and research biomarkers are used to identify individuals at increased risk for developing, or with early-stage, inflammatory disease. In other embodiments, such laboratory, imaging and research biomarkers are using to monitor an individual's response to DHCQ therapy, to determine if therapy need to be continued, or if therapy needs to be increased, or if an individuals' risk has decreased and thus therapy can be discontinued.

EXAMPLES

The following are examples of the methods and compositions of the invention. It is understood that various other embodiments may be practiced, given the general description provided above.

Example 1

Treatment with Desethylhydroxychloroquine (DHCQ) Prevented the Development of and Reduced the Severity of Murine Rheumatoid Arthritis (RA)

DBA/1 mice (n=12-15 per group) were induced to develop collagen-induced arthritis (CIA), a mouse model for RA, by immunization with type II collagen emulsified in complete Freund's adjuvant (CFA) followed 21 days later by boosting with type II collagen emulsified in incomplete Freund's adjuvant (IFA). On the day of the first immunization, a timepoint at which mice exhibited no symptoms of RA but had already been induced for and exhibit an increased inflammatory state (due to the immunization with CFA) and develop autoantibodies by day 14 during this pre- or early-RA disease period, treatment was initiated with hydroxychloroquine (HCQ), desethylhydroxychloroquine (DHCQ), desethylchloroquine (DCQ), or bisdesethylchloroquine (BDCQ), and each molecule was dosed at 50 mg/kg/day by oral gavage (once daily dosing) for 2 weeks starting on the day of the initial immunization, then increased to a loading dose of 100 mg/kg/day by oral gavage starting on day 14 to efficiently achieve therapeutic drug concentrations in the tissues, and then at day 21 the dose was reduced back to and continued at a lower maintenance dose of 50 mg/kg/d by oral gavage. Statistical comparisons of scores for the individual groups demonstrated that treatment with HCQ or DHCQ resulted in statistically reduced development of disease and reduced disease activity as compared to treatment with the vehicle (control) (# $P<0.05$ by the Mann Whitney U test). In contrast, HCQ metabolites desethylchloroquine (DCQ) and bisdesethylchloroquine (BDCQ) were not associated with statistical protection or reduction in disease severity compared as to vehicle treated mice (by the Mann Whitney U test).

8 week old male DBA/1 mice (Jackson Laboratory) were used for generating the murine model of RA. Experiments were performed under protocols approved by the Committee of Animal Research at Stanford University and in accordance with NIH guidelines. DBA/1 mice were intradermally immunized with 100 µg/mouse of bovine collagen type II (Chondrex) emulsified in complete Freund's adjuvant (CFA) containing 250 µg/mouse of heat-killed *Mycobacterium tuberculosis* H37Ra (BD). Twenty-one days after immunization, mice were subcutaneously injected at the base of the tail with 100 µg/mouse of bovine CII emulsified in incomplete Freund's adjuvant (IFA). Prior to approximately day 28, the mice exhibit no symptoms of RA but due to the collagen immunization are in a state of pre- or early-RA with increased levels of inflammation. Further, by day 14 the immunized pre-RA mice have developed autoantibodies against type II collagen, the autoantibody response undergoes epitope spreading, and the mice have a persistently inflamed pre-RA disease state (Arthritis Res Ther. 2008; 10(5):R119; Finnegan et al, Autoimmunity. 2012 45(5):353-63). Mice start to manifest clinical RA at approximately day 28, and inflammatory arthritis in the mice was evaluated by a visually scoring limb inflammation, measuring paw thickness, and weighing spleens. The visual scoring system was as follows: grade 0, no swelling or erythema; grade 1, mild swelling and erythema or digit inflammation; grade 2, moderate swelling and erythema confined to the region distal to the mid-paw; grade 3, more pronounced swelling and erythema extending to the ankle; grade 4, severe swelling, erythema, and joint rigidity of the ankle, foot, and digits. Each limb was graded with a score of 0-4, with a maximum possible score of 16 for each individual mouse. Paw thickness was determined by measuring the thickness of both hind paws with 0- to 10-mm calipers and calculating the mean of the two measurements.

Figure 2:
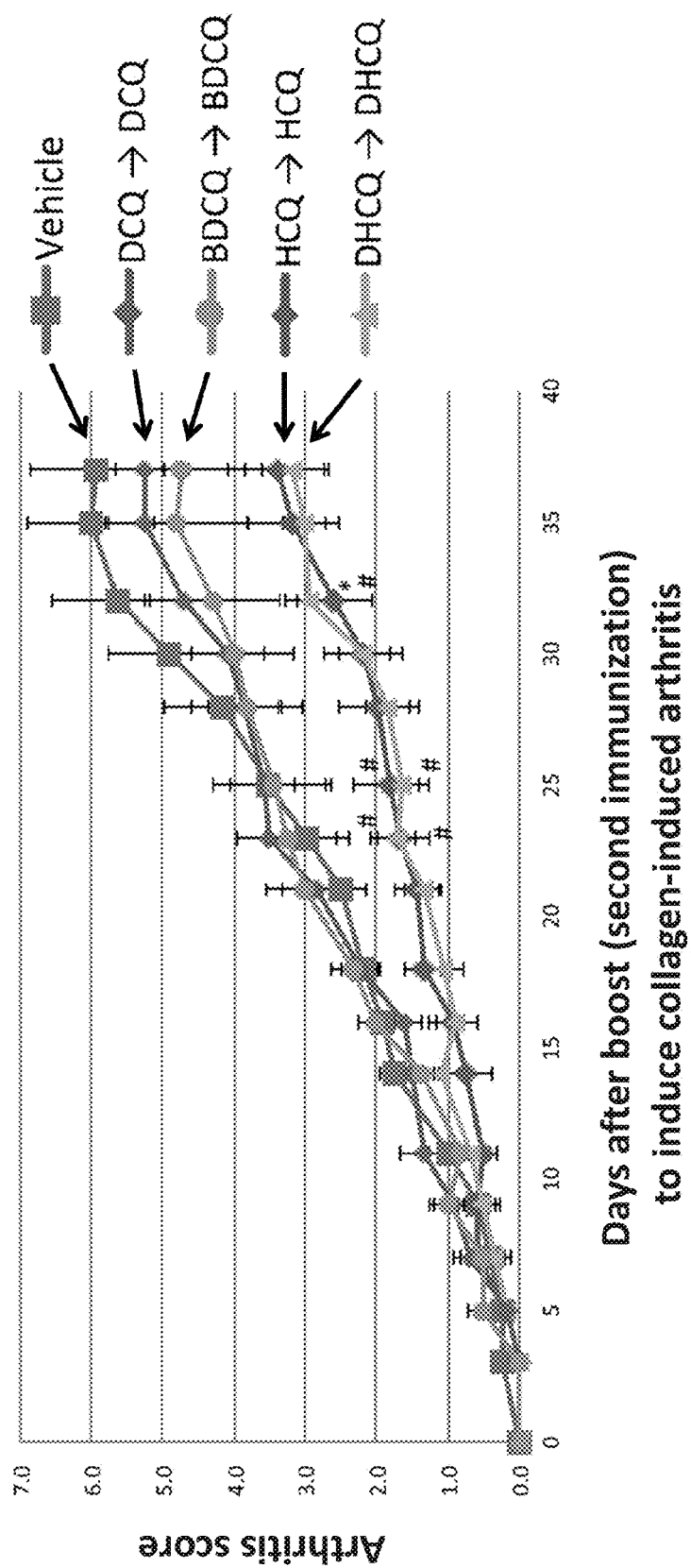
FIG. 2 is a plot of "arthritis scores" versus "days after boost" (second immunization to induce arthritis) in a mouse model for rheumatoid arthritis, comparing prevention of disease with vehicle (control), HCQ, DHCQ, DCQ, and BDCQ.

On the day of the first immunization, treatment was initiated with hydroxychloroquine (HCQ), desethylhydroxychloroquine (DHCQ), desethylchloroquine (DCQ), or bisdesethylchloroquine (BDCQ), 50 mg/kg/day delivered by oral gavage in 100 µL once per day for 2 weeks, then increased to a loading dose level of 100 mg/kg/day by oral gavage for one week to more efficiently achieve therapeutic aminoquinoline levels in the tissues, then starting at the time of boosting (day 21) the dose was reduced to the maintenance dose of 50 mg/kg/day of HCQ, DHCQ, DCQ or BDCQ by oral gavage. The purpose of the loading dose was to expedite getting tissue levels of the dosed aminoquinolines up to therapeutic levels following the initiation of therapy. Mice in the control group were treated with vehicle alone. Mice were scored for the severity of arthritis using the visual scoring system (termed "arthritis score"), and developed arthritis approximately one-week following boosting (28 days following initial immunization). The arthritis severity of the HCQ and DHCQ treated groups were statistically lower than the severity of arthritis in mice treated with vehicle, bisdesethylchloroquine (BDCQ), or desethylchloroquine (DCQ), $P<0.05$ by Mann Whitney U test. FIG. 2 demonstrates that mice induced for CIA and treated with HCQ or DHCQ exhibited reduced arthritis as measured by total arthritis score as compared to mice treated with BDCQ or vehicle ($P<0.05$ by Mann Whitney U test).

Example 2

Desethylhydroxychloroquine (DHCQ) Prevented the Development of and Reduced the Severity of the Experimental Autoimmune Encephalomyelitis Mouse Model for Multiple Sclerosis (MS)

Figure 3:
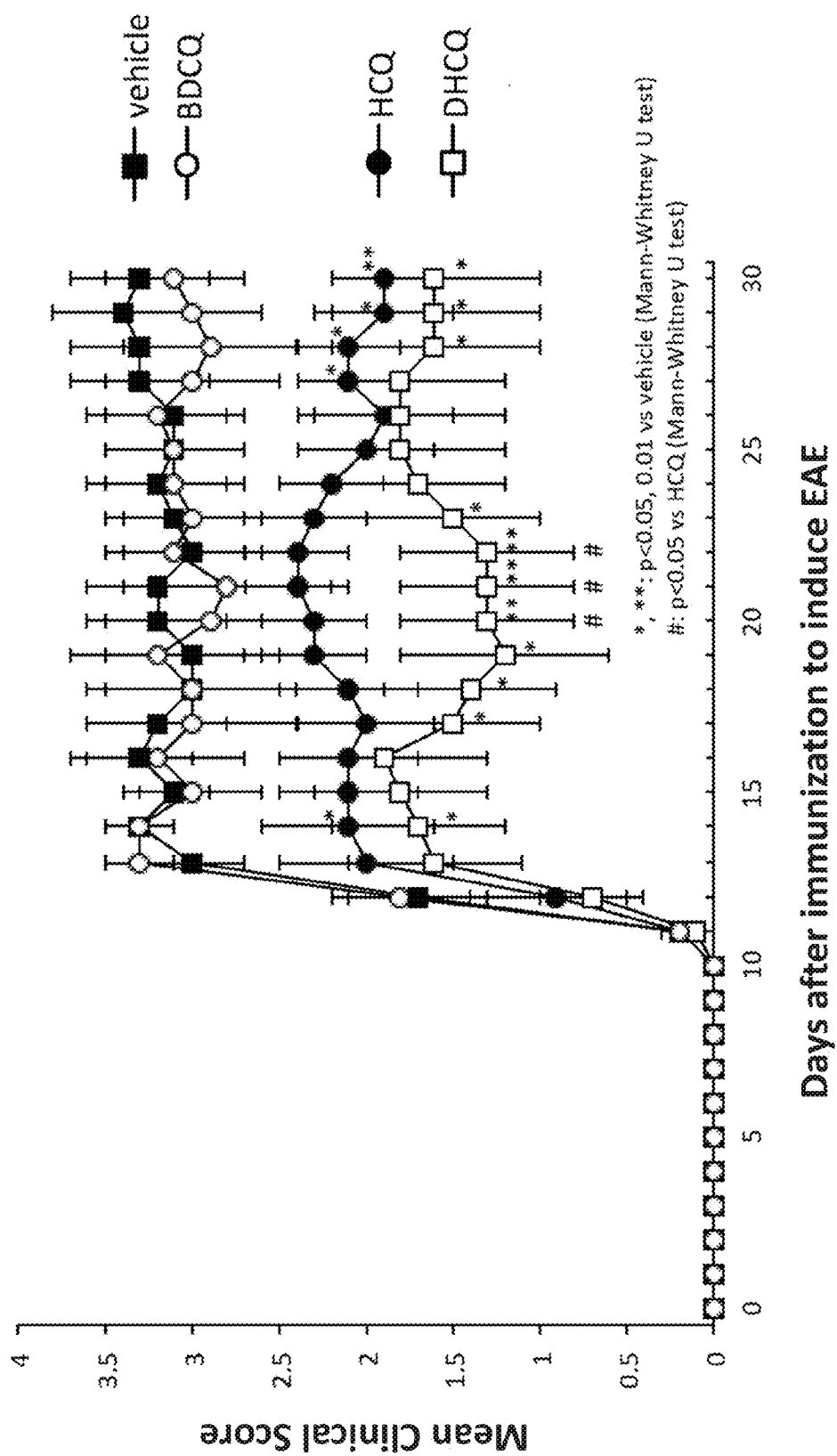
FIG. 3 is a plot of "mean clinical scores" versus "time after immunization", comparing vehicle, HCQ, BDCQ, and DHCQ for preventing development of mouse multiple sclerosis.
Figure 4:
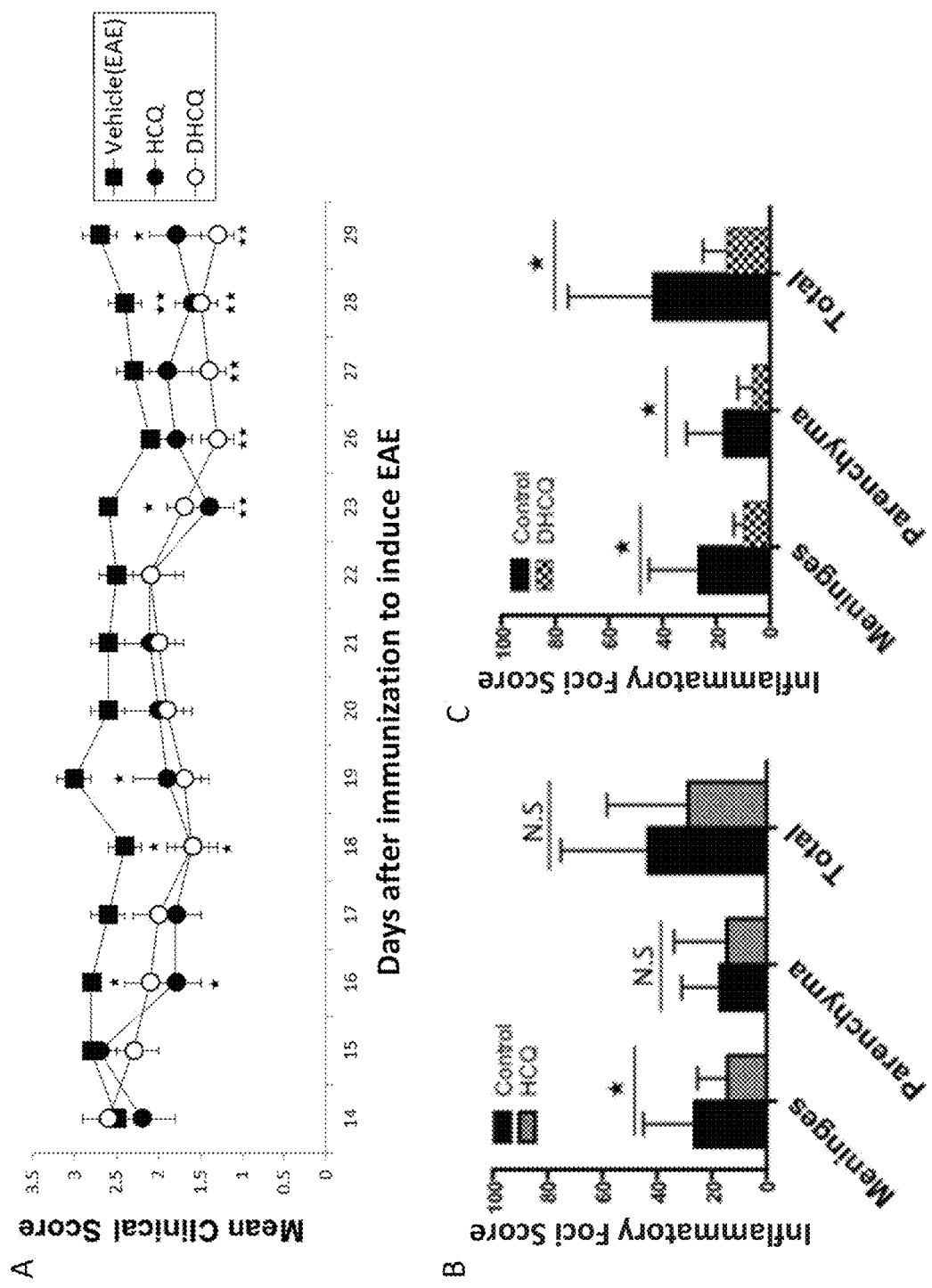
FIG. 4 is a plot of "mean clinical scores" versus "time after immunization", comparing vehicle, HCQ, and DHCQ treatment of established mouse multiple sclerosis.

Experimental autoimmune encephalomyelitis (EAE), a mouse model for MS, was induced in SJL mice (n=10 per group) by immunization with proteolipid protein peptide 139-151 (PLP 139-151) in CFA. Starting at the time of immunization mice were treated with a loading dose of DHCQ or HCQ 100 mg/kg/day by oral gavage to expedite achieving therapeutic tissue levels of the dosed aminoquinoline following the initiation of therapy, and on day 8 the dose was reduced to a maintenance dose of 50 mg/kg/day. For the first approximately 10 days following the initial immunization, the mice exhibit no symptoms of MS but are inflamed, develop autoantibodies, and are in a pre- or early-MS disease state. Starting on day 8, mice were scored daily for the severity of EAE. Mann Whitney U test comparisons between the groups demonstrated that treatment with DHCQ and HCQ both prevented development of and reduced the severity of EAE compared to treatment with vehicle control or bisdesethylchloroquine (BDCQ) (FIG. 3). Thus, we demonstrated that desethylhydroxychloroquine prevented development of and reduced the severity of the EAE mouse model of MS (*$P<0.05$ by Mann Whitney U test), and that the reduction inflammation was correlated with the reduction in disease severity. DHCQ demonstrated statistically superior activity, lowering EAE disease activity to a greater extent, as compared to HCQ treatment, at several timepoints (# $P<0.05$ by Mann Whitney U test).

Example 3

Desethylhydroxychloroquine (DHCQ) Treated Established Mouse Multiple Sclerosis (MS)

Experimental autoimmune encephalomyelitis (EAE), a mouse model for MS, was induced in SJL mice (n=10 per group) by immunization with proteolipid protein peptide 139-151 (PLP 139-151) in CFA. On day 14, when mice exhibited an average clinical score of approximately 2.5, treatment was initiated with DHCQ 100 mg/kg/day or HCQ 100 mg/kg/day by oral gavage, and 8 days later the dose was reduced to 50 mg/kg/day. Mann Whitney U test comparisons between the groups demonstrated that treatment with DHCQ and HCQ both treated established EAE by reducing the severity of EAE compared to treatment with vehicle control (*$P<0.05$; ** $P<0.01$ by Mann Whitney U test) (FIG. 4A). At the termination of the experiment, mice were sacrificed, and the brains harvested, fixed, sections histologically scored by a blinded examiner for the number of inflammatory foci in the meninges and parenchyma using an established "Inflammatory Foci Score" (Chang et al, Recovery from EAE is associated with decreased survival of encephalitogenic T cells in the CNS of B7-1/B7-2-deficient mice. European J. Immunology, 2003, 33(7):2022-32). As compared to the vehicle control treatment, treatment with HCQ reduced the Inflammatory Foci Score in the meninges (* $P<0.05$ by two-tailed T test) and exhibited trends towards reductions in the parenchyma and total scores (FIG. 4B), while treatment with DHCQ statistically reduced the Inflammatory Foci Score in the meninges, parenchyma as well as the total score (* $P<0.05$ by two-tailed T test) (FIG. 4C). Thus, DHCQ potently treated established multiple sclerosis in the EAE mouse model, and exhibited more robust therapeutic activity than treatment with HCQ.

Example 4

Figure 5:
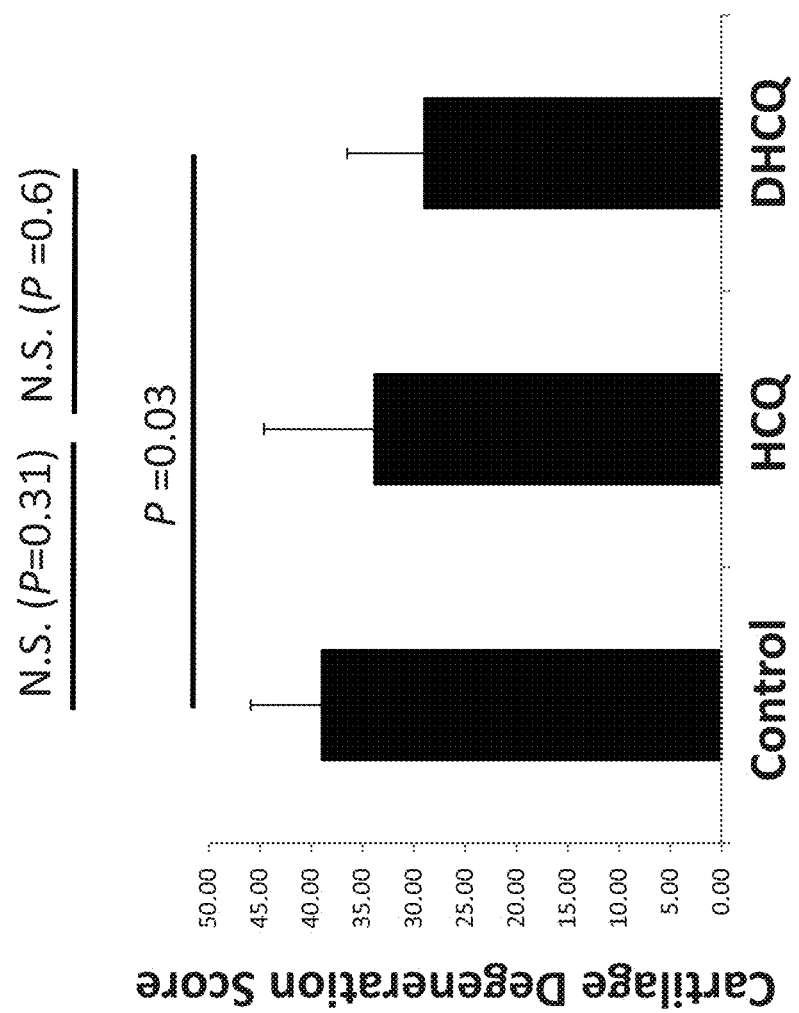
FIG. 5 is a chart of cartilage degeneration scores, comparing vehicle, HCQ and DHCQ treatment of mouse osteoarthritis.
Figure 7:
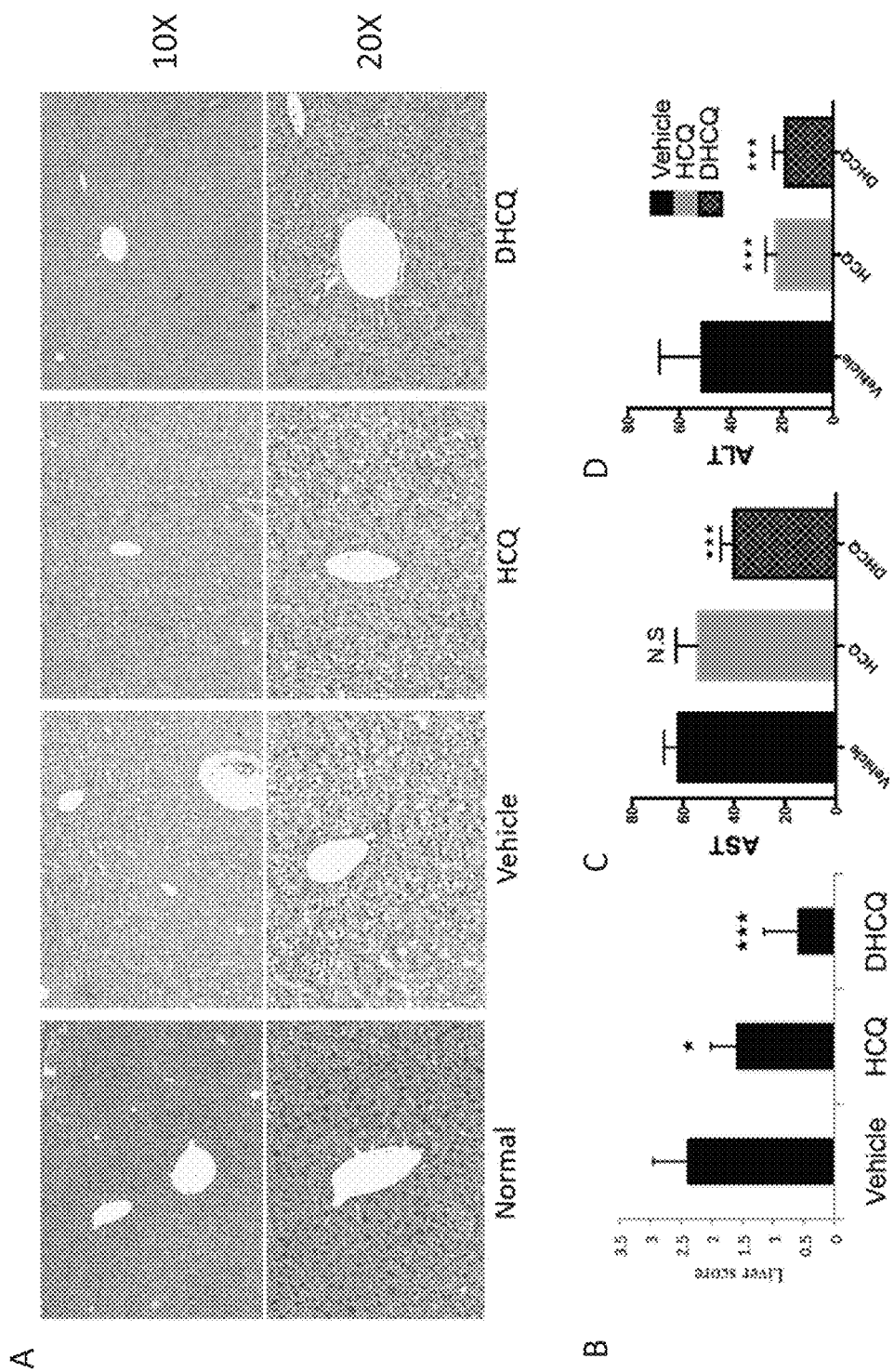
FIG. 7 shows micrographs of liver tissue and charts of liver scores, AST levels and ALT levels, comparing vehicle, HCQ, and DHCQ for prevention of the development of non-alcoholic steatohepatitis (NASH) in mice with diet-induced obesity.
Figure 8:
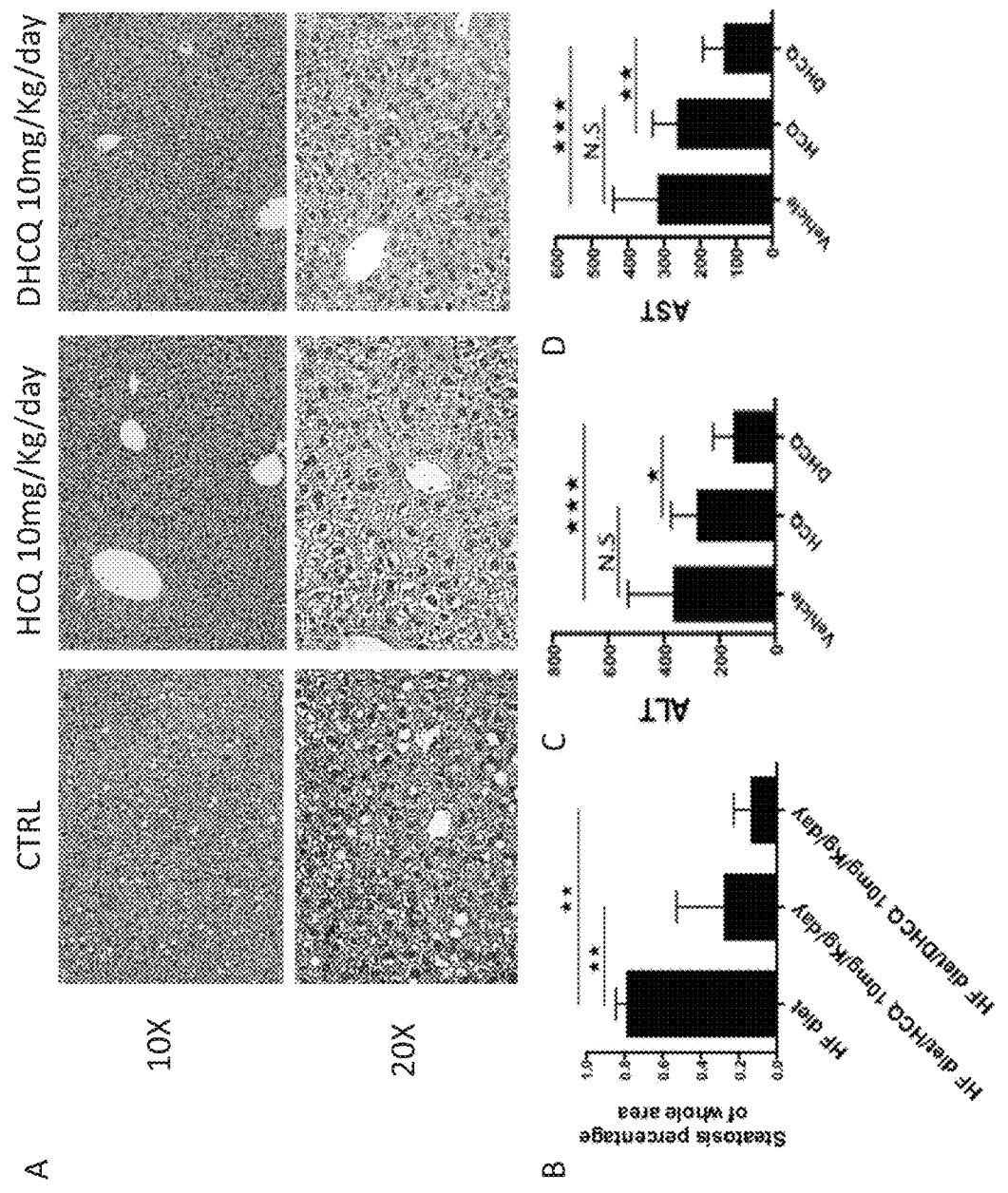
FIG. 8 shows micrographs of liver tissue and charts of liver scores, AST levels and ALT levels, comparing vehicle, HCQ, and DHCQ treatment of established non-alcoholic steatohepatitis (NASH) in mouse diet-induced obesity.

Desethylhydroxychloroquine (DHCQ) Prevented the Development of and Reduced the Severity of Osteoarthritis (OA) in a Mouse Model This example demonstrates that in mice surgically induced by destabilization of the medial meniscus (DMM) to develop OA, treatment with desethylhydroxychloroquine statistically prevented and reduced the severity of OA ($P=0.03$ by two-tailed T test) (FIGS. 5 and 6). C57BL6 (B6) mice (n=6-10 per group) were surgically induced to develop OA by destabilization of the medial meniscus (DMM). One week following surgical induction, treatment was initiated with vehicle control, hydroxychloroquine (HCQ), or desethylhydroxychloroquine (DHCQ) dosed at 100 mg/kg/day by oral gavage (once per day). After 3 months, mice were sacrificed, joints harvested, joint sections cut, and tissue sections stained with safranin-O. An examiner blinded to treatment used microscopy to score the severity of OA. The "Cartilage Degeneration Score" (also known as the "OA score", "Severity Score" and "Histology Score") was determined by a blinded examiner, and the two-tailed T test used to determine if there were statistical differences in the Cartilage Degeneration Scores between groups. DHCQ statistically prevented and reduced the severity of OA as assessed by the cartilage degeneration score by two-tailed T test compared to treatment with the vehicle control (P=0.03) (FIG. 5). Hydroxychloroquine did not result in a statistically signification prevention or reduction in OA severity, based on the cartilage degeneration score (FIG. 5).

The histologic sections generated at the termination of the mouse OA experiment presented above and in FIG. 5 were subject to blinded scoring for the "Osteophyte Score" (measure of the amount of osteophyte or ectopic bone formation) and "Synovitis Score" (measure of the amount of synovial and joint inflammation). The scores between groups were compared by two-tailed T test. As compared to the vehicle-treated control, DHCQ statistically prevented and reduced the severity of cartilage degeneration, and also statistically prevented and reduced the development of osteophytes (P<0.01) and synovitis (P<0.01) (FIG. 6).

C57/BL6 (B6) mice (n=7-10 per group) were surgically induced to develop OA by destabilization of the medial meniscus (DMM). Experiments were performed under protocols approved by the Stanford University Committee of Animal Research and in accordance with NIH guidelines. Murine OA was generated by surgically by destabilization of the DMM (Glasson, S., S., et al., Osteoarthritis Cartilage, 15: 1061-1069 (2007)). One week following surgical induction of the DMM model, the mice walk and run normally, the articular cartilage is intact and there is no evidence of OA, but due to the surgical procedure the mice are in a pre- or early-OA disease state and develop OA over the following months.

Mice were euthanized 3 months after surgery. Their stifle joints were decalcified in EDTA solution, fixed in 4% paraformaldehyde, and embedded in paraffin. Serial 4 micron sections were cut and stained with toluidine blue. Scoring of arthritis in these histology sections was done according to a modified version of previously described composite scoring systems (Kamekura, S., et al. Osteoarthritis Cartilage 13: 632-641 (2005); Bendele, A. M., J Musculoskelet Neuronal Interact., 1: 363-376 (2001)). The "OA Score" was calculated as follows: cartilage degeneration (0-4) was multiplied by the width (1=1/3, 2=2/3, and 3=3/3 of surface area) of each third of the femoral-medial and tibial-medial condyles, and the scores for the 6 regions were summed. To evaluate osteophyte (ectopic bone) formation, we scored toluidine-blue-stained sections according to a previously described scoring system (Kamekura, S., et al. Osteoarthritis development in novel experimental mouse models induced by knee joint instability. Osteoarthritis Cartilage 13, 632-641 (2005)): 0, none; 1, formation of cartilage-like tissues; 2, increase of cartilaginous matrix; 3, endochondral ossification. To evaluate synovitis, we scored H&E-stained sections according to a previously described scoring system (Blom, A. B., et al. Synovial lining macrophages mediate osteophyte formation during experimental osteoarthritis. Osteoarthritis Cartilage 12, 627-635 (2004)): 0, no changes compared to normal joints; 1, thickening of the synovial lining and some influx of inflammatory cells; 2, thickening of the synovial lining and intermediate influx of inflammatory cells; and 3, profound thickening of the synovial lining (more than four cell layers) and maximal observed influx of inflammatory cells. Scores for osteophyte formation and synovitis were recorded for the femoral-medial and the tibial-medial condyles on the operated side of the joint, and the scores for the two regions were summed and statistical comparisons performed using a two-tailed T test.

Treatment was started 1 week after surgical induction of destabilization of the medial meniscus (DMM), a time point at which mice were at increased risk for the development of OA. DMM in mice is similar to a degenerative or traumatic meniscal tear in humans, which has been demonstrated to increase the risk of humans for development of OA by 5-fold. One week following induction of DMM, mice walk and run normally, are at increased risk for the development of OA but do not exhibit classic histologic features of OA—specifically, at this time point there is no evidence of overt cartilage loss or bone remodeling (osteophyte formation, subchondral bone remodeling). Nevertheless, 1 week following DMM there is likely cartilage edema, proteoglycan loss, and other early features characteristic of both murine and human OA.

Example 5

Desethylhydroxychloroquine (DHCQ) Prevented Development of High Fat Diet-Induced Non-Alcoholic Steatohepatitis (NASH)

To evaluate the effect of DHCQ and HCQ on an animal model of non-alcoholic fatty liver disease (NAFLD) which can lead to the development of NASH, C57BL/6 mice (8 per group) were fed a high-fat "western-style" diet (60% caloric content from fat; Taconic) for 6 weeks. The mice were asymptomatic throughout this time, but were developing a pre- or early-disease state. The mice were treated, starting at the time of initiation of the high-fat diet, with HCQ (100 mg/kg/day), DHCQ (100 mg/kg/day), or vehicle control, to prevent the development of NAFLD and NASH. After 6 weeks of treatment with DHCQ, HCQ and vehicle (control) while on a high-fat diet, blood was collected and mice sacrificed for histological analysis of liver pathology. Livers from the mice in each treatment group were fixed, embedded, sectioned, stained with H&E, representative micrographs are presented in FIG. 7A (both 10× and 20× magnification), "liver scores" determined using an established scoring system for NASH (Brunt et al, Nonalcoholic steatohepatitis: a proposal for grading and staging the histological lesions, American J. Gastroenterology, 1999, 94(9): 2467-74). As demonstrated in FIG. 7B, the "liver score" was statistically reduced in both DHCQ treated (P<0.001) and HCQ treated (P<0.05) as compared to vehicle control treated mice (by two-tailed T test). As a serum laboratory marker of NASH, serum levels of alanine aminotransferase (ALT; also known as serum glutamic pyruvate transaminase [SGPT]) and serum aspartate transaminase (AST; also known as serum glutamic oxaloacetic transaminase [SGOT]) were measured, and it was demonstrated that DHCQ prevents and reduces abnormal elevations in the levels of these liver transaminases as compared to treatment with the vehicle control (two-tailed T test; * P<0.05; *** P<0.001) (FIG. 7C,D). These studies demonstrate that treatment with DHCQ prevented the development of, and reduced the severity of, NAFLD and NASH. Further, DHCQ exhibited statistically superior activity to HCQ in reducing the liver score, AST and ALT (P<0.05 by two-tailed T test, not indicated on graph in FIG. 7C-D).

Example 6

Desethylhydroxychloroquine (DHCQ) Treated Established High Fat Diet-Induced Non-Alcoholic Steatohepatitis (NASH)

To evaluate the effect of DHCQ and HCQ on established NASH, C57BL/6 mice (8 per group) were fed a high-fat "western-style" diet (60% caloric content from fat; Taconic). Following initiation of the high-fat diet, after 2 weeks blood was drawn and analyzed for abnormal elevations in serum markers for NASH including AST and ALT. The AST and ALT became abnormally elevated following the initial 2 weeks of high-fat diet, and at that time treatment was initiated with HCQ (10 mg/kg/day), DHCQ (10 mg/kg/day), or vehicle control. After 6 weeks of treatment, mice were fasted and blood was collected for serum analysis and mice sacrificed for histologic analysis of liver pathology. FIG. 8A presents micrographs of representative liver tissue sections at both 10× and 20× magnification. The liver sections were scored for "steatosis percentage of whole area" using a refined and adapted version of a previously described scoring system (Tous et al., Feeding apolipoprotein E-knockout mice with cholesterol and fat enriched diets may be a model of non-alcoholic steatohepatitis. Mol cell Biochemistry, 2005, 268:53-59; Tous et al, Dietary cholesterol and differential monocyte chemoattractant protein-1 gene expression in aorta and liver of apo E-deficient mice. Biochemical and Biophysical Research Communications, 2006, 340:1078-1084), and treatment with either DHCQ or HCQ statistically reduced the steatosis percentage as assess by liver histology (* $P<0.05$, *** $P<0.01$ by 2-tailed T test) (FIG. 8B). AST and ALT levels in the collected serum were measured and 2-tailed T Tests used to compare levels between groups. Treatment with DHCQ statistically reduced abnormal elevations in AST and ALT as compared to vehicle control ($P<0.001$; FIG. 8C,D), while treatment with HCQ only exhibited a trend towards reduction in abnormal elevations in AST and ALT (N.S.=non-significant). DHCQ treatment exhibited statistical reductions in the AST and ALT as compared to treatment with HCQ (* $P<0.05$, ** $P<0.01$ by two-tailed T test). These studies demonstrate that DHCQ exhibited robust efficacy in treating established NASH.

Example 7

Figure 9:
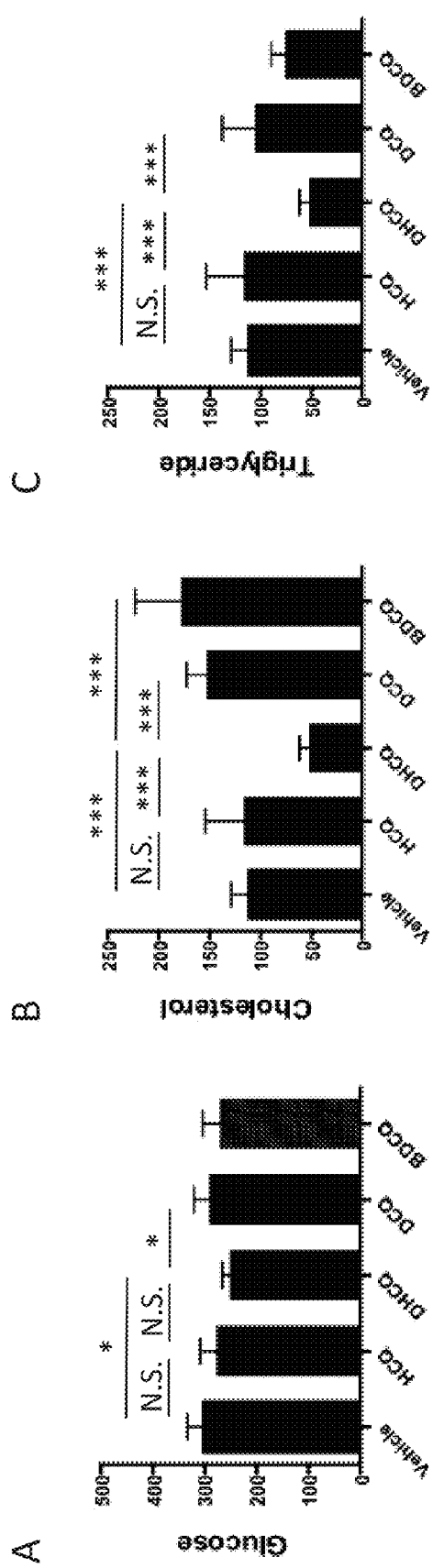
FIG. 9 shows graphs of glucose, triglyceride, and cholesterol levels, comparing vehicle, HCQ, DHCQ, BDCQ, and DCQ treatment of type II diabetes, hyperlipidemia and metabolic syndrome in mouse diet-induced obesity.

DHCQ Treated Type II Diabetes, Hyperlipidemia and Metabolic Syndrome in Mouse Diet-Induced Obesity To evaluate treatment with DHCQ and HCQ on a mouse model of diet-induced type II diabetes, hyperlipidemia and metabolic syndrome, C57BL/6 mice (8 per group) were fed a high-fat "western-style" diet (60% caloric content from fat; Taconic). In an analogous fashion to that in Example 6, two weeks following initiation of the high-fat diet groups of mice were initiated on treatment with vehicle control, HCQ (10 mg/kg/day) or the HCQ metabolites DHCQ (10 mg/kg/day), DCQ (10 mg/kg/day), or BDCQ (10 mg/kg/day). After 6 weeks of treatment, blood was collected for analysis of glucose, triglyceride, and cholesterol levels. FIG. 9 shows graphs comparing glucose, triglyceride, and cholesterol levels for HCQ, DHCQ, DCQ, and BDCQ treatment of type II diabetes, hyperlipidemia and metabolic syndrome in mouse diet-induced obesity. Levels of glucose represent a biomarker of early insulin resistance and early-onset of type II diabetes, and treatment with DHCQ resulted in statistical reduction in blood glucose levels as compared to treatment with vehicle control (* $P<0.05$, two-tailed T test) (FIG. 9A), while in contrast HCQ, DCQ and BDCQ did not result in statistical reductions in blood glucose as compared to the vehicle control (FIG. 9A). The levels of lipids were also measured in the collected sera, and based on statistical analysis by two-tailed T test DHCQ treatment resulted in statistical reductions in total cholesterol (* $P<0.001$; FIG. 9B) and triglycerides (* $P<0.001$; FIG. 9C), as compared to treatment with the vehicle control. Treatment with HCQ, DCQ and BDCQ did not result in statistical reductions in glucose, cholesterol or triglycerides, as compared to the levels in vehicle control treated mice (N.S.=non-significant by two-tailed T test) (FIG. 9). Further, DHCQ treatment resulted in statistically significant reductions in cholesterol and triglycerides as compared to treatment with HCQ (*** $P<0.001$ by two-tailed T test). DHCQ treatment also resulted in statistically significant reductions in glucose, cholesterol and triglycerides as compared to treatment with DCQ (* $P<0.05$, * $P<0.001$ by two-tailed T test), and a statistically significant reduction in cholesterol as compared to treatment with BDCQ (* $P<0.001$ by two-tailed T test). These data demonstrate that DHCQ treated diet-induced obesity associated development of insulin resistance, type II diabetes, hyperlipidemia, and metabolic syndrome, and did so statistically more effectively than HCQ, DCQ and BDCQ.

Example 8

Figure 10:
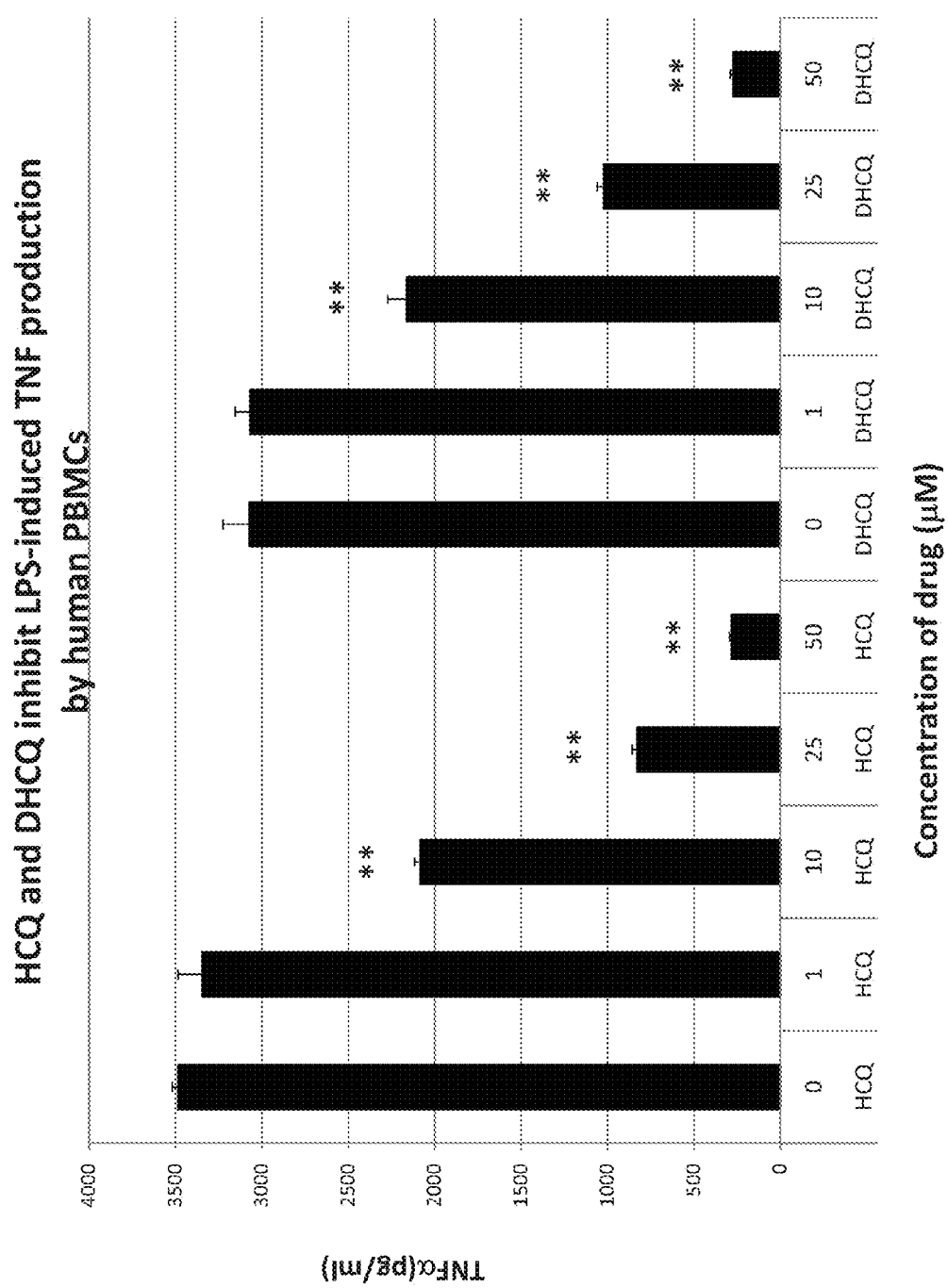
FIG. 10 is a chart of TNFα levels, comparing treatment of human peripheral blood mononuclear cells (PBMCs) stimulated with lipopolysaccharide (LPS) with varying amounts of HCQ or DHCQ.

Desethylhydroxychloroquine (DHCQ) Reduced Inflammatory Cytokine Production in Response to a Proinflammatory Stimulus DHCQ reduced the production of the pro-inflammatory cytokine tumor necrosis factor (TNF) by human peripheral blood mononuclear cells (PBMCs) in response to pro-inflammatory lipopolysaccharide (LPS) stimulation (FIG. 10). Human PBMCs were isolated using Ficoll, 200,000 PBMCs were added to each well of a 96-well plate, and stimulated with LPS 10 µg/ml in the presence of a range of concentrations from 0 to 50 µM DHCQ, or 0 to 50 µM HCQ, for 14 hours, following which culture supernatants were collected and TNF measured by ELISA. Assays were run in triplicate. Mean TNF levels with standard error of the mean are displayed. The Tukey test was used to statistically compare results between groups, and both HCQ and DHCQ reduced PMBC TNF production at 10, 25 and 50 µM concentrations as compared to LPS stimulation in the absence of these molecules (** $P<0.001$, by two-tailed T test).

Isolation of human PBMCs and monocytes. The Ficoll-Paque™ Plus (Cat; 17-1440-03GE Healthcare) was used to isolate human peripheral blood mononuclear cells (PBMCs) from blood collected from healthy donors. For cell culture, the isolated PBMCs were resuspended in culture medium (RPMI1640) containing 10% FCS and antibiotics (penicillin 100 IU/mL and streptomycin 100 µg/mL). Monocyte Isolation Kit II (Cat; 130-091-153, Miltenyi Biotec) was used to isolate monocytes from the suspension of human PBMCs.

Stimulation assays. Human PBMCs plated at 1.0×106 cells/well in 48-well culture plates were pretreated with HCQ or desethylhydroxychloroquine or vehicle for 60 min at 37° C., 5% $CO_2$. Ten micrograms per ml of lipopolysaccharide (LPS; Sigma) 20 h, at 37° C., 5% $CO_2$. Human monocytes plated at 5.0×104 cells/well in 96-well culture plates were pretreated with HCQ or desethylhydroxychloroquine or vehicle for 60 min at 37° C., 5% CO2 and then stimulated with LPS (Sigma) for 15 h at 37° C., 5% $CO_2$.

Readout. Output from the PMBC cellular assay was TNF for the LPS stimulation assays. For each assay, a parallel well treated identically was prepared and level of LDH measured to assure no evidence of cell death was induced by drug treatment.

Example 9

Desethylhydroxychloroquine (DHCQ) Treatment is Less Cytotoxic to Retinal Cells, as Compared to Treatment with Hydroxychloroquine (HCQ) or Bisdesethyhydroxychloroquine (BDCQ) which Both Resulted in Increased Retinal Cell Death The major serious risk to long term administration of hydroxychloroquine is retinal accumulation and subsequent ocular toxicity (Terahi et al, 2008. Semin Opthal. (3):201-208. PMID). The ocular deposition of HCQ, DHCQ, and BDCQ was evaluated by direct retinal cellular toxicity by incubating equivalent concentrations of these molecules with the retinal pigmented epithelial cell line ARPE-19. ARPE-19 is a human retinal pigment epithelial cell line with differentiated properties (Dunn et al., Exp Eye Res. 1996 62(2):155-69). ARPE-19 cells were grown to 90% confluence, and then exposed to 10 g/ml of HCQ, DHCQ, BDCQ, or vehicle control for 24 hours, following which microscopic analysis and photomicroscopy was performed at 40× power. FIG. 11 presents representative photomicrographs demonstrating that DHCQ treatment was associated with less ARPE-19 cellular toxicity as compared to treatment with HCQ or BDCQ which resulted in increased cytotoxicity and death. Retinal epithelial cell viability was high in both the vehicle control and DHCQ treated cells. Retinal cell dysmorphophic features and retinal cell death were observed in the HCQ and BDCQ treated cells (red arrows). Thus, DHCQ exhibited less retinal cell cytotoxicity as compared to the increased retinal cell cytoxicity observed with HCQ or BDCQ treatment.

In FIG. 12, this cytotoxicity is quantitated based on lactate dehydrogenase (LDH) release. As described above, ARPE-19 cells were grown to 90% confluence then exposed to 10 μg/ml HCQ, DHCQ, BDCQ, or vehicle control for 24 hours followed by quantitation of cell death by lactate dehydrogenase (LDH) release assay (Abcam). FIG. 12 demonstrates that treatment with DHCQ did not cause cellular cytotoxicity and death as compared to treatment with vehicle control (P=N.S. (non-significant), by two-tailed T test). In contrast, both BDCQ and HCQ resulted in statistically increased LDH release and thus cellular cytotoxicity of the retinal epithelial cell line as compared to vehicle control (*** P<0.01 by two-tailed T test). Further, equimolar concentrations of HCQ and BDCQ resulted in significantly increased retinal cell toxicity as compared to DHCQ (### P<0.001 by two-tailed T-test) (FIG. 12). These data demonstrate that DHCQ exhibits minimal retinal cell toxicity in vitro, which is in contrast to HCQ and the other HCQ metabolite BDCQ which both exhibited significantly increased retinal cell toxicity.

Example 10

Figure 13:
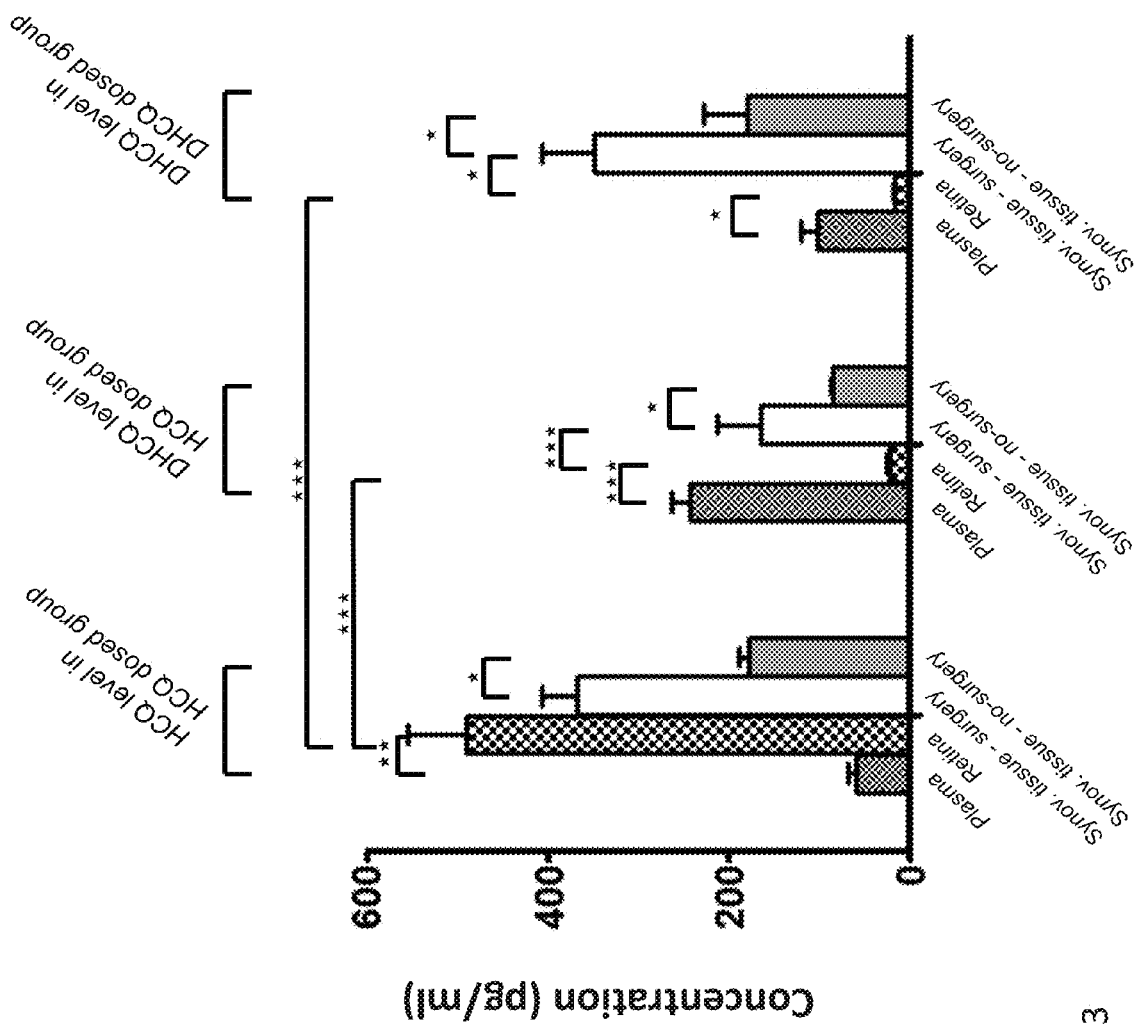
FIG. 13 is a chart comparing HCQ and DHCQ accumulation in plasma, retina tissue, operated joint synovium, and non-operated joint synovium derived from mice treated with either HCQ or DCHQ.

Demonstration that DHCQ Accumulates at Increased Levels in the Plasma and Synovial Tissue, Relative to the Low Levels that Accumulate in the Retina; while in Contrast HCQ Accumulates at High Levels in the Retina Relative to its Levels in Plasma or Synovial Tissue The major risk to long term administration of hydroxychloroquine is retinal accumulation and subsequent ocular toxicity (Terahi et al, 2008. Semin Opthal. (3):201-208. PMID). We sought to evaluate the retinal deposition of HCQ and DHCQ. To do so, we performed mass spectrometric analysis of drug and metabolite content in retina, in operated side and non-operated side synovial tissue, and in plasma derived from mice treated with either HCQ or DHCQ. FIG. 13 presents the measured concentrations of HCQ levels in the indicated tissues (plasma, retina, synovial tissue from surgical side, synovial tissue from unoperated side) from HCQ-dosed mice; DHCQ level in the indicated tissues from HCQ-dosed mice; and DHCQ levels in the indicated tissues from DHCQ-dosed mice. The indicated statistical comparisons between the levels measured in the indicated tissue from each group were compared by two-tailed T test (*P<0.05, P<0.01, *P<0.001). Comparisons of the ratios of the concentrations of HCQ and DHCQ measured in the indicated tissues in the groups of HCQ or DHCQ dosed mice are presented in FIGS. 14-16.

DHCQ accumulated at high levels in the plasma and synovial tissue, with only low-level accumulation in the retina; which is in contrast to HCQ which accumulated a high levels in the retina relative to the lower levels in plasma or synovial tissue (* P<0.05, *** P<0.01, by two-tailed T test) (FIG. 13). Demonstrated are increased levels of HCQ in the retina in HCQ treated mice, but only low-level accumulation of DHCQ in the retinas of HCQ mice or in mice treated with DHCQ (* P<0.05, *** P<0.01, by two-tailed T test) (FIG. 13). Thus, in contrast to HCQ, DHCQ exhibits reduced retinal accumulation in both HCQ and DHCQ treated mice.

Figure 14:
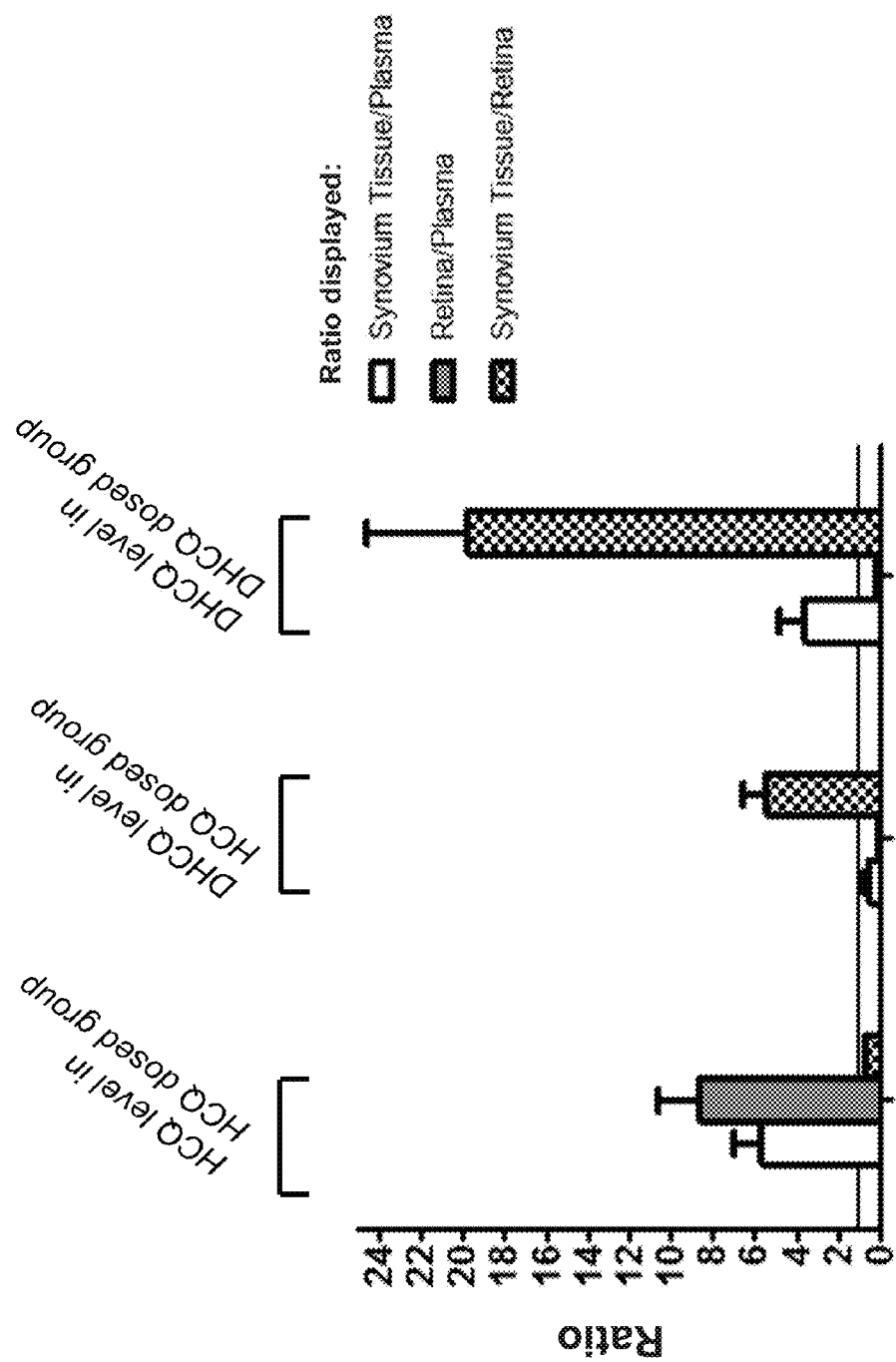
FIG. 14 is a chart comparing the ratio of HCQ and DHCQ levels in various tissues derived from mice treated with either HCQ or DHCQ.
Figure 15:
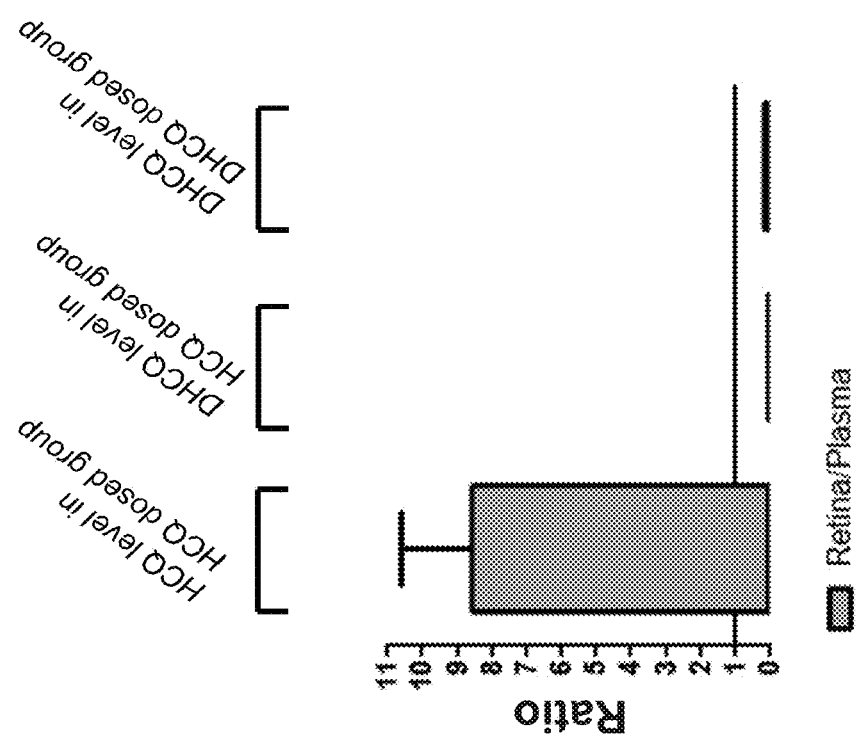
FIG. 15 is a chart comparing the ratio of HCQ and DHCQ levels in the retina tissue and plasma derived from mice treated with either HCQ or DHCQ.
Figure 16:
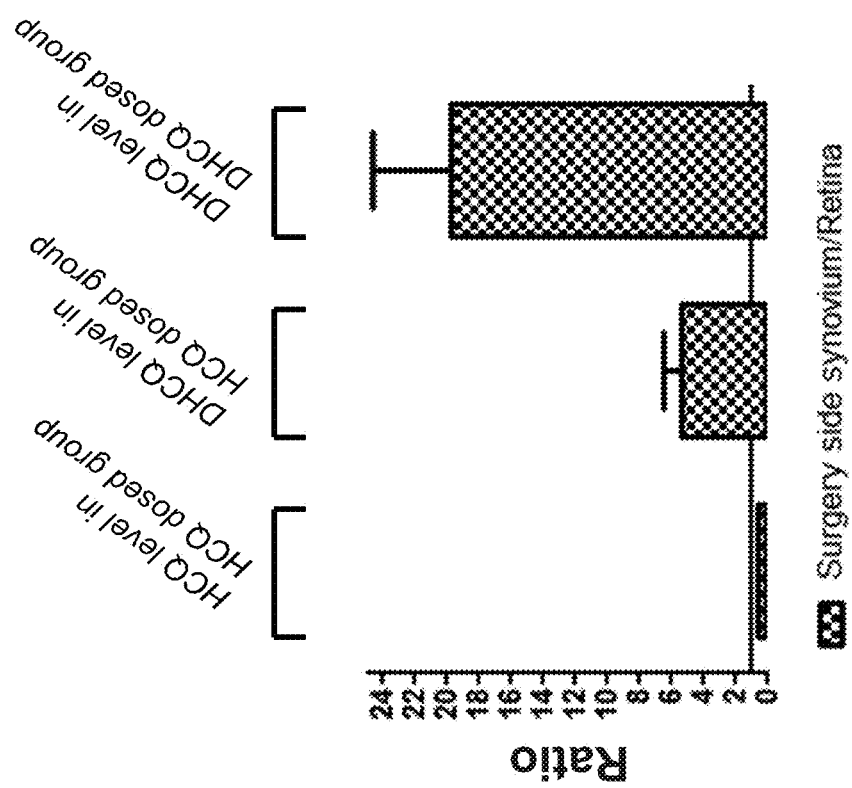
FIG. 16 is a chart comparing the ratio of HCQ and DHCQ levels in the operated joint synovium and retina tissue derived from mice treated with either HCQ or DHCQ.

This is further demonstrated by comparison of the ratios of levels of DHCQ or HCQ in various dosing groups and tissues (FIGS. 14-16). Specifically, the concentrations of DHCQ and HCQ measured in the HCQ and DHCQ dosing groups in FIG. 13 are displayed as one of the 3 following ratios: (1) level in synovial tissue of operated stifle joint [knee]/level in plasma; (2) level in retina/level in plasma; (3) level in synovial tissue of operated stifle joint [knee]/level in retina (FIGS. 14-16).

DHCQ levels were lower in the retina relative to the plasma, while in contrast HCQ accumulated at higher levels in the retina relative to the plasma (FIGS. 14 and 15). FIG. 15 presents the ratio of the level in retina/level in plasma of DHCQ in DHCQ or HCQ dosed mice, and the ratio of the level in retina/level in plasma of DHCQ in DHCQ dosed mice. These data show that HCQ achieves approximately 8.5× higher levels in the retina than the plasma, while in contrast DHCQ exhibits the opposite with much lower levels in plasma as compared to the retina in both HCQ and DHCQ dosed mice.

Further, DHCQ accumulated at higher levels in the surgical joint synovial tissue relative to the low levels measured in the retina, while in contrast HCQ accumulated at high levels in the retina relative to the low levels measured in the surgical joint synovial tissue (FIGS. 14 and 16). FIG. 16 displays the ratio of the level in surgical-side synovium/level in retina of DHCQ in DHCQ or HCQ dosed mice, and the ratio of the level in level in the surgical-side synovium/retina of DHCQ in DHCQ dosed mice. These data show that in both HCQ and DHCQ dosed mice, that DHCQ differentially accumulated in the surgical joint synovial tissue at high levels relative to the low levels that accumulated in the retina. In contrast, in HCQ dosed mice, levels of HCQ were higher in the retina relative to levels in the plasma or surgical joint tissue. Thus, DHCQ's preferential accumulation at high levels in the synovium of the surgical joint relative to the low levels in the retina, likely contribute to DHCQ being less likely than HCQ to cause retinal toxicity.

Mice, dosing with HCQ and DHCQ, isolation of specific tissues, and mass spectrometry measurement of HCQ and DHCQ levels in tissue samples. C57BL6 (B6) mice (n=5 per group) were treated with HCQ (100 mg/kg/day) or DHCQ (100 mg/kg/day) by oral gavage for 3 months. At experimental termination (3 months) mice were sacrificed and eyes removed under dissecting microscope. Curved microdissecting scissors was used to cut along the cornea and sclera, remove and discard the lens and visceral leaving the neural retina with eye shell to be placed in PBS and homogenized followed by centrifugation. Synovium was microdissected from the operated knee or the contralateral non-operated knee, normalized by weight of tissue, and placed in HPLC grade water before being homogenized and centrifuged. Plasma was obtained by tail bleeding. Plasma and tissue samples were precipitated with acetonitrile and levels of HCQ, DHCQ, BDCQ were evaluated by liquid chromatography/mass spectrometry (LC/MS) at Climax Laboratories, Inc. (San Jose, Calif.). The LC/MS analysis was conducted by using Shimazu 10A HPLC system (Shimadzu Scientific Instruments, Inc., Pleasanton, Calif.) with ACE C18, 50×2.1 HPLC column and ABSciex API-4000 Mass Spectrometer (ABSciex Corp. Foster City, Calif.) with Electrospray Ionization (ESI) and negative Multiple Reaction Monitoring (MRM) Scan. A gradient elution was used in separating the test compound with a mobile phase A (0.1% Formic Acid in 5 mM of NH4AC) and B (0.1% Formic acid in acetonitrile).

Example 11

Figure 17:
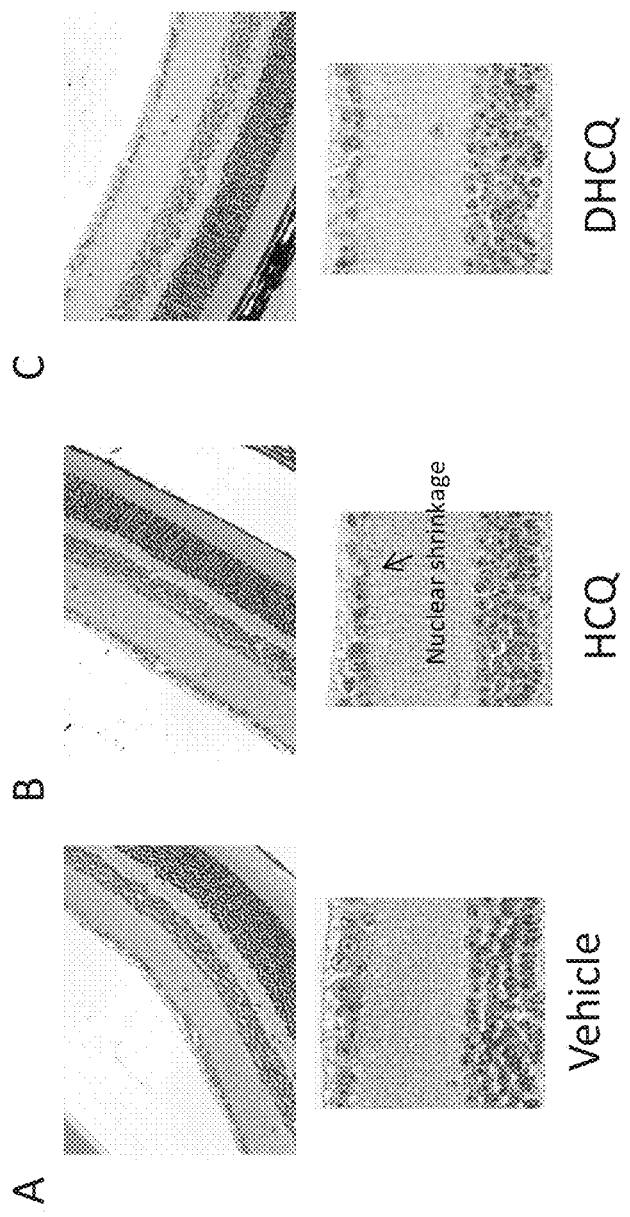
FIG. 17 shows micrographs of retinal cell layers of mice treated with vehicle, HCQ, and DHCQ, showing ganglion cell layer nuclear shrinkage.

Analysis of Retinal Histology Demonstrates that In Vivo Treatment with DHCQ is Associated with Less Retinal Toxicity and Cell Death as Compared to Treatment with HCQ From groups of mice (n=5) dosed with HCQ 100 mg/kg/day or DHCQ 100 mg/kg/day for 3 months as described in Example 10 and FIGS. 13-16, analysis of the retina was performed and demonstrated reduced retinal toxicity in mice treated with DHCQ as compared to mice treated with HCQ. At the time of termination, the eyes from each treatment group were carefully microdissected to ensure the retina remained intact, the eye was fixed in formalin, and the fixed eye sectioned to visualize the retina. The retinal cell layer was stained with hematoxylin and eosin (H&E), and evaluated for number of nuclei in the ganglion cell layer (GCL), as well as nuclear shrinkage in the GCL which is suggestive of a selective loss of retinal ganglion cells. Based on the result presented in FIG. 17, increased nuclear shrinkage in the GCL was observed in mice treated with HCQ (FIG. 17B). No increase in nuclear shrinkage in the GCL was observed in the groups of mice treated with DHCQ (FIG. 17C). Representative images of H&E stained retinal sections are presented from each treatment group in FIG. 17.

Figure 18:
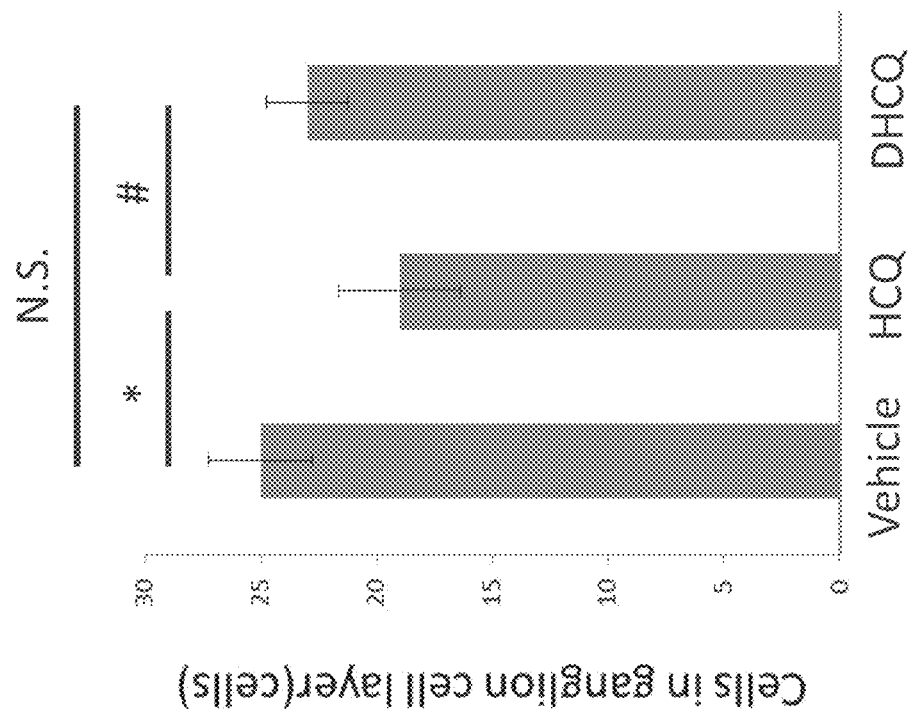
FIG. 18 is a chart comparing the number of cells in the ganglion cell layer for mice treated with vehicle, HCQ, and DHCQ.

Using the histologic and quantitative pathology methodology adapted from Shichiri, et al (Shichiri, et al, JBC. 2012, 287(4):2926-34. PMID 22147702), the H&E stained retinal sections were evaluated for number of nuclei in the ganglion cell layer (GCL) (FIG. 18). The graph presents quantitation of the number of nuclei in the GCL of the retina from the indicated treatment groups. The number of cells in the GCL of the retina for each treatment group was compared with the number of cells in vehicle-treated control by two-tailed T test. As compared to the retinas from vehicle-treated control mice, we found that the number of cells in the GCL was significantly lower in mice treated with HCQ as compared to mice treated with vehicle (* P<0.05) (FIG. 18). In contrast, as compared to retinas from vehicle-treated control mice, there was no reduction in the number of cells in the GCL in retinas from mice treated with DHCQ (N.S.=non-significant) (FIG. 18). Further, we statistically compared the number of cells in the GCL in retinas from DHCQ treated as compared to HCQ treated mice, and demonstrated that HCQ treatment resulted statistically increased retinal cell loss as compared to DHCQ treatment (# P<0.05) (FIG. 18).

These results demonstrate that treatment with DHCQ results in statistically less retinal toxicity (retinopathy) as compared to treatment with HCQ.

Example 12

Treatment with DHCQ or the Combination of DHCQ+Atorvastatin Prevented the Development of and Reduced the Severity of Murine Osteoarthritis (OA)

Figure 19:
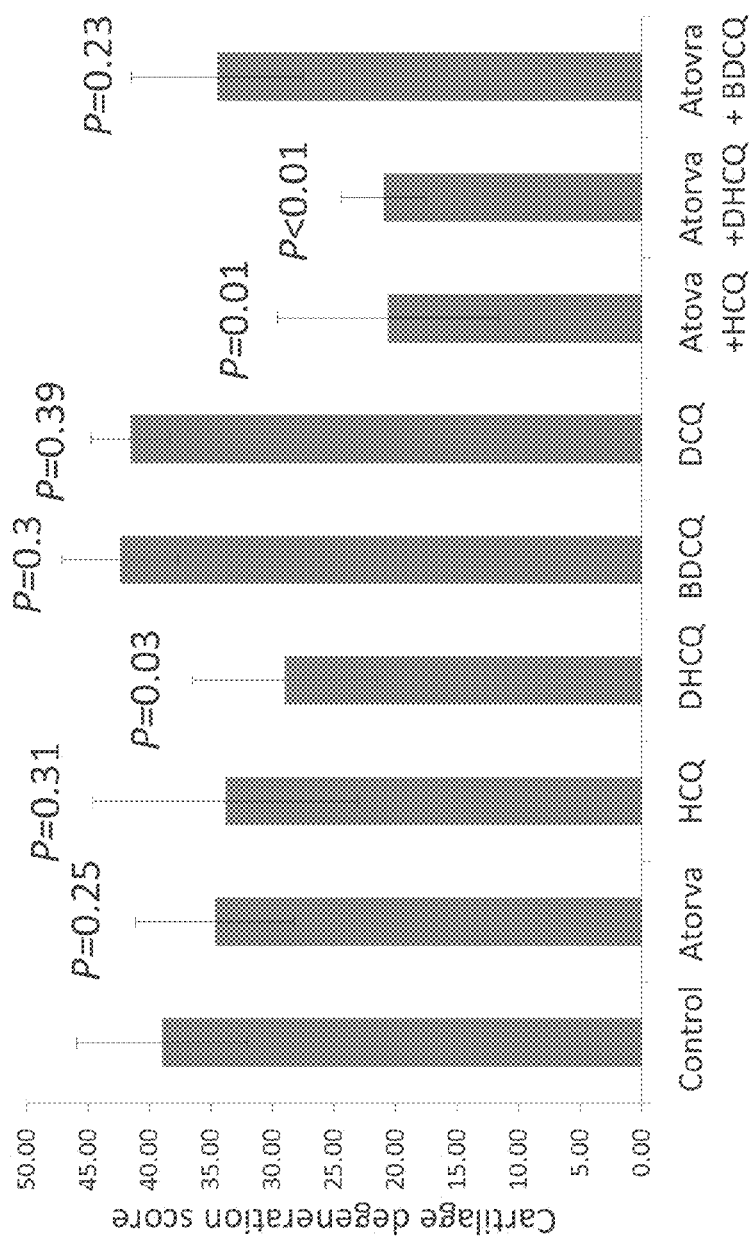
FIG. 19 is a chart comparing cartilage degeneration scores for mice treated with vehicle, atorvastatin, HCQ, DHCQ, BDCQ, DCQ, atorvastatin+HCQ, atorvastatin+DHCQ, and atorvastatin+BDCQ.

FIG. 19 presents the results comparing cartilage degeneration scores for the groups of mice treated with atorvastatin, HCQ, DHCQ, BDCQ, DCQ, atorvastatin+HCQ, atorvastatin+DHCQ, or atorvastatin+BDCQ. The combinations of DHCQ+atorvastatin and HCQ+atorvastatin prevented the development of and reduced the severity of osteoarthritis (OA) in a mouse model. C57BL6 (B6) mice (n=7-10 per group) were surgically induced to develop OA by destabilization of the medial meniscus (DMM). One week following surgical induction, a timepoint at which the mice were asymptomatic or exhibit mild pre-OA joint symptoms, treatment was initiated with one or more of the following molecules: atorvastatin 40 mg/kg/day, HCQ (HCQ) 100 mg/kg/day, DHCQ 100 mg/kg/day, desethylchloroquine (DCQ) 100 mg/kg/day, or bisdesethylhydroxychloroquine (BDCQ) 100 mg/kg/day, as individual or combinations of molecules (as labeled in the figure), all delivered by oral gavage once per day. After 3 months, mice were sacrificed, joints harvested, joint sections cut, and tissue sections stained with safranin-O. The mean "Cartilage degeneration scores" in safranin-O stained sections of the medial region of stifle joints are presented in the graph. Two-tailed T tests were used to compare the Cartilage Degeneration Scores for each group as compared to the vehicle control group.

FIG. 20 is a table comparing the "cartilage degeneration scores", "osteophyte scores", and "synovitis scores" (for a description of these scores, see Wang et al, Identification of a critical role for complement in osteoarthritis. Nature Medicine, 2011, 17(12):1674-9) for the groups of mice treated with atorvastatin, HCQ, DHCQ, BDCQ, DCQ, HCQ+atorvastatin, DHCQ+atorvastatin, or BDCQ+atorvastatin. The combinations of DHCQ+atorvastatin, and HCQ+atorvastatin, prevented the development of OA and reduced the severity of the Cartilage Degeneration Score in a mouse model of OA. From the mouse OA experiment presented in FIG. 19, the mean "Cartilage degeneration scores" in safranin-O stained sections of the medial region of stifle joints were compared between the vehicle treated group and each of the other treatment groups by two-tailed T tests, and it was demonstrated that the combination of DHCQ+atorvastatin, as well as HCQ+atorvastatin, both statistically reduced synovitis (inflammation) in the joint (P<0.01), prevented the development of OA (P<0.01), and reduced the severity of OA (P<0.01) as compared to vehicle-treated mice FIG. 21 is a table comparing the cartilage degeneration scores, osteophyte scores, and synovitis scores for subjects treated with combinations of HCQ, DHCQ, BDCQ, or DCQ with atorvastatin, versus monotherapies with HCQ, DHCQ, or atorvastatin alone. Protective effect of DHCQ+atorvastatin, and HCQ+atorvastatin, compared with either HCQ or atorvastatin monotherapy alone in murine OA. From the mouse OA experiment presented in FIG. 19, the mean "Cartilage degeneration scores", "Osteophyte scores", and "Synovitis scores" were compared between the individual single drug treated groups (e.g. atorvastatin-treated, or HCQ-treated, or DHCQ-treated) and each of the combination-treated groups (e.g. DHCQ+atorvastatin, or HCQ+atorvastatin) by two-tailed T tests, and it was demonstrated that the combination of DHCQ+atorvastatin as well as HCQ+atorvastatin both statistically reduced synovitis (inflammation) in the OA joint (P<0.01), prevented the development of OA (P<0.01), and reduced the severity of OA (P<0.01) as compared to vehicle-treated mice.

Treatment with DHCQ alone reduced the "Cartilage Degeneration Score" as compared to treatment with vehicle (P=0.03 by two-tailed T test) (FIGS. 19 and 20). In contrast, treatment with either HCQ alone or atorvastatin alone only resulted in trends towards improvement in the "Cartilage Degeneration Score" (FIGS. 19 and 20). The combination of DHCQ+atorvastatin statistically reduced the "Cartilage Degeneration Score" by two-tailed T test both as compared the vehicle treated group (P<0.01), as well as compared to treatment with either DHCQ alone or atorvastatin alone (P<0.05) (FIG. 21). In addition, treatment with DHCQ alone resulted in statistically significant protection against the development of synovitis and osteophytes as compared to treatment with vehicle (FIG. 20), and the combination of DHCQ+atorvastatin provided even more powerful and statistically significant prevention and reduction in the development of synovitis and osteophytes as compared to treatment with either drug along (FIG. 21).

Thus, it is demonstrated that DHCQ, or a combination of DHCQ+atorvastatin, prevented development of and reduced the severity of osteoarthritis.

Example 13

Figure 22:
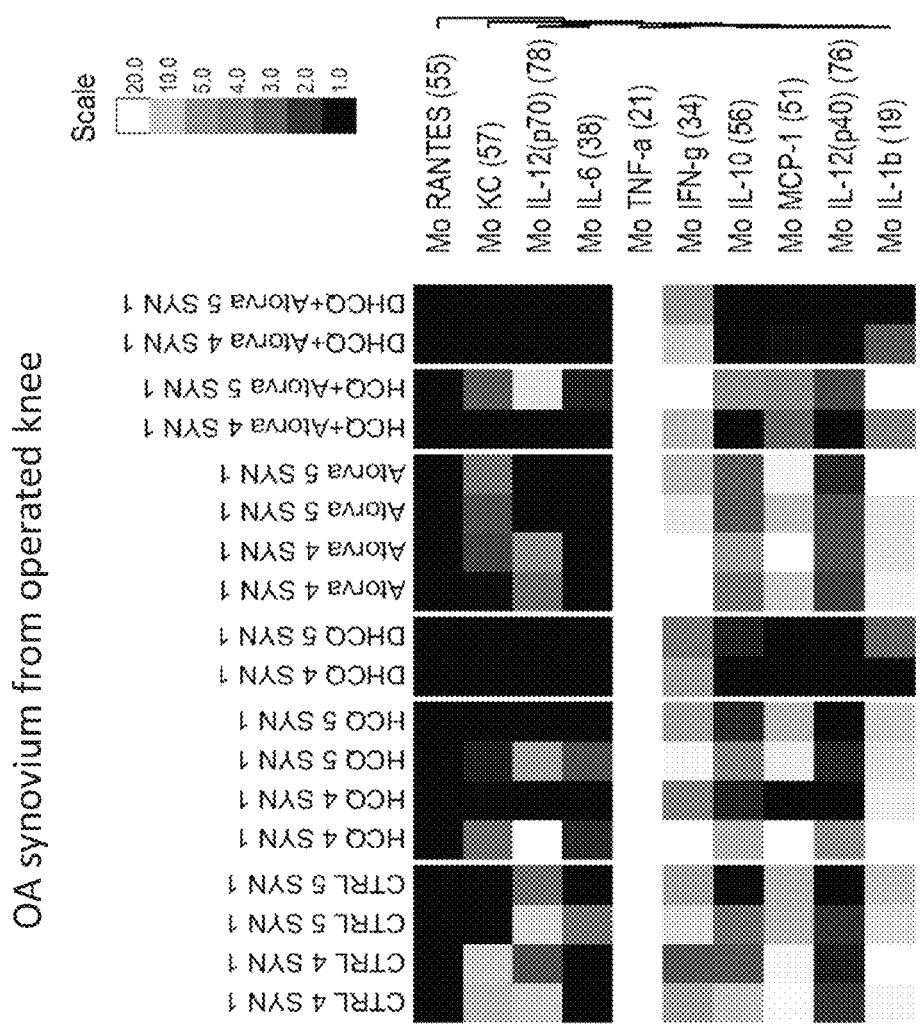
FIG. 22 shows heatmap panels representing levels of inflammatory cytokines in synovial tissues derived from mice with osteoarthritis treated with vehicle (CTRL), HCQ, DHCQ, atorvastatin (Atorva), HCQ+atorvastatin, and DHCQ+atorvastatin.
Figure 23:
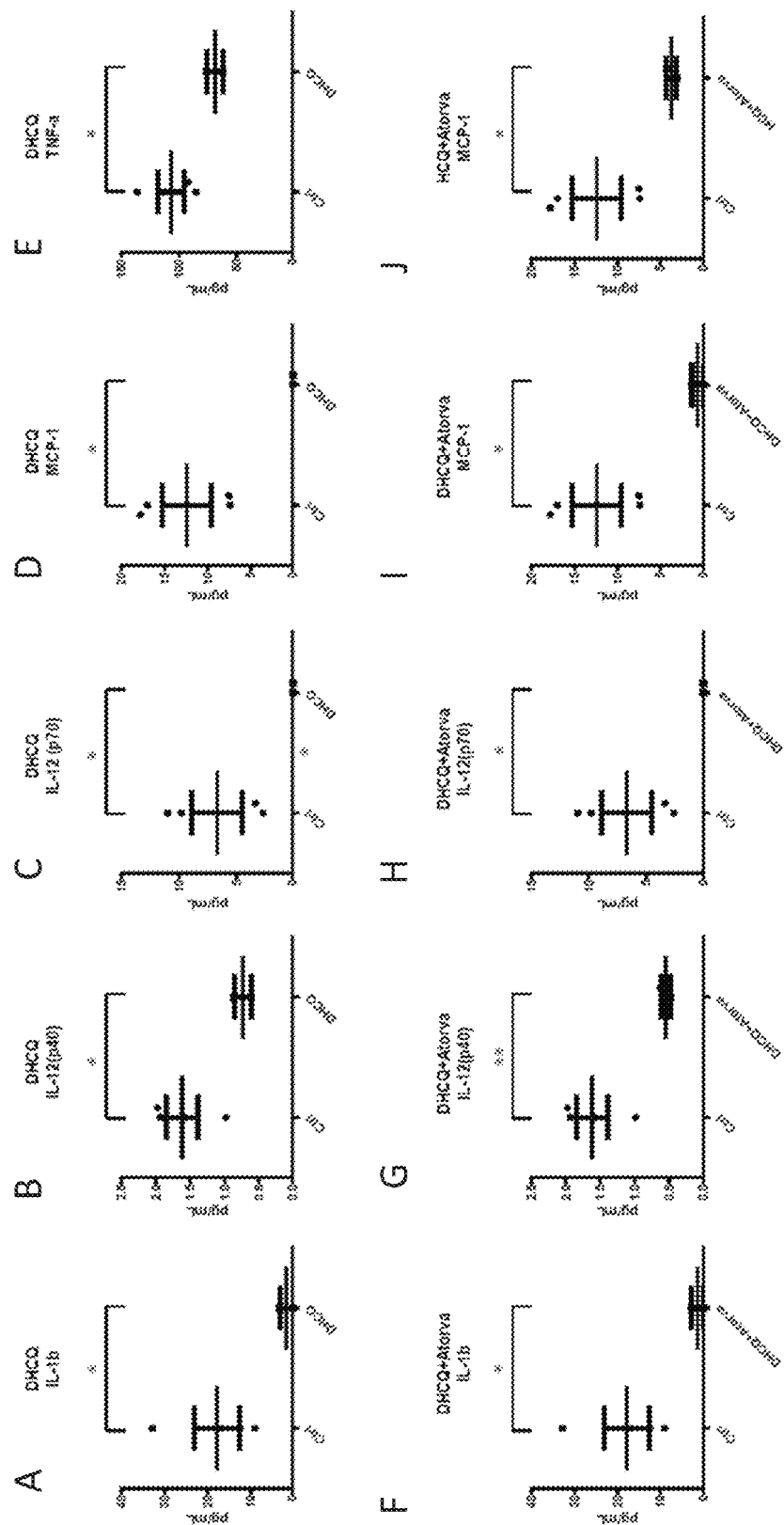
FIG. 23 shows charts comparing levels of inflammatory cytokines for various treatments.
Figure 24:
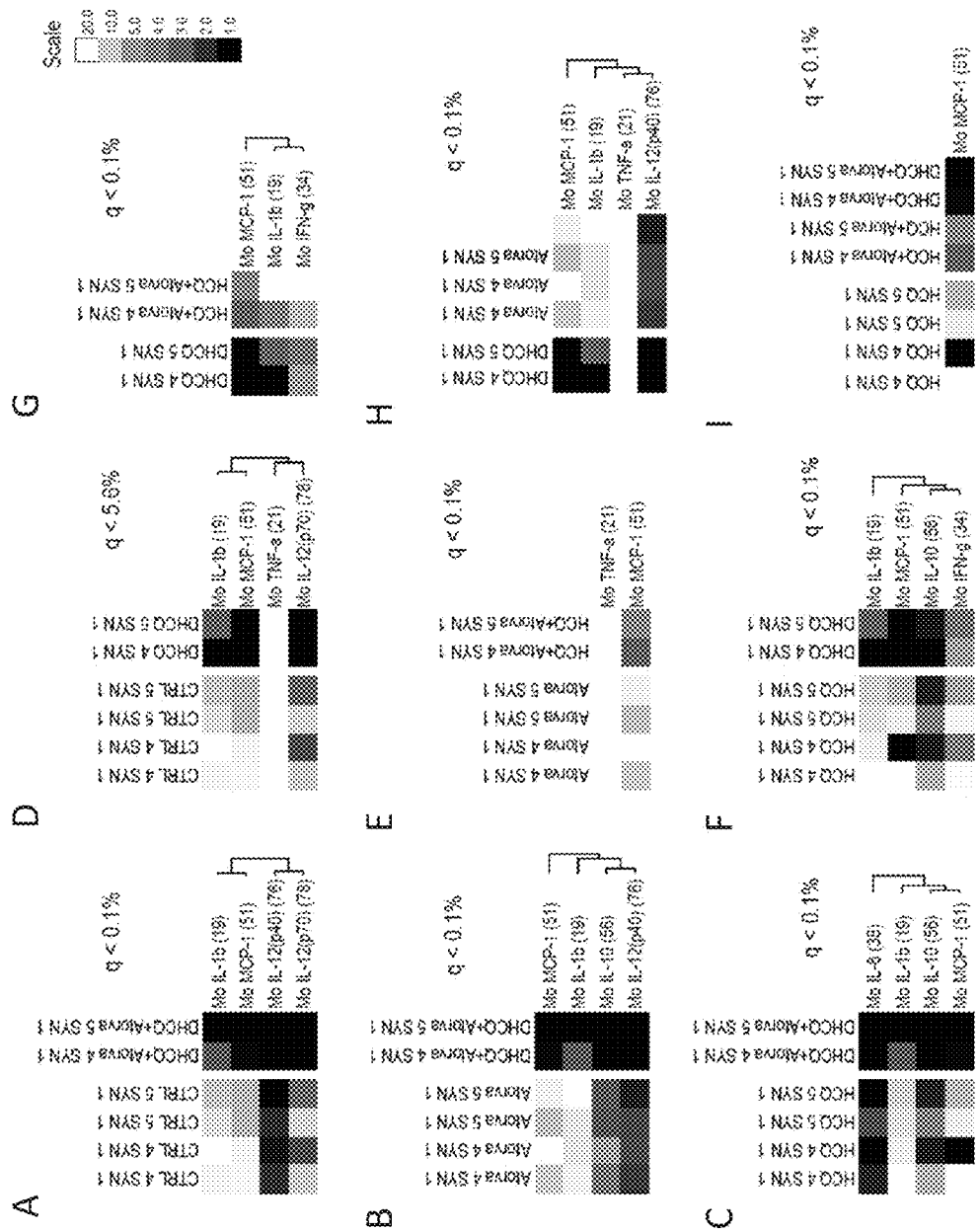
FIG. 24 shows heatmap panels comparing levels of inflammatory cytokines for various treatments.

DHCQ, the Combination of DHCQ+Atorvastatin, and the Combination of HCQ+Atorvastatin, Inhibit Development of Inflammatory Cytokine Production in Synovium in a Mouse Model of OA From a parallel experiment to the mouse OA experiment presented in Example 12 and FIG. 19, following in vivo dosing and at the time of termination OA synovial tissue was microdissected, homogenized to form a lysate, centrifuged, and supernatants assayed for levels of inflammatory cytokines using a multiplex bead-based cytokine assay (BioRad Laboratories, Hercules, Calif.). FIG. 22 demonstrates a heat map representing levels of inflammatory cytokines in mouse OA synovium (SNY) derived from vehicle treated (CTRL), hydroxychloroquine treated mice (HCQ), desethylhydroxychloroquine treated mice (DHCQ), atorvastatin treated mice (Atorva), mice treated with the combination of HCQ+Atorva, and mice treated with the combination of DHCQ+Atorva. The results of two independent measurements from each of two independent mice from each treatment group are presented and analyzed. Compared with vehicle control-treated mice, levels of inflammatory cytokines in OA synovium were lower in mice treated with HCQ alone or DHCQ alone, and were lower still in those treated with a combination of HCQ+atorvastatin, and were lowest in mice treated with a combination of DHCQ+atorvastatin (FIG. 22). Similarly, FIGS. 22 and 23 demonstrate lower levels of multiple inflammatory cytokines in mouse OA synovial tissue from mice treated with DHCQ alone as compared to treatment with vehicle control (FIGS. 22 and 23 A-E), as well as in mice treated with DHCQ+atorvastatin as compared to treatment with vehicle control (FIGS. 22 and 23 F-I). Treatment with the combination of HCQ+atorvastatin also inhibited the production of inflammatory cytokines as compared to treatment with vehicle control (FIGS. 22 and 23J). FIG. 24 demonstrates high dimensionality analysis of multiple cytokines using the Significance Analysis of Microarrays algorithm and software (Tusher, et al., PNAS. 2001 98(9): 5116-21. PMID 11309499) to identify cytokines differentially produced in OA synovium from various treatment groups as identified by a false discovery rate <0.1% (q-value). As demonstrated in FIG. 24:

Compared with HCQ monotherapy, treatment with the combination of HCQ+atorvastatin resulted in significantly lower levels of MCP-1 (FIG. 24 I).

Compared with atorvastatin monotherapy, the combination of HCQ+atorvastatin resulted in significantly lower levels of TNFα and MCP1.

Compared with vehicle control treatment, treatment with the combination of DHCQ+atorvastatin resulted in significantly lower levels of IL-1β, MCP-1, IL12p40, and IL-12p70.

Compared with atorvastatin monotherapy, treatment with the combination of DHCQ+atorvastatin resulted in significantly lower levels of IL-1β, MCP-1, IL12p40, and IL-10.

DHCQ monotherapy reduced the levels of multiple inflammatory cytokines including IL-1b, MCP-1, IFNγ, TNF-alpha IL12p40, and IL-12p70 as compared to treatment with vehicle control, atorvastatin alone (FIG. 24 H), HCQ+atorvastatin (FIG. 24 G), and HCQ alone (FIG. 24 F).

Example 14

A Combination of HCQ+Atorvastatin Results in a Reduction of Synovitis and Improvement in Pain and Functional Scores in Human Subjects with Medial-Compartment Knee OA in a 16-Week Open-Label Pilot Clinical Trial (NCT01645176)

Nearly 27 million people in the U.S. have some form of osteoarthritis (OA) which has increased from 21 million in 1990. Knee OA is prevalent in 16% of all adults 45 years and older. In Canada, OA affects 10% of the entire population. In 2005, the estimated annual lost productive time of U.S. workers due to OA exceeded $70 billion. A population based study conducted from 1990 to 2000 showed the incidence of total knee replacements in patients aged >45 years increased 81.5% during that period. Total charges for total knee replacements to the US healthcare system in 2000 were approximately $148 million.

Medical therapies used to treat OA include non-steroidal anti-inflammatory drugs (NSAIDs), acetaminophen, intraarticular corticosteroids, intraarticular hyaluronic acid formulations, narcotics, and physical therapy. While all of these may alleviate the symptoms associated with OA, there are no medical therapies currently available which prevent the progression of cartilage loss or reverse the disease process. In patients with more severe knee OA, total joint replacement surgery is an option. The incidence of total knee replacement is steadily rising and OA is the leading cause of knee replacement surgery. The increased incidence of knee replacement surgery is putting a burden on the healthcare system as well as creating a risk for surgical complications.

Preclinical studies demonstrated that Arthrostatin, a combination of HCQ+atorvastatin, prevents the development of OA in the destabilization of the medial meniscus (DMM) mouse model (FIGS. 19-21). The combination of HCQ+ atorvastatin provided statistically significant benefit in this model, while several other combinations and treatment with HCQ or atorvastatin alone did not result in a statistically significant reduction in the severity of OA.

To date, HCQ has been tested in human OA and exhibited trends towards therapeutic benefit in case series in erosive OA, but has not demonstrated disease-modifying or pain-reducing activity in non-erosive OA.

A primary objective of the clinical trial is evaluation of the efficacy of Arthrostatin for the treatment of osteoarthritis (non-erosive) measuring differences in change synovitis of the knee between 0 and 24 weeks as measured by MRI in patients with OA. A secondary objective is evaluation of the safety and tolerability of study agent over 24 weeks and evaluation of the impact of the study agent on pain and function over 24 weeks. Exploratory objectives are ultrasound assessment of synovitis; and marker analysis, including markers of cartilage breakdown, metabolism and inflammation. To date, 7 human medial compartment knee OA patients have completed 16 weeks of dosing, including all baseline, in-life and follow-up examinations, tests and gadolinium-enhanced MRI imaging studies.

The primary endpoint for this study is determination of the proportion of subjects treated with Athrostatin achieving meaningful improvement in synovitis based on a reduction in the synovitis score (Guermazi et al., Ann Rheum Dis. 2011 70(5):805-11. PMID: 21187293) as measured by Gd-MRI by greater than 4 points at 24 weeks in patients treated with Arthrostatin as measured by MRI at 24 week. The overriding hypothesis for this pilot trial is that interventions that reduce the low-grade synovitis OA (as measured by Gd-MRI) in this open-label pilot trial, will provide chondroprotective effects and reduce the progression of OA in subsequent Phase II and Phase III clinical trials.

The Secondary Endpoints include the safety and tolerability of Arthrostatin in subjects with early OA; change from baseline to Weeks 4, 12 and 24 in the WOMAC pain subscale and change from baseline to Weeks 4, 12 and 24 in the WOMAC function subscale; change from baseline to Weeks 4, 12 and 24 in the Patient's Global VAS; analysis of efficacy data using the OMERACT-OARSI Responder Index (Onel et al, Clin Drug Investig. 2008; 28(1):37-45. PMID: 18081359); change from baseline to Weeks 4, 12 and 24 weeks in HAQ-DI; change from baseline to Weeks 4, 12 and 24 in the Physician's Global VAS; and to determine the use of rescue medications required at 4, 12 and 24 weeks.

Subjects with OA were recruited and informed consent was obtained. During a screening period lasting up to 34 days, subjects underwent medical and arthritis history, physical examination, and complete the WOMAC pain and function subscale questionnaires and patient VAS global assessment. ECG, bilateral knee x-rays and MRI of the index knee is performed and concomitant medications are recorded. Samples were obtained for urinalysis, hematology, blood chemistry, and a urine pregnancy test (for women of childbearing potential). Vital signs and weight are recorded. Subjects are asked to maintain their usual dose of NSAIDs and/or other analgesics during the course of the trial, except during the 48 hour period or 24 hour for acetaminophen preceding efficacy assessments (WOMAC and HAQ questionnaires, and Patient Global Assessment VAS) at Day 1 (baseline), and Weeks 2, 4, 12 and 24.

Subjects who met all of the inclusion criteria and none of the exclusion criteria were entered into the study on Day 1 and will receive Arthrostatin. Additional follow-up visits are conducted at Weeks 2, 4, 12 and 24 and safety and efficacy assessments performed according to the Schedule of Assessments. Telephone follow-up visits will occur at Weeks 8, 16, and 20. The dosing regimen is HCQ 400 mg/d and atorvastatin 40 mg/d.

Inclusion Criteria (abnormal markers): 1. Ambulatory subjects with OA of the knee with symptoms for at least 6 months and pain on the majority of days in the last 30 days (assessment of abnormal clinical markers). Symptoms must include knee joint pain. In subjects with bilateral knee OA, the more symptomatic knee is the index knee (assessment of abnormal clinical markers). 2. Male or female adults age >40 years with a body mass index <35 (measurement of abnormal metabolic marker). 3. Radiographic evidence of at least one osteophyte in either knee on posteroanterior (PA) and lateral standing, flexed x-ray (measurement of abnormal imaging marker). 4. An OARSI Atlas joint space narrowing grade of 1 or 2 in the index knee (imaging of abnormal imaging marker). 5. A WOMAC pain score of >8 on the index knee at screening visit 2 and at Day 1/baseline visit (measurement of abnormal clinical marker). 6. A synovitis score of 9-14 based on gadolinium-enhanced MRI (Gd-MRI) of the index knee and the scoring system (based on summed scores from 11 sites) described in Guermazi et al (Ann Rheum Dis. 2011 70(5):805-11. PMID: 21187293) (measurement of abnormal imaging marker). 7. Able to comply with the study and give informed consent. 8. Able to read, write and understand English.

For this trial, candidate patients were assessed for evidence of the low-grade inflammatory disease OA based on the required presence of multiple abnormal clinical and laboratory markers. Clinical markers measured and required for trial entry included knee pain for at least 6 months, knee pain localizing to one side, and a WOMAC pain score >8. In addition, two imaging markers were required for trial entry including radiographic evidence of at least one osteophyte in either knee on posteroanterior (PA) and lateral standing flexed x-ray and a synovitis score of 9-14 based on gadolinium-enhanced MRI (Gd-MRI) of the index knee and the scoring system (based on summed scores from 11 sites) described in Guermazi et al (Ann Rheum Dis. 2011 70(5): 805-11. PMID: 21187293) (measurement of abnormal imaging marker). Based on the measurement and detection of these abnormal clinical and abnormal imaging markers (as described in detail in the inclusion criteria), individuals were enrolled in the pilot trial and treated with the combination of HCQ+atorvastatin.

Exclusion Criteria: 1. A requirement for treatment with high potency opioids for pain relief. 2. Unwilling to abstain from NSAIDs and/or other analgesic medications except acetaminophen (i.e., COX-2 inhibitors, tramadol) for 48 hours and acetaminophen for 24 hours prior to pain assessments during the study. Subjects taking low dose aspirin for cardiovascular health may remain on their stable dose throughout the study. 3. On an unstable dose of NSAIDs or analgesics for at least 3 months prior to screening visit 1. 4. Using a handicap assistance device (i.e., cane, walker) >50% of the time. 5. Undergoing new physical therapy or participating in a weight loss or exercise program that has not been stable for at least 3 months prior to screening visit 1 and will not remain stable during their participation in the study. 6. Had a previous history of arthroscopic or open surgery to the index knee in the past 6 months or planned surgery during study follow up. 7. Had joint replacement surgery in the index knee. 8. Received corticosteroid, short acting hyaluronic acid, or other intraarticular injections of the index knee within 3 months of screening visit 1 and/or not willing to abstain from treatments for the duration of the study. 9. A history in the past 5-10 years of reactive arthritis, rheumatoid arthritis, psoriatic arthritis, ankylosing spondylitis, arthritis associated with inflammatory bowel disease, sarcoidosis, amyloidosis or fibromyalgia. 10. Clinical signs and symptoms of active knee infection or radiographic evidence of crystal disease other than chondrocalcinosis (i.e., gout and CPPD). 11. A history of abnormal laboratory results >2.5×ULN indicative of any significant medical disease, which in the opinion of the investigator, would preclude the subjects participation in the study. 12. Any of the following abnormal laboratory results during screening: a. ALT and AST >2.5×ULN b. Hemaglobin <9 g/dL c. WBC <3500 cells/mm3. d. Lymphocyte count <1000 cells/mm$^3$ e. Serum creatinine >1.5×ULN. 13. A history of malignancy in the past ten years (<10 years), with the exception of resected basal cell carcinoma, squamous cell carcinoma of the skin, or resected cervical atypia or carcinoma in situ. 14. Significant hip pain, ipsilateral to the index knee that may interfere with assessments of index knee pain. 15. A known or clinically suspected infection with human immunodeficiency virus (HIV), or hepatitis C or B viruses. 16. Participated within 3 months or will participate concurrently in another investigational drug or vaccine study. 17. A history of drug or alcohol dependence or abuse in the past 3 years 18. A female with reproductive capability who is unwilling to use birth control for the duration of the study and/or intends to conceive within 12 months of dosing. 19. Other serious, non-malignant, significant, acute or chronic medical or psychiatric illness that, in the judgment of the investigator, could compromise subject safety, limit the subject's ability to complete the study, and/or compromise the objectives of the study.

All subjects are monitored for AEs during the study. Assessments may include monitoring of any or all of the following parameters: the subject's clinical symptoms; laboratory, pathological, radiological, or surgical findings; physical examination findings; or other appropriate tests and procedures. AEs that cause a subject to discontinue study participation must be followed up until either the event resolves, stabilizes, or returns to baseline (if a baseline assessment is available).

Figure 25:
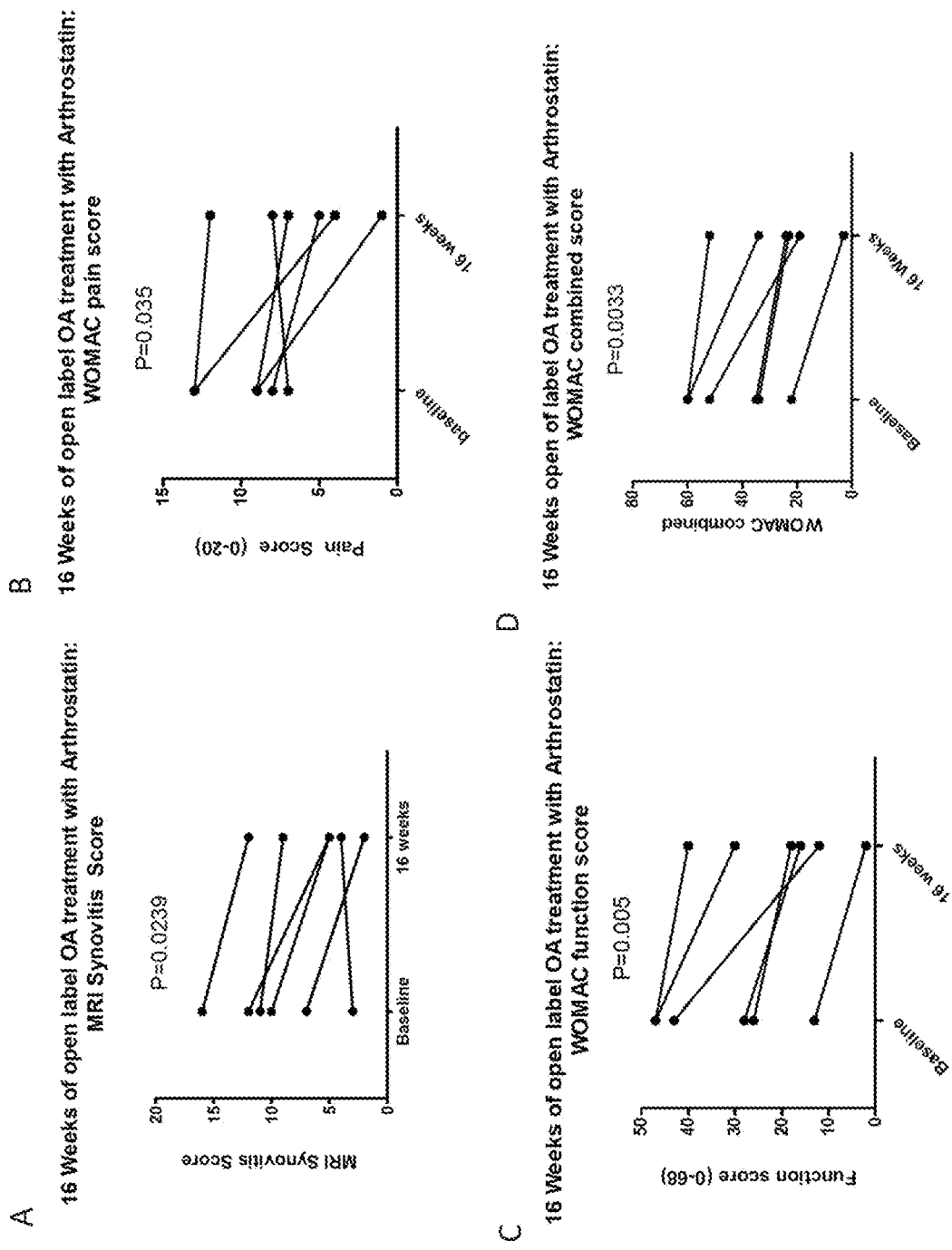
FIG. 25 shows various scores related to inflammation and pain observed for subjects with medial-compartment knee osteoarthritis in a 16-week open-label clinical trial (NCT01645176).

This trial is entitled "Hydroxychloroquine/Atorvastatin in the Treatment of Osteoarthritis (OA) of the Knee" and was registered on ClinicalTrials.gov as NCT01645176. To date, 7 human medial compartment knee OA patients have met inclusion criteria and been enrolled. There were no dropouts of subjects who initiated combination HCQ+atorvastatin therapy in our trial. There were no serious adverse events in the trial. All 7 subjects have now completed 16 weeks of dosing, including all baseline, in-life and follow-up examinations, tests and gadolinium-enhanced MRI imaging studies. As presented in FIG. 25, a combination of HCQ+atorvastatin (the combination termed "Arthrostatin") reduced joint inflammation in humans with medial-compartment knee OA in this 16-week open-label clinical trial. The MRI Synovitis Score was measured by gadolinium-enhanced MRI scanning of the affected knee in each subject at baseline and at the end of the 16-week in-life HCQ+atorvastatin treatment period, and represents the degree of inflammation in the joint. Only candidate subjects with an abnormal MRI synovitis score of 9-14, along with other clinical and inflammatory markers, were enrolled and treated. Subjects were treated with a combination of HCQ 600 mg by mouth each day and atorvastatin 40 mg by mouth each day for 16 weeks. The MRI Synovitis Scores were analyzed by two-way paired T test, which demonstrated that treatment with a combination of HCQ+atorvastatin statistically reduced the amount of synovitis (inflammation) in the affected knee joints (P=0.024) (FIG. 25).

Further, in the 7 medial-compartment knee OA patients enrolled, a combination of HCQ+atorvastatin reduced the WOMAC Pain Score, WOMAC Function Score and WOMAC Combined Score in human with medial-compartment knee OA patients in this 16-week open-label clinical trial. In this trial, we also measured Western Ontario and McMaster Universities Arthritis Index (WOMAC) Pain, Functional and Combined Scores (see McConnell et al., The Western Ontario and McMaster Universities Osteoarthritis Index (WOMAC): a review of its utility and measurement properties. Arthritis Rheum 2001; 45: 453-61. PMID: 11642645). The WOMAC Pain, Function and Combined scores were analyzed by one-tailed T tests, which demonstrated that treatment with a combination of HCQ+atorvastatin statistically reduced the WOMAC Pain Score at 16 weeks (P=0.035), WOMAC Function Score (P=0.005), and the WOMAC Combined Score (P=0.003) (FIG. 25 B-D).

Thus, our 16-week open-label pilot trial of the combination of HCQ+atorvastatin in humans with medial-compartment knee OA demonstrates that this combination reduced synovitis (inflammation) in the affected knee (P=0.024; FIG. 25 A), and resulted in improvements in the WOMAC Pain, Function and Combined Scores (FIG. 25 B-D). Together, these data suggest that a combination of HCQ+atorvastatin provides meaningful clinical benefit to, and reduced inflammation in, and thus may reduce OA disease progression in humans.

Drugs that reduce inflammation may provide disease-slowing effects including chondroprotection (e.g. reduction in the rate of cartilage breakdown). Specifically, the combination of HCQ+atorvastatin may not only reduce synovitis but that this reduction in synovitis will result in a slowing of OA disease progression. This slowing of OA disease progression in subsequent phase II and phase III trials will be demonstrated by weight-bearing plain film X-rays of the affected knee that demonstrate preservation of joint space (e.g. slowing of the narrowing of the joint space in the medial compartment of the affected knee) and/or that knee MRI scans will demonstrate preservation of cartilage volume and/or integrity (and thus slowing of disease progression).

New methods are being developed for measuring cartilage volume and integrity, and these new methods will be used in subsequent phase II and phase III studies to demonstrate that HCQ+atorvastatin together protect against cartilage loss in human OA. An example of the methods for analyzing joint space narrowing by plain X-ray in medial-compartment knee OA are described in Brandt et al. (Arthritis and Rheumatism, 52(7):2015-2025, PMID: 15986343), and the slowing of joint space narrowing is considered to demonstrate disease-slowing activity in OA. A second and more sensitive method to demonstrate chondroprotection is the demonstration of preservation of cartilage volume on MRI scan, and an example of methods of using MRI to demonstrate cartilage volume preservation are described in Raynauld et al. (Ann Rheum Dis. 2009, 68(6):938-47. PMID: 18653484).

Given the potent anti-inflammatory properties of DHCQ, DHCQ+atorvastatin could provide even more greater efficacy in reducing synovitis on Gd-MRI, reducing WOMAC pain scores, and improving WOMAC function scores in human OA.

Example 15

Use of DHCQ, or Combination Therapy with DHCQ+Atorvastatin, to Prevent Development of Osteoarthritis (OA)

Humans are screened for evidence of early OA or increased risk for the development of OA. Many factors can put humans in a preclinical OA disease state including joint injury, joint surgery, degenerative meniscal tears, degeneration of articular cartilage, anterior cruciate ligament tears, collagen and other matrix protein defects, genetic predisposition, and other factors. Humans in the process of developing OA or with features of early OA can be treated with DHCQ or with a combination of DHCQ+atorvastatin to prevent the development and progression of OA. Further, humans at risk for OA or with early OA can be further tested for the presence of inflammation in the involved joint to identify individuals most-likely to respond to treatment with DHCQ or with DHCQ+atorvastatin. Testing for joint inflammation can be performed with imaging markers, such as MRI with or without gadolinium contrast, or an ultrasound, to determine if one or more of the following abnormal imaging markers indicative of inflammation are present: synovial enhancement or proliferation, an effusion is present, and bone marrow edema. Molecular markers of inflammation can also be tested to identify abnormal molecular inflammatory markers, including abnormal levels of one or more of CRP, ESR and inflammatory cytokines. Finally, clinical history and exam can be used to assess inflammation—including the presence of abnormal clinical markers including an effusion on physical exam or morning stiffness on history.

The dose of DHCQ can be about 400 mg/day (about 6.7 mg/kg/day), but can be about 500 mg/day (about 8.3 mg/kg/day), or can be about 550 mg per day (9.16 mg/kg/day), or can be about 600 mg/day (about 10 mg/kg/day), or can be about 800 mg/day (about 13.3 mg/kg/day), or can be between 100-1600 mg/day (about 1.6-26.67 mg/kg/day). The dose of atorvastatin is generally about 20 or about 40 mg/day (about 0.33-0.66 mg/kg/day), but can be between about 5 and 80 mg/day (about 0.08-1.3 mg/kg/day). The DHCQ, or DHCQ+atorvastatin, can be delivered in individual tablets or capsules, or in a combined tablet or capsule that includes both drugs.

Examples of humans at high risk for development and with preclinical OA, and their treatment with DHCQ or combination therapy with DHCQ+atorvastatin, include:

(1) A 59 year old male with knee pain is diagnosed with osteoarthritis of the R knee (Kellgren-Lawrence, K-L, grade II). He is limited when running and sitting for prolonged periods by the sensation of stiffness or "gelling" in his knee. His R knee range of motion is intact and there is no deformity of angulation of adduction moment on ambulation. Assessment is performed using the Western Ontario and McMaster Universities (WOMAC) OA index for assessment of pain, function and stiffness of the knee joint as well as a score of 1-100 using a visual analog score (VAS) for pain. The patient undergoes MRI with gadolinium of the R knee which measures and reveals enhancement consistent with synovitis which is assessed using a semi-quantitative scoring system. Based on the abnormal clinical and imaging markers, the patient is determined to be in the early-stages of OA and is therefore treated with a DHCQ 550 mg taken once daily as a combination capsule. Another MRI is repeated at six months along with an evaluation to determine if there is a decrease in synovitis.

(2) 44 year old male amateur rugby player develops left knee pain and clicking with running. He is evaluated by X-ray which demonstrates K-L grade 1 changes and a knee MRI which reveals a posterior meniscal tear and he is scheduled for arthroscopic debridement. Blood tests reveal an elevated (abnormal) C-reactive protein (CRP) of 3.1. Beginning one month before surgical debridement the patient is treated with DHCQ 200 mg daily for 1 week, then 800 mg daily for 3 weeks, then 600 mg daily thereafter.

(3) 54 year old male presents with mild intermittent locking in his left knee. X-ray reveals K-L grade 1 OA and ultrasound demonstrates a degenerative meniscal tear and moderate synovial enhancement consistent with synovitis. The patient is offered arthroscopic meniscal debridement but declines surgical intervention. He is prescribed DHCQ 600 mg.

(4) 28 year old male develops a fracture of his right ankle (tibial plafond) with appropriate reduction and casting. His X-rays do not show any features of OA. Given the 30% risk of significant radiographic OA within 2-4 years increasing to 74 percent by 11 years after fracture, the patient is monitored for evidence of joint inflammation by ultrasound and MRI, and/or by molecular markers. Ultrasound detects (measures) a synovial effusion and synovitis, and as a result the patient is determined to be at increased risk for progression to OA and is therefore started on DHCQ 300 mg twice daily (for a total dose of 600 mg per day [10 mg/kg/day]).

(5) 49 year old male presents with intermittent pain in his left knee. X-ray reveals K-L grade 1 OA and MRI demonstrates a degenerative meniscal tear and moderate synovial enhancement consistent with synovitis. The patient is offered arthroscopic meniscal debridement but declines surgical intervention. Based on the clinical history and the presence and measurement of abnormal clinical and imaging markers, he is determined to have early-stage OA. To treat and prevent the progression of his early-stage OA, he is prescribed a combination of DHCQ 550 mg daily+atorvastatin 40 mg daily.

Example 16

Use of DHCQ for Treatment of Systemic Lupus Erythematosus

Systemic lupus erythematosus (SLE) is a systemic inflammatory disorder with protean manifestations. The involvement of endosomal toll-like rececptors (TLRs including TLR7 and TLR) have been strongly implicated in disease pathogenesis (Rahman et al, 2008. NEJM. (9)929-939, PMID#18305268) and the therapeutic efficacy of hydroxychoroquine, presumably acting via endosomal inhibition, has been well established (Rahman et al, 2008. NEJM. (9)929-939, PMID#18305268). However, as SLE is a chronic disease, most patients require long term therapy with HCQ and a reason for discontinuation is ocular deposition and potential ocular toxicity (Terahi et al, 2008. Semin Opthal. (3):201-208. PMID#. 18432546).

Examples of humans at high risk for development, with preclinical, or with established SLE, and their treatment with DHCQ, include:

(1) A 22 year old female presents with malar rash, arthralgia and is found to have nephritis as evidenced by elevated serum creatinine, and a urinalysis demonstrating red blood cell casts. She is treated with prednisone, cyclophosphamide, and HCQ and after several months demonstrates remission of all symptoms except mild arthralgia and return of her malar rash with heavy sun exposure. Cyclophosphamide is discontinued and prednisone is tapered off. Given evidence for reduced risk of relapse in SLE patients treated with ongoing HCQ she is instructed to continue for life. Given the need for long term therapy, there is increased risk of retinal toxicity. To avoid retinal toxicity, the patient is switched from HCQ to DHCQ treatment and after 5 years of aminoquinoline therapy ophthalmic exams for retinal toxicity are initiated on an every 2-year schedule.

(2) A 34 year old female with a 12 year history of SLE is seen in follow up. Initial presentation included rash, arthritis, and acute glomerulonephritis which was treated with prednisone and cyclophosphamide which was then transitioned to azathioprine and HCQ. Flares have occurred on approximately six occasions each responsive to low to moderate doses of prednisone. However, on a recent ophthalmologic evaluation using fundus autofluorescence (FAF), early changes consistent with possible retinopathy are observed. Given the established efficacy of antimalarial therapy to prevent and decrease the severity of flares of SLE, in the setting of early retinopathy, her treatment is changed from HCQ to DHCQ 550 mg daily. She continues on DHCQ 550 mg daily without progression of maculopathy on yearly opthalmic examination for the subsequent 10 years. Furthermore she notes no increased rate or severity of SLE flares over the same 10 years.

(3) A 28 year old female medical resident is diagnosed with SLE based on malar rash, photosensitivity, arthritis, oral ulcers, and pleuritis. She is 52 kg and is treated with hydroxychloroquine 200 mg with only partial response to therapy. She is highly resistant to use corticosteroids due to her small frame and low bone mass and she declines immunosuppressants due to the frequent contact with sick patients. She and the physician are aware of her increased risk of retinal toxicity with a higher dose of hydroxychloroquine, thus she is prescribed DHCQ 300 mg twice per day (600 mg total per day) with resolution of all SLE signs and symptoms. Opthamologic screening at 5 and 10 years of treatment with DHCQ demonstrates no evidence of retinal toxicity, and after 10 years of treatment with DHCQ ophthalmic monitoring is performed every 2 years to monitor for retinal toxicity, and over an additional 10 years of therapy no retinal toxicity is observed.

Example 17

Use of DHCQ for Treatment of Non-Alcoholic Fatty Liver Disease (NASH) in Humans

Non-alcoholic fatty liver disease (NALFD) is a common condition characterized by fat deposition in the liver. Patients with NAFLD are at significant risk for development of non-alcoholic steatohepatitis, an inflammatory liver disease dependent on TLR4 activation by endotoxin in the gastrointestinal tract. Given the observed ability of hydroxychloroquine to abrogate LPS mediated TLR4 activation, prescription of hydroxychloroquine is considered. However, the patient is a known type 2 diabetic, a condition commonly co-existing with NAFLD/NASH, and this has resulted in early diabetic retinopathy. As NASH/NAFLD is a chronic disease, long term therapy with HCQ would be required putting the patient at risk for ocular deposition and potential ocular toxicity.

Examples of humans at high risk for development of, with preclinical, or with established NASH, and their treatment with DHCQ, include:

(1) A 59 year old a man is seen on routine follow up for longstanding Type 2 diabetes. He is noted to have elevated AST and ALT to twice the upper limit of normal. He is asymptomatic and reports no hepatoxic medications. Abdominal ultrasounds is consistent with fatty infiltration of the liver. Based on the clinical presentation and abnormal inflammatory and imaging markers, the patient is determined to be at high risk for progression to NASH. Therapy with hydroxychloroquine is considered but in an effort to decrease risk of retinal toxicity, the patient is treated with DHCQ 550 mg per day, which prevents the patient from progressing to NASH, and after 10 years of DHCQ therapy the patient is screened for retinal toxicity and none is found and ophthalmic screening is continued on an every 5 year basis.

(2) A 53 year old man is seen for polyuria (frequent urination). He is found to have a fasting glucose of 390 mg/dL and hemoglobin A1C of 8.5 mg/dL> It is noted that his hepatic enzymes (ALT and AST) are nearly three times the upper limit of normal and high sensitivity CRP (hsCRP) is elevated at 2.1. He is otherwise asymptomatic and reports no hepatoxic medications. Abdominal ultrasounds is consistent with fatty infiltration of the liver and liver biopsy reveal hepatic steatosis with clusters of macrophages. Therapy with insulin and metformin is intiated with control of blood sugar and at 6 months hemoglobin A1c is reduced to 7.5 mg/dL. However, AST and ALT are still nearly three times the upper limit of normal and hsCRP is 1.9. Based on the measured abnormal clinical, abnormal metabolic, and abnormal imaging markers, the patient is determined to have NASH. HCQ is considered but in an effort to decrease risk of retinal toxicity, the patient is treated with DHCQ 600 mg/day, which prevents the patient from progressing results in normalization of AST and ALT and a reduction in hsCRP to 0.9 mg/dL. Notably, hemoglobin A1c is reduced to 6.1 without further titration of primary hypoglycemic therapy. After 10 years of DHCQ therapy the patient is screened for retinal toxicity and none is found, and the patient subsequently screened every other year by ophthalmic examination for retinal toxicity.

Example 18

Treatment of the Metabolic Disease Non-Alcoholic Steatohepatitis (NASH) with DHCQ A 49 year old man has elevated liver enzymes with an alanine transaminase (ALT) level of 59 IU/L and an aspartate transaminase (AST) level of 55 IU/L. Ultrasound of the liver will be consistent with fatty infiltration and serologic tests will be negative for hepatitis B or C virus and he will deny use of alcohol. The patient is found to have an impaired fasting glucose level of greater than 120 and elevated triglycerides greater than 320 mg/dL. He undergoes a liver biopsy that demonstrates steatosis ballooning, degeneration of hepatocytes, as well as mixed portal inflammation but no fibrosis. Based on these abnormal findings and markers he is diagnosed with NAFLD and early NASH, and based on this diagnosis he is prescribed DHCQ 600 mg per day. Serum samples are collected at baseline and after 2 months of treatment to evaluate for levels of alanine aminotransferase (ALT; also known as serum glutamic pyruvate transaminase [SGPT]) and aspartate transaminase (AST; also known as serum glutamic oxaloacetic transaminase [SGOT]) alanine aminotransferase (ALT) as well as a panel of multiplex cytokines. Reductions in the ALT, AST and/or cytokines indicate a positive response to treatment.

Example 19

Treatment of the Metabolic and Inflammatory Diseases

Treatment of Type II Diabetes and the Metabolic Syndrome with DHCQ

Examples of humans at high risk for development, with preclinical, or with established type II diabetes and/or metabolic syndrome, and their treatment with DHCQ, include:

(1) A 42 year old man with history of obesity (BMI 31) found to have a fasting glucose of 106 mg/dL, an LDL level of 135, and a triglyceride level of 220. Evaluations for secondary causes of hyperglycemia are negative and based on the abnormal metabolic markers he is determined to be at increased risk for development of an inflammatory disease or disease associated with inflammation. Based on this increased risk, he is treated with atorvastatin 40 mg and DHCQ 400 mg daily.

(2) A 48 year old man with history of obesity (BMI 30) is found to have a fasting glucose of 121 mg/dL, an LDL level of 135, and a triglyceride level of 220. High sensitivity CRP (hsCRP) is elevated at 1.9. He is treated for 4 months with atorvastatin 40 mg with reduction in LDL to 105 and hsCRP to 1.7. He is then started DHCQ 400 mg daily with further reduction in LDL to 95 and hsCRP to 0.9. In addition, fasting glucose levels fall to 101 without progression to type 2 diabetes over a period of 5 years.

(3) A 53 year old man with a history of hypertension and previous myocardial infarction is noted to have an LDL cholesterol level of 140 mg/dL and a high sensitivity CRP (hsCRP) of 1.6 mg/L. He is treated with atorvastatin with a decrease in his LDL to 115 mg/dl and a fall in his hsCRP to 1.2. He is subsequently treated with DHCQ 600 mg daily, clinically does well with further reduction in LDL to 99 mg/dl and hsCRP to 0.8. After 10 years of therapy he is screened for and has no evidence of retinal toxicity.

Example 20

Use of DHCQ for Treatment of Systemic Lupus Erythematosus

Systemic lupus erythematosus (SLE) is a systemic inflammatory disorder with protean manifestations. The involvement of endosomal toll-like rececptors (TLRs including TLR7 and TLR) have been strongly implicated in disease pathogesis (Rahman et al, 2008. NEJM. (9)929-939, PMID#18305268) and the therapeutic efficacy of hydroxychoroquine, presumably acting via endosomal inhibition, has been well established (Rahman et al, 2008. NEJM. (9)929-939, PMID#18305268). However, as SLE is a chronic disease, most patients require long term therapy with HCQ and a major reason for discontinuation is ocular deposition and potential ocular toxicity (Terahi et al, 2008. Semin Opthal. (3):201-208. PMID#. 18432546).

Examples of humans at high risk for development, with preclinical, or with established SLE, and their treatment with DHCQ, include:

(1) A 22 year old female presents with malar rash, arthralgia and is found to have nephrotic syndrome as evidenced by elevated serum creatinine and a urinalysis demonstrating red blood cell casts. She is treated with prednisone, cyclophosphamide, and HCQ and after several months demonstrated remission of all symptoms except mild arthralgia and return of her malar rash with heavy sun exposure. Cyclophosphamide is discontinued and prednisone is tapered off. Given evidence for reduced risk of relapse in SLE patients treated with ongoing HCQ she is instructed to continue for life. Given the need for long term therapy, there is increased risk of retinal toxicity. To avoid retinal toxicity, the patient is switched from HCQ to DHCQ treatment.

(2) A 34 year old female with a 12 year history of SLE is seen in follow up. Initial presentation was for rash, arthritis, and acute glomerulonephritis which was treated with prednisone and cyclophosphamide which was then transitioned to azathioprine. Flares have occurred on approximately six occasions each responsive to low to moderate doses of prednisone. However, on a recent ophthalmologic evaluation using fundus autofluorescence (FAF), early changes consistent with possible hydroxychloroquine retinopathy. Given the established efficacy of antimalarial therapy to prevent and/or decrease flares of SLE but in the setting of early hydroxychloqoruine maculopathy, she is treated with DHCQ 400 mg daily without progression of maculopathy on yearly examination for the subsequent 10 years. Furthermore she note no increased rate or severity of SLE flares over the same 10 years.

(3) A 28 year old female medical resident is diagnosed with SLE based on malar rash, photosensitivity, arthritis, oral ulcers, and pleuritis. She is 52 kg and is treated with hydroxychloroquine 200 mg with only partial response to therapy. She is highly resistant to use corticosteroids due to her small frame and low bone mass and she declines immunosuppressants due to the frequent contact with sick patients. She and the physician are aware of her increased risk of retinal toxicity with a higher dose of hydroxychloroquine, thus she is prescribed DHCQ 600 mg day with resolution of all SLE signs and symptoms. Yearly opthamologic screening reveals no evidence of retinopathy at 5 and 10 years of therapy.

(4) A 30 year old female is tired, develops a malar rash, and is found to have an anti-Sm antibody titer of 1:320. She is at-risk for the development of SLE, and is treated with DHCQ 550 mg/day, her symptoms improve, and after 5 years of therapy retinal monitoring is started on an every-other year basis and no retinal toxicity is observed.

Example 21

Treatment of the Metabolic and Inflammatory Disease Type II Diabetes with DHCQ Examples of humans at high risk for development, with preclinical, or with established type II diabetes, and their treatment with DHCQ, include:

(1) A 42 year old man with history of obesity (BMI 31) is found to have a fasting glucose of 106 mg/dL, an LDL level of 135, and a triglyceride level of 220. Evaluations for secondary causes of hyperglycemia are negative and he is treated with atorvastatin 40 mg and DHCQ 400 mg daily.

(2) A 53 year old man with a history of hypertension and previous myocardial infarction is noted to have an LDL cholesterol level of 140 mg/dL. He is treated with atorvastatin with a decrease in his LDL to 115 mg/d. He is subsequently treated with DHCQ 600 mg daily, clinically does well, and after 10 years of therapy is screened for and has no evidence of retinal toxicity.

Example 22

Treatment of the Chronic Immune Activation and Metabolic Abnormalities in HIV Infection with DHCQ A 38 year old man with a 9 year history of HIV disease, treated with a triple drug regimen of anti-retroviral therapy has an undetectably viral load (<10,000 copies/ml) and CD4 T cell count of 490. He feels well and has had no opportunistic infections. He is noted to have impaired fasting glucose level of 109 mg/dL and elevated triglycerides at 299 mg/dL. High sensitivity C-reactive protein (hsCRP) level is 5.8 mg/L. A coronary CT scan reveal significant calcification of the coronary arteries with an Agatston score of 124 but an exercise stress test reveals no inducible cardiac ischemia. Based on these abnormal inflammatory and abnormal metabolic markers, he is prescribed DHCQ 600 mg daily, clinically does well, and after 10 years of therapy is screened for and has no evidence of retinal toxicity.

Example 23

Treatment of Atherosclerosis with DHCQ

Examples of humans at high risk for development, with preclinical, or with established atherosclerosis, and their treatment with DHCQ, include:

(1) A 59 year old man with a history of hypertension is evaluated for exertional chest pain. Exercise stress imaging reveals a reversible region of ischemia in the lateral wall of the heart and he is taken to cardiac catheterization which reveals diffuse lesions of 40-60% stenosis in the left main and left anterior descending coronary arteries. He is treated with DHCQ 500 mg per day and he does not have further myocardial infarction.

(2) A 48 year old man with a no active medical problems and no medications is seen for a first episode of acute chest pain lasting 1 hour and diagnosed with a non-ST elevation myocardial infarction. He has a family history of premature coronary artery disease. Cardiac stress test reveals no focal areas of defect on by electrocardiogram (ECG) or nuclear perfusion imaging. His LDL is 161 mg/dL. He is treated and released with new medication regimen including daily aspirin 81 mg and atorvastatin 40 mg. At follow up in 8 weeks he is symptom free with an LDL of 90 but is noted to have an ALT of 71 and AST of 66, both of which were previously normal. A dose reduction of atorvastatin to 20 mg results in minimal chance in ALT/AST but with a rise in LDL to 140, well above goal for LDL for known coronary disease. He is prescribed DHCQ 400 mg daily to take in addition to atorvastatin 20 mg daily with a fall in LDL to 110 mg/dL and normalization of his AST/ALT. His atorvastatin is increased back to 40 mg with a reduction in LDL to 80 mg/dL without rise in AST/ALT. Therapy is continued for over 10 years without stable LDL, AST/ALT as well as normal retinal exam at 5, 10, and 20 years of therapy.

Example 24

Use of Desethylhydroxychloroquine (DHCQ), or Combination DHCQ+Atorvastatin, Therapy to Prevent Development of and to Reduce the Severity of Rheumatoid Arthritis (RA)

Humans are screened for evidence of early RA or for being at high risk for the development of RA. Findings that suggest an individual human has early RA include one or more of the following: presence of one or more swollen joints, the presence of anti-CCP or rheumatoid factor antibodies, evidence of synovial enhancement on MRI scan or ultrasound, and markers including elevations in autoantibodies and cytokines demonstrated to provide predictive utility for the subsequent development of RA (as described in Sokolove et al, PLoS One. 2012; 7(5):e35296, PMID: 22662108). Factors that place an asymptomatic individual, or individual with monoarthritis, at increased risk for development of RA include one or more of the following: a family history of RA (particularly in a first-degree relative), increased anti-CCP and/or rheumatoid factor antibodies, and a genetic profile with increased susceptibility to RA, and/or one or more joints exhibiting synovitis (joint swelling and inflammation).

Further, humans at high risk for RA or with early RA can be tested for the presence of inflammation in the involved joint to identify individuals most-likely to respond to treatment with DHCQ or treatment with a combination of DHCQ+atorvastatin. Testing for joint inflammation can be performed with imaging markers, such as MRI with or without gadolinium contrast, or an ultrasound, to determine if one or more of the following features indicative of inflammation are present: synovial enhancement or proliferation, an effusion is present, and bone marrow edema. Molecular markers of inflammation can also be tested for, including one or more of CRP, ESR and inflammatory cytokines. Finally, clinical history and exam are used to assess inflammation—including the presence of synovitis on physical examination, an effusion on physical exam, or morning stiffness >1 hour on history.

Individual humans with preclinical or early RA, particularly when evidence of inflammation is found using imaging, molecular or clinical marker, can be treated with DHCQ, or a combination of DHCQ+atorvastatin, to prevent the progression of pre-clinical or early RA. The dose of DHCQ is generally at least about 400 mg/day, but can be between about 100-1600 mg/day, or between about 550 and 1000 mg/day. The DHCQ can be delivered in individual tablets or capsules, or the combined DHCQ+atorvastatin delivered as a combined tablet or capsule that includes both drugs.

All publications and patent documents cited herein are incorporated by reference in their entirety. To the extent the material incorporated by reference contradicts or is inconsistent with the present specification, the present specification will supersede any such material.

What is claimed is:

1. A method of treating an inflammatory disease comprising: administering to an individual in need thereof who is at increased risk of retinal toxicity, with one or more daily doses of a pharmaceutical composition comprising desethylhydroxychloroquine (DHCQ) or pharmaceutically acceptable salts or esters thereof, wherein the daily dose is 400-600 mg/day of DHCQ or pharmaceutically acceptable salts or esters thereof.

2. The method of claim 1, wherein the daily amount of DHCQ or pharmaceutically acceptable salts or esters thereof administered to the individual for the first 1 to 16 weeks is higher than the daily amount of DHCQ or pharmaceutically acceptable salts or esters thereof administered subsequently.

3. The method of claim 1, wherein the inflammatory disease is systemic lupus erythematosus.

4. The method of claim 1, wherein the individual exhibits symptoms of the early stages of the inflammatory disease.

5. The method of claim 1, wherein the individual is asymptomatic and identified as being at increased risk for developing the inflammatory disease.

6. The method of claim 1, wherein said administering is carried out for a period of at least 10 years.

7. The method of claim 1, wherein there is reduced screening for retinal toxicity compared to treatment with HCQ.

8. The method of claim 7, wherein screening starts after 10 years of said administration.

9. A method of inhibiting the development of an inflammatory disease in a mammal comprising:
   (i) identifying an individual exhibiting early stages of an inflammatory disease,
   (ii) measuring a marker of inflammation in the individual,
   (iii) comparing the level of the marker of inflammation measured in the individual with the reference range of the normal level of the biomarker of inflammation measured in healthy individuals to determine if the individual exhibits increased inflammation,
   (iv) if the individual shows increased inflammation, treating the individual with one or more daily doses of a pharmaceutical composition comprising DHCQ or pharmaceutically acceptable salts or esters thereof, wherein the daily dose is 400-600 mg/day of DHCQ or pharmaceutically acceptable salts or esters thereof.

10. The method of claim 9 wherein the marker of inflammation is measured by imaging.

11. The method of claim 9 wherein the marker of inflammation is a molecular marker.

12. The method of claim 9 wherein the marker of inflammation is a clinical marker.

13. The method of claim 9, wherein the inflammatory disease is type II diabetes.

14. The method of claim 9, wherein the inflammatory disease is non-alcoholic steatohepatitis.

15. The method of claim 1, further comprising initiating retinal toxicity screening of the individual beginning no earlier than about 5 years after initiating said treating.

16. The method of claim 15, wherein said retinal toxicity screening is carried out at intervals of about 2 years.

17. The method of claim 9, further comprising initiating retinal toxicity screening of the individual beginning no earlier than about 5 years after initiating said treating.

18. The method of claim 17, wherein said retinal toxicity screening is carried out at intervals of about 2 years.

19. The method of claim 9, wherein there is reduced screening for retinal toxicity compared to treatment with HCQ.

20. The method of claim 9, wherein said individual does not require screening for retinal toxicity after initiating said treating.

21. The method of claim 1, wherein the inflammatory disease is rheumatoid arthritis.

22. The method of claim 1, wherein the inflammatory disease is a degenerative disease selected from the group consisting of osteoarthritis, Alzheimer's disease, and macular degeneration.

23. The method of claim 1, wherein the inflammatory disease is a metabolic disease selected from the group consisting of type II diabetes, atherosclerosis and non-alcoholic steatohepatitis.

24. The method of claim 1, wherein the inflammatory disease is a chronic infection.

25. The method of claim 23, wherein the inflammatory disease is type II diabetes.

26. The method of claim 23, wherein the inflammatory disease is non-alcoholic steatohepatitis.

27. The method of claim 24, wherein the chronic infection is HIV.

28. The method of claim 1, wherein after 10 years of said administration, the individual is substantially without symptoms of retinal toxicity.

29. The method of claim 1, wherein said individual does not require screening for retinal toxicity after initiating said treating.

30. The method of claim 10, wherein the imaging is selected from the group consisting of magnetic resonance imaging, ultrasound imaging, and computed tomography.

31. The method of claim 11 wherein the molecular marker is selected from the group consisting of a c-reactive protein, a cytokine, an antibody, a DNA sequence, an RNA sequence, and insulin resistance.

32. The method of claim 12 wherein the clinical marker is a finding of swelling on physical examination.

* * * * *